(12) United States Patent
Gevins et al.

(10) Patent No.: US 6,947,790 B2
(45) Date of Patent: Sep. 20, 2005

(54) NEUROCOGNITIVE FUNCTION EEG MEASUREMENT METHOD AND SYSTEM

(75) Inventors: Alan Gevins, San Francisco, CA (US); Michael Smith, Alameda, CA (US)

(73) Assignee: SAM Technology, Inc., San Francisco, CA (US)

( * ) Notice: Subject to any disclaimer, the term of this patent is extended or adjusted under 35 U.S.C. 154(b) by 471 days.

(21) Appl. No.: 10/121,606

(22) Filed: Apr. 15, 2002

(65) Prior Publication Data

US 2003/0013981 A1 Jan. 16, 2003

Related U.S. Application Data

(63) Continuation-in-part of application No. 09/603,218, filed on Jun. 26, 2000, now Pat. No. 6,434,419.

(51) Int. Cl.[7] .............................. A61B 5/04; A61B 5/05
(52) U.S. Cl. ....................................... 600/544; 600/410
(58) Field of Search ................................ 600/544–547, 600/587, 410, 411

(56) References Cited

U.S. PATENT DOCUMENTS 5,295,491 A * 3/1994 Gevins ........................ 600/544
6,434,419 B1 * 8/2002 Gevins et al. ............... 600/544

2002/0042563 A1 * 4/2002 Becerra et al. ............. 600/407

* cited by examiner

*Primary Examiner*—Eric F. Winakur
*Assistant Examiner*—Matthew Kremer
(74) *Attorney, Agent, or Firm*—Eliot Gerber

(57) ABSTRACT

An efficient, objective testing method and system for evaluating changes in mental function is described. The method and system are based on measuring an individual's behavioral responses and brain function during a brief cognitive test battery and passive control conditions. The method and system is designed to assess an individual's fundamental cognitive functions, and whether those functions have been significantly affected by a variety of factors such as progressive disease processes, medication, stress, fatigue, training, or the passage of time. The method and system can be used to determine whether drugs being evaluated to treat diseases or conditions affecting cognitive brain function have a significant positive effect on delaying or improving the symptoms of such a disease or condition, especially during clinical trials for drug approval and subsequent marketing. The method and system may also be employed as part of the successful diagnosis or ongoing treatment of neurological diseases or conditions that directly or indirectly affect human neurocognitive performance. The method and system may also be used to determine transitory changes in overall cognitive function due to emotional stress or fatigue, and more long lasting changes in overall cognitive function following training and educational programs.

27 Claims, 17 Drawing Sheets

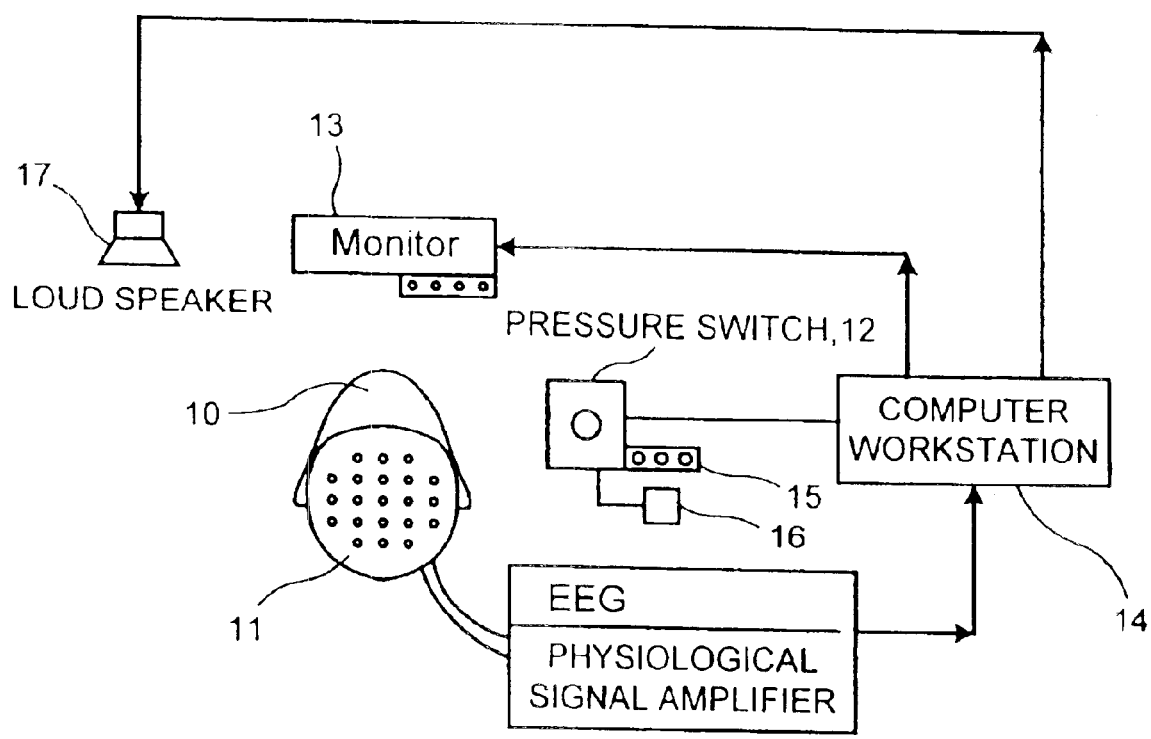
F I G. 1

NEUROCOGNITIVE FUNCTION EEG MEASUREMENT METHOD AND SYSTEM

RELATED APPLICATION

This application is a continuation-in-part application partly based on Ser. No. 09/603,218 filed Jun. 26, 2000 now U.S. Pat. No. 6,434,419 and entitled "Neurocognitive Ability EEG Measurement Method and System."

GOVERNMENT SUPPORT

This invention was made with government support under contract R44AA11702, awarded by the National Institute on Alcohol Abuse and Alcoholism. The government has certain rights in the invention.

BACKGROUND OF THE INVENTION

1. Field of the Invention

The present invention relates to psychometric, neuropsychological, and neurophysiological tests for measuring mental function and more particularly to the use of electroencephalogram (EEG) recordings for such measurements.

2. Description of the Related Art

There is currently no method that efficiently and objectively measures an individual's fundamental cognitive brain functions ("neurocognitive functions"). Neither is there a method that is able to do so on repeated occasions in order to measure changes in fundamental neurocognitive functions due to disease, injury, or other conditions affecting higher cognitive brain functions, or such fluctuating changes due to ongoing remedial treatment.

The presently available various psychometric tests of cognitive function, such as the Wechsler Adult Intelligence Scale (WAIS), each suffer from one or more deficiencies. These deficiencies include cultural bias, subjective interpretation, excessive test length, cumbersome retesting, high cost, and lack of assessment of the subject's motivational factors in performing the test. In addition, most test instruments lack multiple applications of the test that would be needed for repeated testing. There are also a number of ad-hoc computerized cognitive test batteries, such as CANTAB, that use a mix of tasks derived from laboratory research and clinical neuropsychological practice and that ameliorate some of these shortcomings. However, no psychometric test or cognitive test battery provides direct information about the subject's actual brain function and hence supplies no information relative to the putative pharmacological action of a drug, disease, injury or therapy which is being studied or evaluated. This lack of suitable tests is a major barrier to long-term assessment of changes in an individual's fundamental neurocognitive functions. This assessment is of paramount importance in evaluating the success of a putative treatment for any form of condition affecting higher cognitive brain functions, for example drugs to aid memory in elderly patients. In principle direct measurement of brain functions underlying cognitive functions, by EEG measurements of brain wave activity, could overcome these deficiencies. Prior attempts at such EEG measurements, however, have not been fruitful because of one or more major shortcomings. First, there was often a failure to measure brain activity while the subject performed a task taxing the subject's fundamental mental processes, such as attention, memory, and language. Merely recording brain activity while the subject sits idly, watching a meaningless flashing light, or performing a task not requiring her or his full attention is often insufficient to produce patterns of brain activity characterizing individual differences in neurocognitive functioning, or changes in an individual's neurocognitive functions over time. Second, there was most often a reliance on single measures of brain function, such as EEG alpha band power or P300 evoked potential amplitude, that by themselves are insufficient to adequately characterize individual differences in fundamental neurocognitive functions or changes in an individual's fundamental neurocognitive functions due to a disease, its treatment, or other causes. Third, prior brain function studies did not combine measures of task performance with brain function measures in the same mathematical function to characterize individual differences in fundamental neurocognitive functions or changes in an individual's fundamental neurocognitive functions due to a disease, its treatment, or other causes. Similarly, studies using other methods of measuring brain function, such as positron emission tomography or functional magnetic resonance imaging, have not combined measures of task performance with brain function measures in a mathematical function to characterize individual differences in fundamental neurocognitive functions or changes in an individual's fundamental neurocognitive functions due to a disease, its treatment, or other causes.

In Schmidt et al., U.S. Pat. No. 5,339,826, the effectiveness of video-taped training material is tested using EEG. In one method, the student's brain wave alpha and beta band activity is analyzed to determine attention and cognitive activity. In another method, EP (Evoked Potential) responses are measured using multiple-choice questions.

In Cohen U.S. Pat. No. 4,203,452, a single channel of EEG is measured in an attempt to ascertain if a student is undergoing short-term learning or long-term learning.

In Gevins U.S. Pat. No. 5,447,166, EEG signals are used to alter a computer program, i.e. present more or less difficult test material to the user.

Bennett U.S. Pat. No. 3,809,069 seeks to measure the intelligence of a subject using pulsed stimuli to evoke the subject's responses, which are compared to the frequencies of responses of others.

Other possibly relevant patents are U.S. Pat. Nos. 5,991,581; 6,087,090; 6,159,014; 6,280,198 and 6,309,361.

These patents, and the other references cited, are incorporated by reference herein.

SUMMARY OF THE INVENTION

In accordance with the present invention, a novel method and system called "Neurocognitive Function EEG Measurement System" is provided for testing the brain activity of subjects while they perform a brief cognitive task battery in order to measure fundamental neurocognitive functions.

The unique advantage of this system is that, by measuring neurological signals of basic cognitive processes, it is able to determine a subject's neurocognitive status efficiently, objectively, without cultural bias, and with comparative ease on repeated occasions. This differs from current psychometric tests or cognitive task batteries that are usually lengthy, subjectively interpreted, depend in part upon culturally specific knowledge, not designed for repeated testing of the same person, and that do not directly measure brain function. The "Neurocognitive Function EEG Measurement System" also differs from prior attempts to use measures of brain activity to characterize cognitive function in one or more of four essential respects. First, prior methods only recorded brain activity during passive conditions that did not require that a subject perform and respond to tasks that test fundamental cognitive functions such as focused attention, divided attention, selective attention, working memory, intermediate term memory, or language comprehension and expression functions, and were thus not specific to higher intellectual functioning. Second, prior methods only compared an individual to a normative database gathered from populations of demographically matched individuals, rather than to the individual's own prior baseline data, and thus did not have sufficient sensitivity to measure relatively subtle changes in a particular individual's neurocognitive functioning over time. Third, prior methods only used single measurements of brain function that by themselves are insufficient to adequately characterize individual differences in fundamental neurocognitive functions or changes in an individual's fundamental neurocognitive functions due to a disease, its treatment or other causes. Fourth, prior methods did not consider both brain function and its resultant behavioral performance. They did not combine measures of task performance (such as speed and accuracy of response to each cognitive task trial) with brain function measures in the same mathematical function in order to characterize individual differences in fundamental neurocognitive functions or changes in an individual's fundamental neurocognitive functions due to a disease, its treatment, or other causes. By contrast, the "Neurocognitive Function EEG Measurement System" combines several measurements of brain function while the subject is both resting and performing a cognitive task with measures of task performance, and compares these measurements to the individual's own baseline data. The system thus overcomes the limitations of current testing systems, and consequently has higher sensitivity to individual differences in fundamental neurocognitive functions or changes in an individual's fundamental neurocognitive functions due to a disease, its treatment, or other causes.

The system operates as follows: the subject is tested on two or more occasions, as deemed necessary, while performing a brief cognitive task battery as his or her brain waves are recorded. Changes in the subject's neurocognitive function are determined by combining measures of task performance and brain wave measures according to a formula previously determined from a normative reference group of subjects.

The system uses a digital computer workstation having a screen and a response input device, and an EEG device (electroencephalograph) to measure the brain waves of the subject. The EEG device also measures eye and scalp muscle activity and head movements in order to determine whether and how artifacts contaminate the brain waves. The system either removes such contaminants whenever possible or else discards the contaminated data. The subject is presented with a brief task battery on the screen that tests one or more fundamental cognitive functions, preferably the functions of attention and memory. A subject's behavioral responses and brain waves are measured as she or he performs a series of repetitions of easy and more difficult versions of the task. The subject's brain waves are also recorded at rest for comparison with data recorded during performance of the task. The preceding procedure of collecting and analyzing data is repeated over a normative group of subjects recorded while in a baseline state and after a drug or other means or conditions have altered their cognitive functioning.

The measures are grouped into classes, preferably three classes called Behavioral Performance, Neurophysiological Cognitive, and Neurophysiological Alertness. Rules based on expert knowledge of neuropsychology and neurophysiology are then applied to each measure within each class. The rules test whether and how each measure differs in an expected manner between each subject's baseline and altered states. An equation is then computed, preferably using a neural network or other type of statistical decision function, that weights and combines the decision outputs of the classes into a score, preferably called a Neurocognitive Function Change (NCFC) score, that distinguishes baseline from altered states. The NCFC score of a new subject is determined by first measuring her or his behavioral responses and EEG while performing the same task battery in baseline and subsequent, possibly altered, states, then computing the appropriate primary and secondary measures and applying the rules, and finally weighting the outputs of the rules according to the equation determined from the normative group.

Objectives of the present invention are to provide a method and system to:

1. Measure fundamental neurocognitive functions of a subject efficiently, objectively, inexpensively, and with minimal cultural bias;

2. Repeatedly measure fundamental neurocognitive functions of a subject in order to measure changes due to diseases, injury, fatigue, or other conditions, or treatment with drugs, food supplements, or other remedial therapies;

3. Repeatedly measure fundamental neurocognitive functions in order to measure changes due to training, learning, or use of drugs or other interventions that improve brain function or slow the progression of diseases or conditions that affect higher cognitive brain functions; and 4. Repeatedly measure fundamental neurocognitive functions, alone or in concert with symptomatic or asymptomatic blood borne or other measurable marker shown to be associated with a disease or condition, in order allow early detection of impairment due to that disease or condition or improvement due to treatment, thus being able to both speedily predict a deleterious condition and further evaluate efficacy of treatment of said condition.

It is a feature of the present invention to measure neurophysiological signals underlying fundamental cognitive functions while subjects perform tasks engaging fundamental cognitive functions such as sustained attention, divided attention, selective attention, working memory, intermediate term memory, and while are at rest.

It is a further feature of the present invention that the tasks used for testing do not depend on prior knowledge that is likely to be culturally biased, such as reading a particular language or making use of information derived from a particular cultural context.

It is a further feature of the present invention that the tasks used for testing may include tests of receptive and expressive language functions.

It is a further feature of the present invention to use an easy and a more difficult version of a task for testing in order to apply a calibrated difference in mental workload to the subject from which the subject's mental effort and relative amount of brain utilization can be estimated.

It is a further feature of the present invention to measure behavioral performance, such as performance accuracy and speed, while performing the cognitive tasks.

It is a further feature of the present invention to measure neurophysiological signals characterizing the subject's mental effort and amount of brain utilization to perform the cognitive tasks.

It is a further feature of the present invention to measure neurophysiological signals characterizing the subject's sustained focused attention, sustained divided attention, selective attention and transient focused attention while performing the cognitive tasks.

It is a further feature of the present invention to measure neurophysiological signals characterizing the subject's preparatory attention and neurocognitive strategy while performing the cognitive tasks.

It is a further feature of the present invention to measure neurophysiological signals characterizing the subject's perceptual and cognitive speed while performing the cognitive tasks.

It is a further feature of the present invention to measure neurophysiological signals characterizing the subject's alertness during the resting control tasks and while performing the cognitive tasks.

It is a further feature of the present invention to measure neurophysiological signals characterizing the subject's working memory and intermediate term memory while performing cognitive tasks that test both working and intermediate term memory.

It is a further feature of the present invention to measure behavioral performance differences between performing an easy and a more difficult version of a cognitive task, and to measure differences in neurophysiological signals between resting and easy, resting and difficult and easy and difficult task versions, in order to measure how the subject's brain and behavior respond to changes in mental workload imposed by the tasks.

It is a further feature of the present invention to measure changes in neurophysiological signals as a subject performs repeated trials of the cognitive tasks during one test session in order to characterize how quickly the subject's brain adapts to the challenge imposed by the tasks.

It is a further feature of the present invention to measure differences in neurophysiological signals and cognitive task performance between initial and subsequent trials of an easy and a more difficult version of a cognitive task during one test session in order to measure how quickly the subject's brain and behavior adapt to changes in mental workload imposed by the task.

It is a further feature of the present invention to compare measurements of neurophysiological signals and cognitive task performance between successive test sessions to determine whether the subject's neurophysiological signals and cognitive task performance have changed due to an underlying clinical condition thus allowing detection of the aforementioned condition.

It is a further feature of the present invention to compare measurements of a subject's neurophysiological signals and cognitive task performance from one or more test sessions to similar measurements made from a normative population to determine whether the subject's neurophysiological signals and cognitive task performance are impaired due to an underlying clinical condition, thus allowing detection of the aforementioned condition.

It is a further feature of the present invention to compare measurements of neurophysiological signals and cognitive task performance between successive test sessions to determine whether the subject's neurophysiological signals and cognitive task performance have changed and continue to change when under the influence of an administered drug.

It is a further feature of the present invention to compare measurements of neurophysiological signals and cognitive task performance between successive test sessions to determine whether the subject's neurophysiological signals and cognitive task performance have changed and continue to change under a regime of any non-drug related therapy meant to enhance such performance or delay its deterioration.

It is a further feature of the present invention to measure a multivariate combination of neurophysiological signals and cognitive task performance recorded under well-controlled testing conditions that, taken together, have high test-retest reliability and high sensitivity and specificity to alterations in an individual's fundamental neurocognitive functions consequent to a disease or its treatment, non-prescription psychoactive substances such as alcohol, antihistamines, caffeine, marijuana and other "recreational" drugs, food substitutes, additives, vitamins, sleep disruption or fatigue, and regimes of any non-drug related therapy meant to enhance cognitive performance.

It is a further feature of the present invention to determine an overall neurocognitive function change score or scores by combining, and comparing between test sessions, measurements of speed, accuracy and other features of task performance with brain wave (electroencephalogram or EEG) measurements characterizing alertness, sustained and transient focused attention, selective and divided attention, working and intermediate term memory, language comprehension and expression, brain utilization, neurocognitive strategy, and cognitive speed, combinations of differences in the preceding measurements between resting and easy and more difficult cognitive task versions, and combinations of differences in the preceding measurements between initial and subsequent trials of the cognitive task during one test session.

It is a further feature of the present invention to compute a plurality of primary measures from the data in order to characterize the above states and functions of alertness, attention, etc., preferably including: 1) the mean, standard deviation and variability of the subject's reaction time to each task trial; 2) the mean, standard deviation and variability of the accuracy of the subject's response to each task trial; 3) the amplitude of the subject's EEG alpha band activity recorded over parietal and prefrontal cerebral cortical brain regions; 4) the amplitude of the subject's EEG frontal midline theta activity; 5) the peak time of the subject's Contingent Negative Variation, N100, P200, P300, N400, P600 and Slow Wave evoked potential peaks elicited by the task stimuli; 6) the peak amplitude of the subject's Contingent Negative Variation, N100, P200, P300, N400, P600 and Slow Wave averaged evoked potential peaks elicited by the task stimuli; 7) the amplitude of the subject's frontal delta power associated with slow horizontal eye movements; 8) the amplitude of the subject's posterior theta and delta powers; 9) ratios of certain primary measures 1–6, for instance theta divided by alpha EEG power, or response accuracy divided by reaction time; 10) ratios of measures 3–9 between different locations on the scalp; and 11) measures of time series interdependency such as covariance, correlation, coherence or mutual information of primary measures 3, 4, 6 and 8 between different locations on the scalp. Secondary measures are then computed preferably including: 1) differences between or ratios of the primary measures between resting and the easy task version; 2) differences between or ratios of the primary measures between easy and more difficult task versions; 3) differences between or ratios of the primary measures between initial and subsequent repetitions of the task in the same session; and 4) differences between or ratios of secondary measures 1 and 2 between initial and subsequent repetitions of the task in the same session.

It is a further feature of the present invention to group the above measures into one or more classes, preferably three classes called: 1) Behavioral Performance, which measures the quality of a subject's performance of a cognitive test, for instance the speed and accuracy of responses to test questions; 2) Neurophysiological Cognitive, which measures central nervous system activity related to the regulation of attention, memory and other fundamental cognitive processes; and 3) Neurophysiological Alertness, which measures central nervous system activity related to the regulation of the degree of wakefulness.

It is a further feature of the present invention to repeat the procedure of collecting and analyzing data over one or more normative reference groups of subjects recorded while in a baseline state and after one or more drugs or other means or conditions have altered their cognitive functioning producing an altered state.

It is a further feature of the present invention to provide a plurality of ways to specify the baseline state, including preferably, the subject's first recording, the subject's most recent recording, a weighted average of all the subject's prior recordings, a particular prior recording before initiation of a drug or other therapy, a chosen set of prior recordings from the subject, or baselines previously determined from a normative reference group of subjects with demographic or state of health characteristics similar to those of the subject.

It is a further feature of the present invention to apply, for each subject within the normative group, one or more rules based on specialized expert knowledge to each measure within each of the classes of measures. The rules test whether and to what extent measures within each class differ in an expected manner between each subject's baseline and altered states.

It is a further feature of the present invention to compute an equation, preferably using a neural network or other type of statistical decision function, that weights and combines the decision outputs of the expert rules into a NCFC score that distinguishes baseline from altered states in each normative group of subjects.

It is a further feature of the present invention to determine the NCFC score of a new subject by first measuring her or his behavioral responses and EEG while performing the same task battery in baseline and subsequent, possibly altered states, then computing the appropriate primary and secondary measures and applying the expert rules, and finally combining the weighted outputs of the rules according to the above mentioned equation determined from an appropriate normative reference group.

It is a further feature of the present invention to determine whether a subject's baseline state is within normal limits by comparing the subject's baseline state to the baseline states of a normative group of subjects with similar demographic or state of health and current treatment characteristics.

It is a further feature of the present invention to determine a normal range of variation of a subject's NCFC score from the set of NCFC scores resulting from comparing the subject's prior baseline states to each other.

It is a further feature of the present invention to determine a typical normal range of variation of the NCFC score from the set of normal ranges of the NCFCs of each member of a normative reference group of subjects.

It is a further feature of the present invention to determine whether a subject's NCFC score on a particular test day or days represents an altered neurocognitive state by comparing the NCFC score from that day or days with the normal range of variation of the subject's NCFC scores.

It is a further feature of the present invention to determine whether a subject's NCFC score on a particular test day or days represents an altered neurocognitive state by comparing the NCFC score from that day or days with the typical normal range of variation of the NCFC scores of a normative reference group of subjects with similar demographic or health and treatment characteristics.

It is a further feature of the present invention to determine why a subject's NCFC score on a particular test day was considered to represent an altered neurocognitive state by comparing each of the classes of measures (preferably Behavioral Performance, Neurophysiological Cognitive, and Neurophysiological Alertness classes) from that day with their respective values in the baseline. For instance, if all three classes of measure differed from baseline, the subject was probably drowsy. If Neurophysiological Alertness was unchanged, while Behavioral Performance was unchanged or lower and Neurophysiological Cognitive was unchanged or higher than baseline values, the subject was alert and making an effort but probably had impaired neurocognitive functions. If the Neurophysiological Cognitive class of measures differed from baseline, an analysis then determines which of the measures differs and their significance. For instance, if the alpha band EEG power was less than baseline, the subject was probably making a greater mental effort to perform the task battery.

It is a further feature of the present invention to provide a method and system to determine the Neurocognitive Function Change score of a subject by measuring the subject's brain waves while the subject performs a task battery that, for instance, engages the basic cognitive functions of sustained attention, divided attention, selective attention, working and intermediate term memory and language comprehension and expression.

It is a further feature of the present invention that the method and system supplies neurophysiological measurements that allow determination of the pharmacological effect of an administered drug on the aforementioned parameters of neurophysiological and cognitive performance, and thus aspects of any drug's pharmacological action on the brain, including the ongoing assessment of such pharmacological action on the brain.

It is a further feature of the present invention that the information about a subject's brain function may be obtained from functional magnetic resonance imaging (fMRI) recordings alone or in combination with EEG recordings.

It is a further feature of the present invention that the information about a subject's brain function may be obtained from magnetoencephalogram (MEG) recordings alone or in combination with EEG and/or fMRI recordings.

BRIEF DESCRIPTION OF THE DRAWINGS

Other objectives and features of the present invention will be apparent from the following detailed description, taken in conjunction with the accompanying drawings. In the drawings:

FIG. 1 is a schematic diagram of the system used in the present invention;

The Combined index used both performance and EEG measures. It was not possible to discriminate caffeine from placebo using just behavioral measures. In contrast, the conditions could be discriminated in each of the four post-drug intervals using EEG measures, or in the first three post-drug intervals using combined EEG and behavioral measures. Results above 0.01 are considered significant. This graph illustrates Experiment 1.

Figure 3:
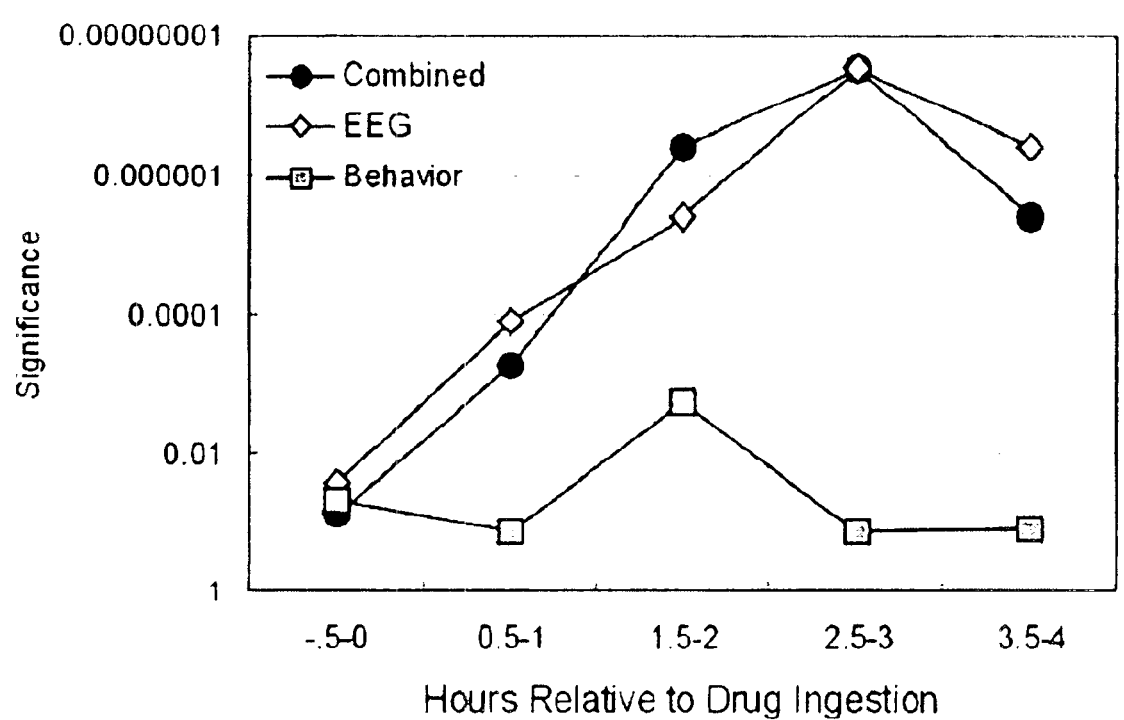

FIG. 3. Binomial significance of the cross-validated classification outcomes of the linear discriminant functions distinguishing data obtained in the alcohol condition from that obtained in the placebo condition, using three types of indices. The Behavioral index used working memory task performance measures, the EEG index used EEG measures recorded during task performance or passive resting states. The Combined index used both performance and EEG measures. Using behavioral measures alone, the two conditions could be discriminated only in the second post treatment interval, occurring 1.5 to 2 hrs post drug ingestion. In contrast, the indices using EEG measures showed significant discrimination between the two conditions in all post treatment intervals. Results above 0.01 are considered significant. This graph illustrates Experiment 1.

Figure 4:
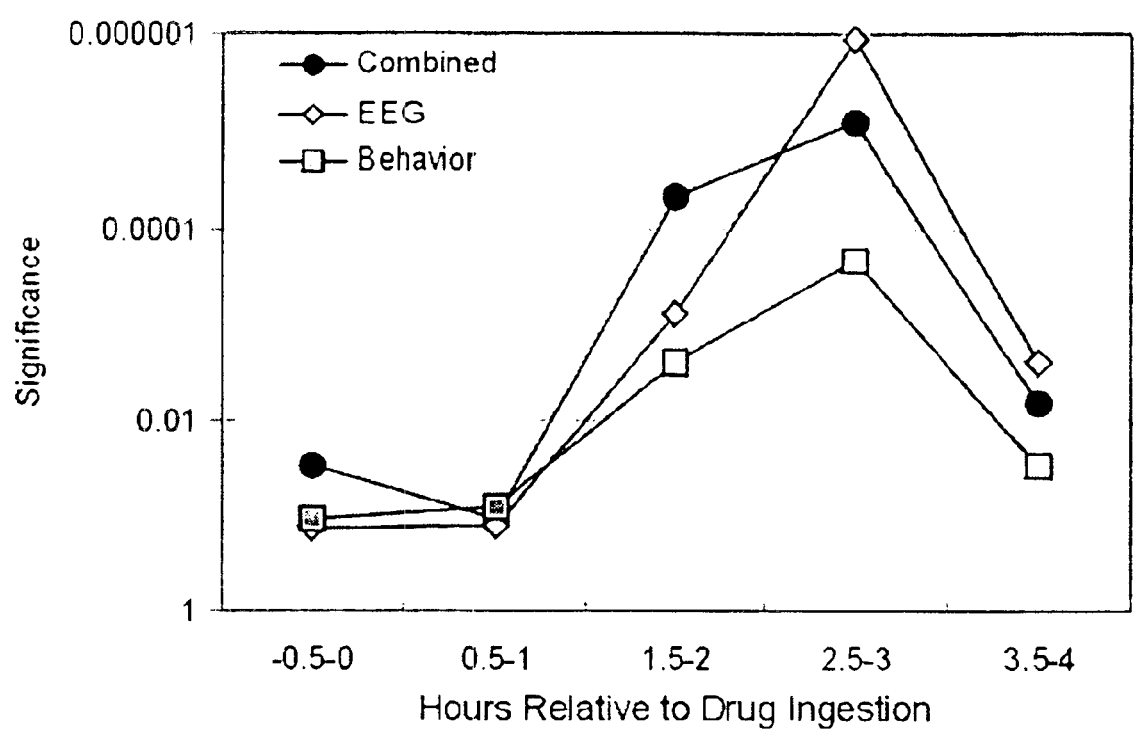

FIG. 4. Binomial significance of the cross-validated classification outcomes of the linear discriminant functions distinguishing data obtained in the diphenhydramine condition from that obtained in the placebo condition, using three types of indices. The Behavioral index used working memory task performance measures, the EEG index used EEG measures recorded during task performance or passive resting states. The Combined index used both performance and EEG measures. Although all three indices showed significant discrimination beginning in the interval 1.5–2 hours post drug ingestion, the Combined index showed the highest level of discrimination at this point. All indices showed peak discrimination in the interval 2.5–3 hours post drug. The EEG and Combined index showed significant discrimination in the final interval (3.5–4 hours post drug) but the Behavioral index did not. Results above 0.01 are considered significant. This graph illustrates Experiment 1.

Figure 5:
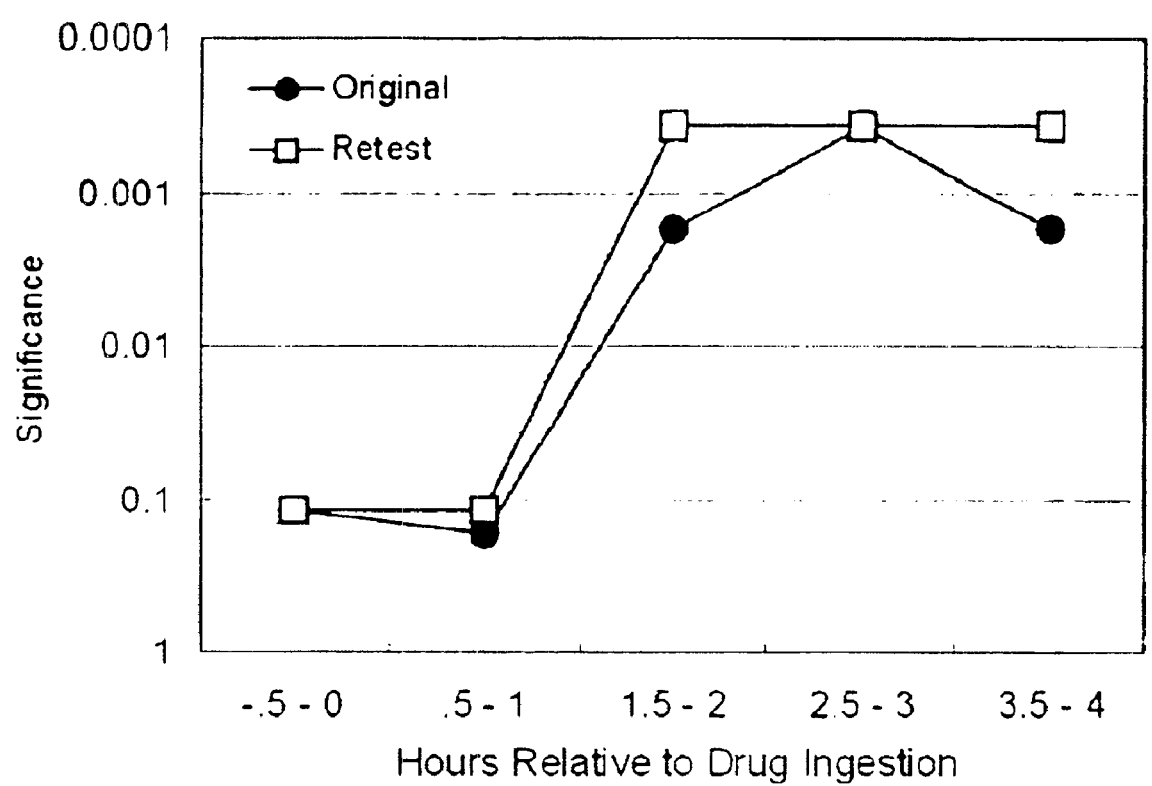

FIG. 5. Binomial significance of the linear discriminant functions discriminating placebo data from the first (original) and second (retest) diphenhydramine treatment conditions, using a Combined Index composed of behavioral and neurophysiological measures. The LDA was performed on the original data for the 11 subjects participating in the retest condition, and then validated by application to the retest data. Results above 0.01 are considered significant. This graph illustrates Experiment 1.

Figure 6:
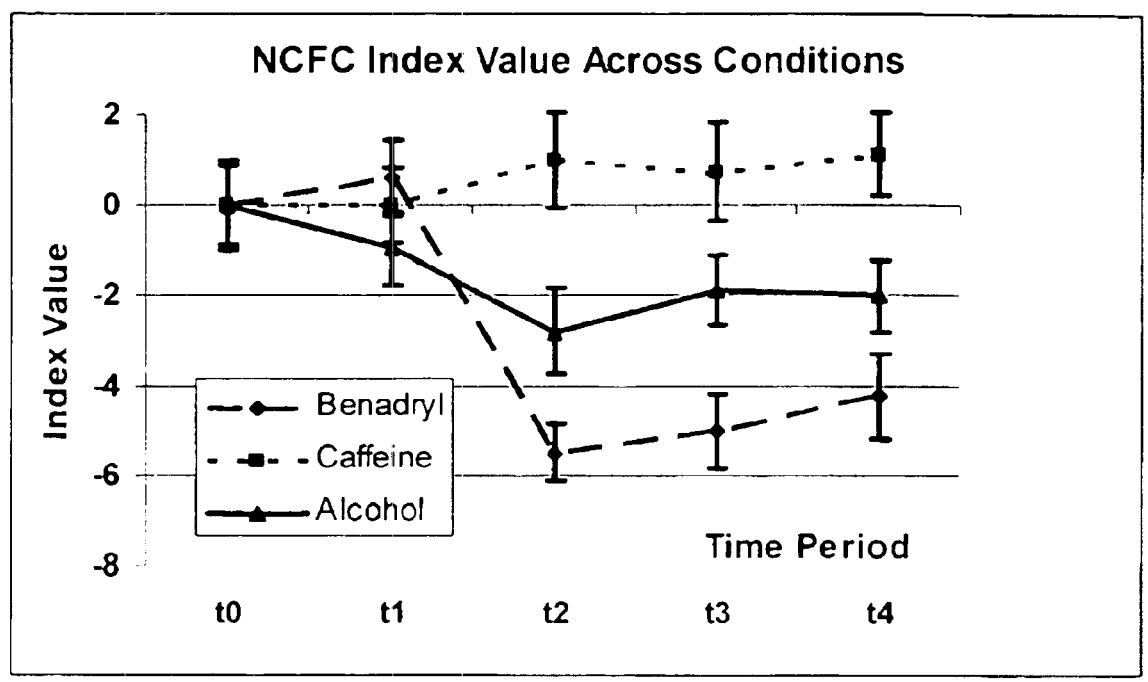

FIG. 6. Mean (+/−SEM) Neurocognitive Function Change index values for a hybrid multivariate index composed of EEG and behavioral measures from (N=16) subjects over five time intervals in Benedryl (diphenhydramine), caffeine, and alcohol test sessions. The NCFC index values reflect direction and degree of change from Baseline, with negative values indicating relative impairment in neurocognitive function. t0 is the reference baseline period before drug ingestion, t1 occurs about 30 minutes after drug ingestion, and the subsequent periods occur at 1.5 hr intervals. This graph illustrates Experiment 2.

Figure 7:
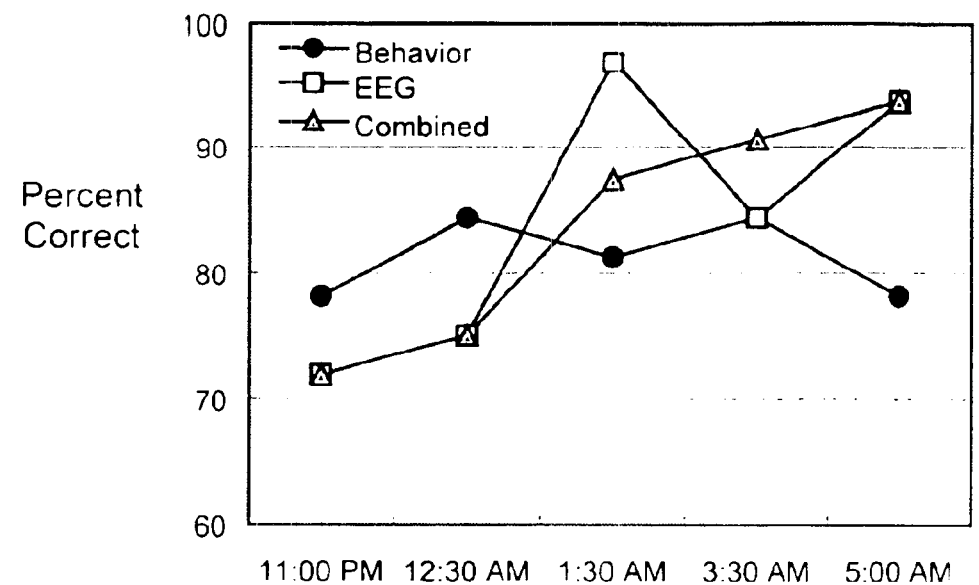
Figure 7:
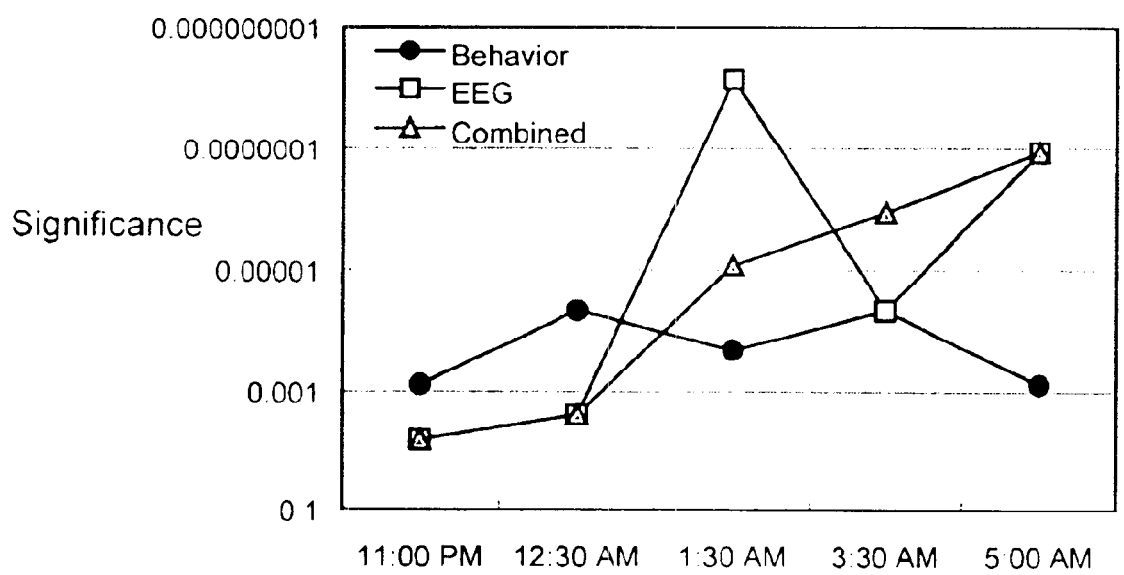

FIG. 7. Percent of subjects' data classified correctly (top) and the corresponding binomial significance level of classification (bottom) for each of the three sub indices. At each interval, the data from the overnight session was discriminated from the data obtained across the four daytime baseline sessions using a linear discriminant analysis. Results show the cross-validation data. The Behavioral index used working memory task performance measures, the Neurophysiological (EEG) index used EEG measures recorded during task performance or passive resting states. The Combined index used both performance and EEG features. By combining EEG and behavioral measures, a monotonic progression is obtained in the portion of subjects classified as sleepy as the night progressed. This graph illustrates Experiment 3.

Figure 8:
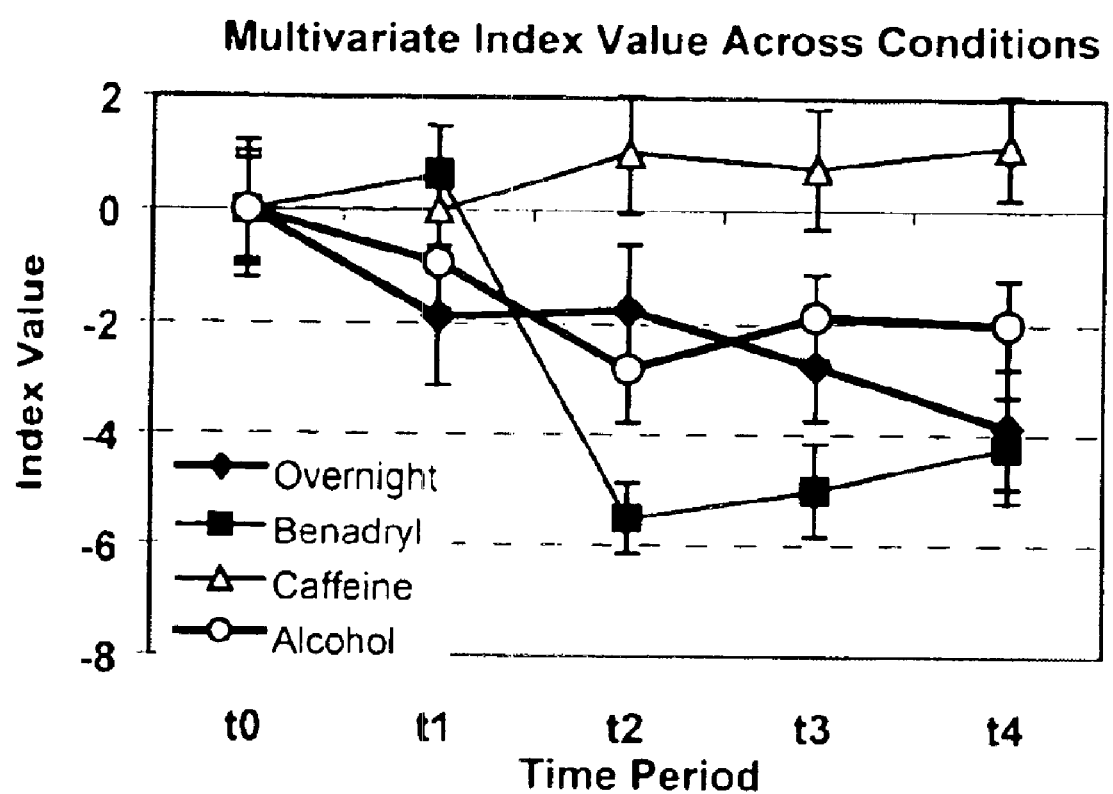

FIG. 8. Mean (+/− SEM) values for the NCFC index values for a hybrid multivariate index composed of EEG and behavioral measures from (N=16) subjects over five time intervals in four separate test sessions. The index values reflect direction and relative degree of change from a baseline interval, with negative values indicating relative impairment in neurocognitive function. For diphenhydramine, alcohol, and caffeine conditions, t0 is the time interval before drug ingestion, t1 occurs about 30 minutes after drug ingestion, and the subsequent intervals occur every 90 minutes. For the overnight condition, t0 is around 11:00pm, and t4 is about 5:00am. This graph illustrates Experiment 3.

Figure 9:
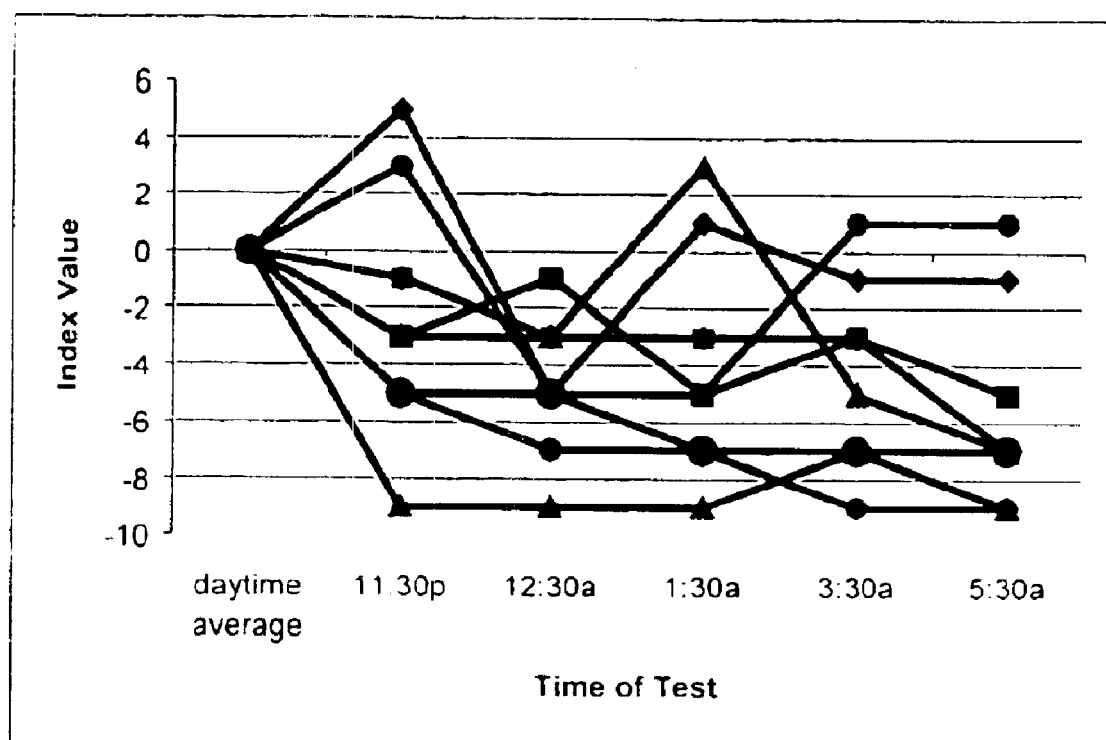

FIG. 9. Subject-specific Neurocognitive Function Change index values for eight individuals from the extended wakefulness test session relative to their average daytime levels. This graph illustrates Experiment 3.

Figure 10:
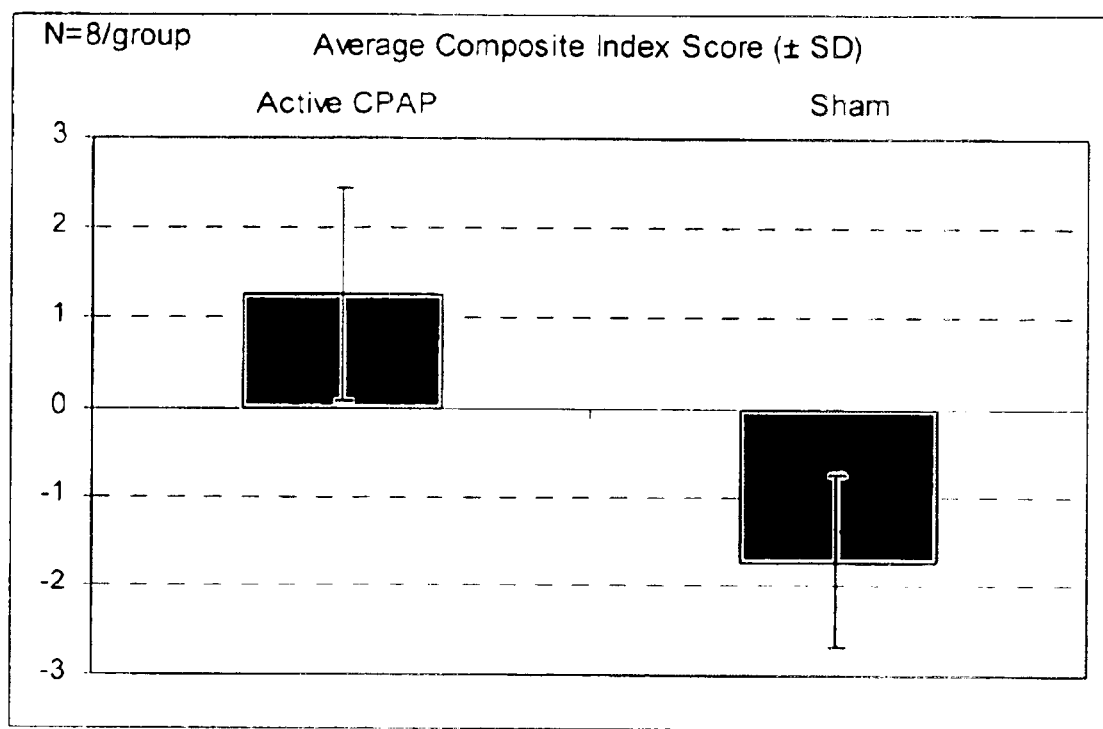

FIG. 10. Neurocognitive Function Change index values for groups of patients (N=8 per group) who either received Active CPAP or Sham CPAP treatment of their obstructive sleep apnea condition. This graph illustrates Experiment 4.

Figure 11:
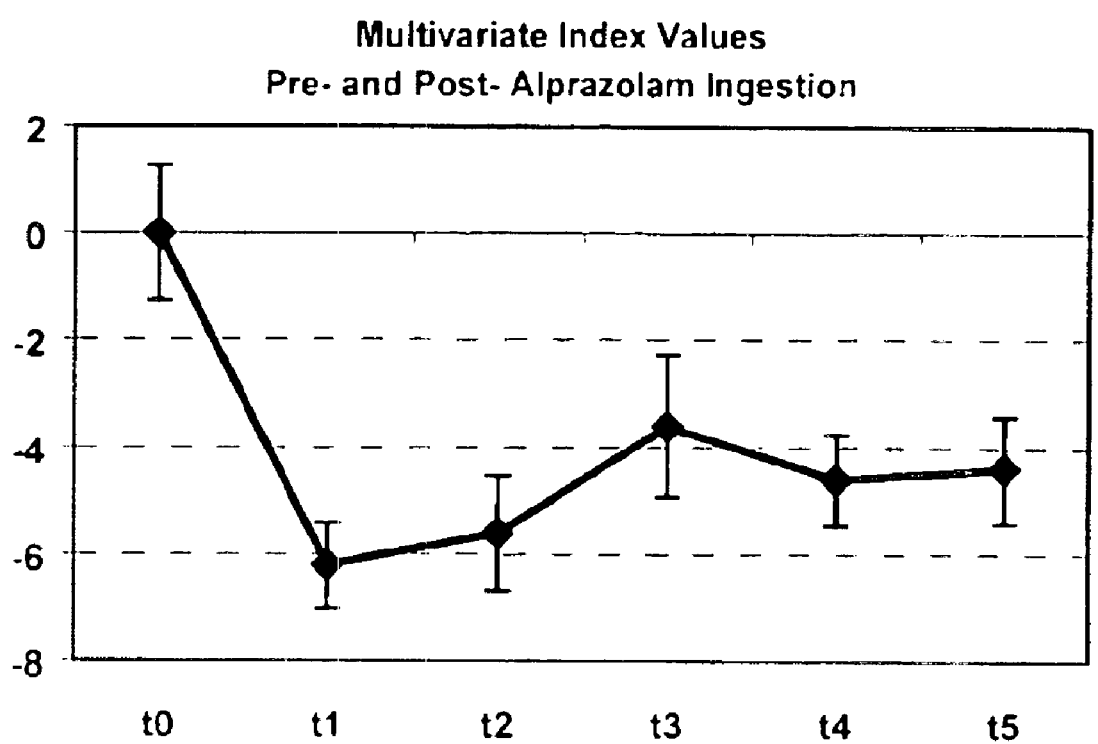

FIG. 11. Mean (+/−SEM) Neurocognitive Function Change index values for a group of patients (N=10) who had received 1 mg. of the anxiolytic medication alprazolam. The index values reflect direction and degree of change from an average response over the placebo and pre-drug (t0) baseline periods. The time period t0 occurred about 1 hr before drug ingestion, t1 occurs about 30 minutes after drug ingestion, and the subsequent periods occur at 1 hr intervals thereafter. This graph illustrates Experiment 5.

Figure 12:
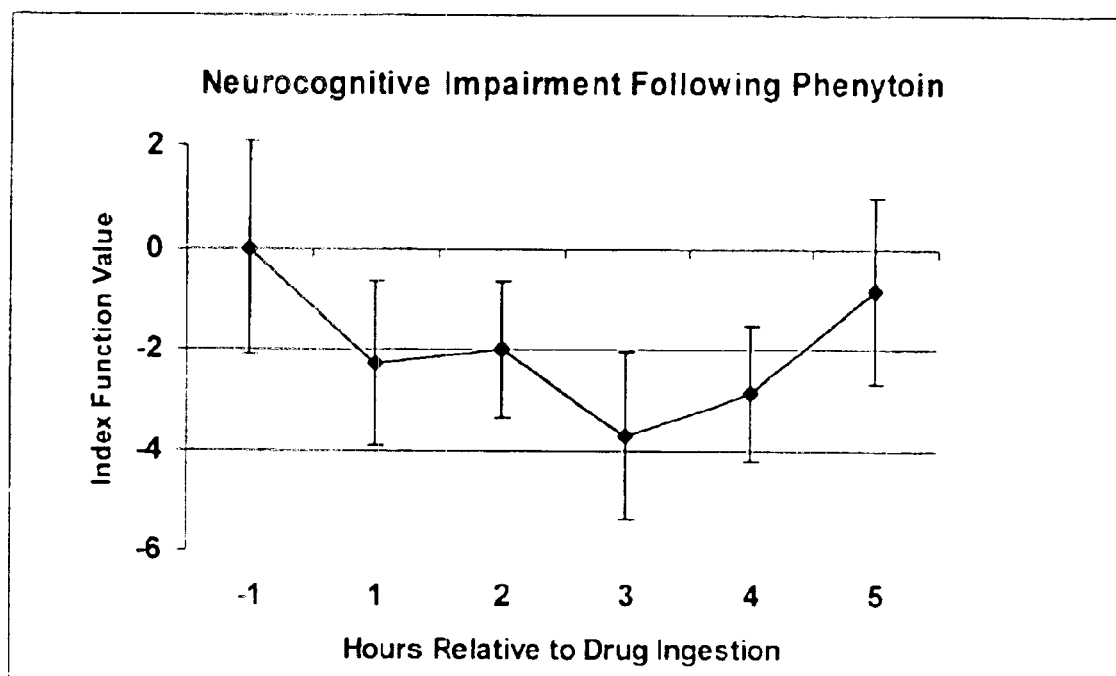

FIG. 12. Mean (+/−SEM) Neurocognitive Function Change index values for a group of patients (N=10) who had received 10 mg/kg bodyweight phenytoin. The index values were computed as deviations from the average of all test sessions for each subject, with negative values indicating impaired function. The resulting index values were then plotted as deviation from the pre-drug baseline at different temporal intervals following drug ingestion. This graph illustrates Experiment 6.

Figure 13:
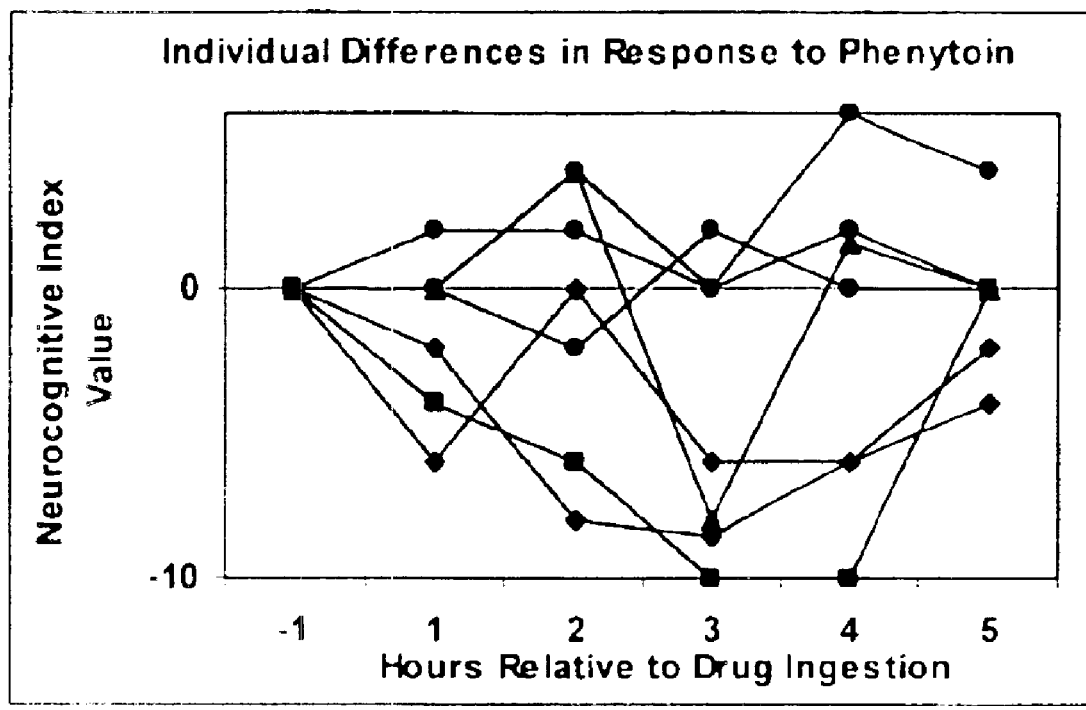

FIG. 13. Mean (+/−SEM) Neurocognitive Function Change index values for each individual from the group of patients (N=7) who had received 10 mg/kg bodyweight phenytoin. As in FIG. 12, the index values were computed as deviations from the average of all test sessions for each subject, with negative values indicating impaired function. The resulting index values were then plotted as deviation from the pre-drug baseline (t=−1 hr). This graph illustrates Experiment 6.

Figure 14:
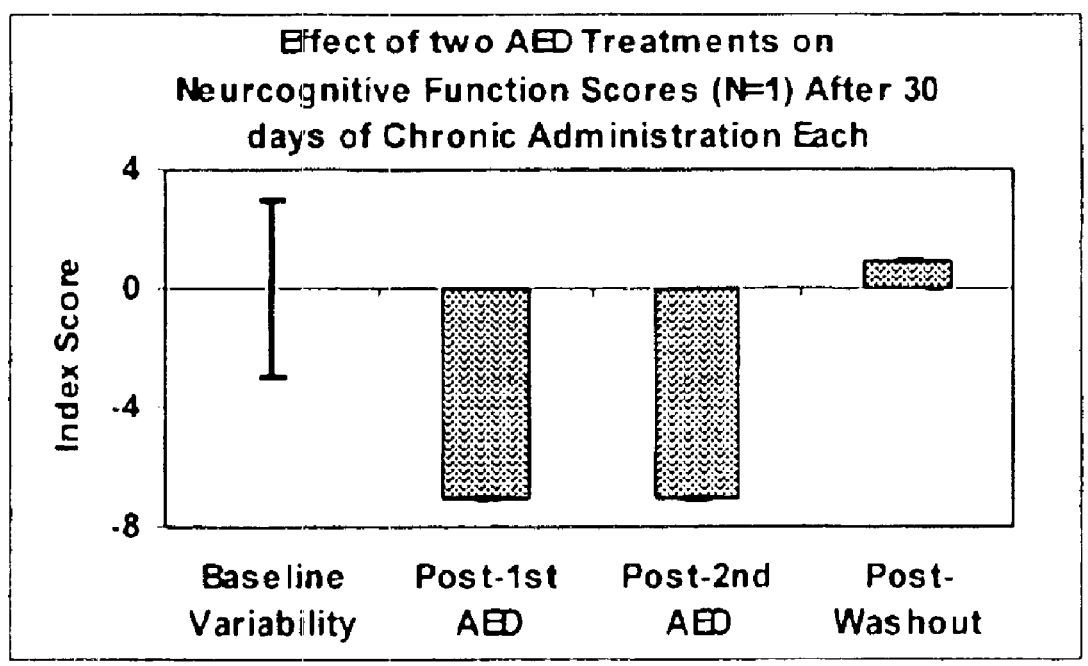

FIG. 14. NCFC scores measured after 30 days of chronic treatment with one anti-epileptic drug (AED) (topiramate or lamotrigine), after a 30 days of treatment with the other AED (after a washout of the first), and after a 30 day final washout period, relative to a pre-treatment baseline test. In this subject, impaired neurocognitive function was observed in response to both drugs. This impairment was alleviated post-treatment following the washout period. Since there was only one baseline measurement in this study, the error bar around the pre-treatment baseline zero-point reflects +/−1 s.d. of normal day-to-day variability as observed in Experiment 1 where normal subjects were measured on multiple days in the absence of a treatment. This graph illustrates Experiment 6.

Figure 15:
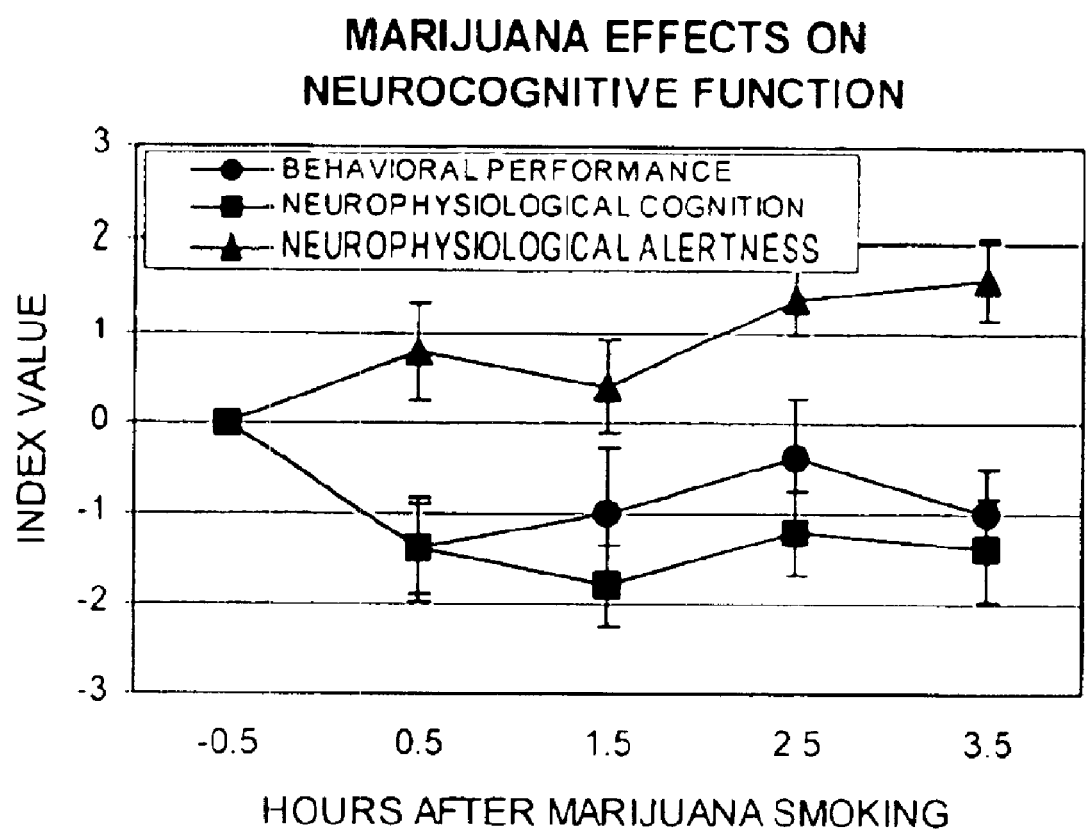

FIG. 15. Mean (+/−SEM) values for the Behavioral Performance, Neurophysiological Cognitive, and Neurophysiological Alertness sub indices of the Neurocognitive Function Change index from a group of healthy subjects (N=10) who had smoked marijuana. The index values were computed as deviations from the pre-smoking baseline, with negative values indicating impaired function. This graph illustrates Experiment 7.

Figure 16:
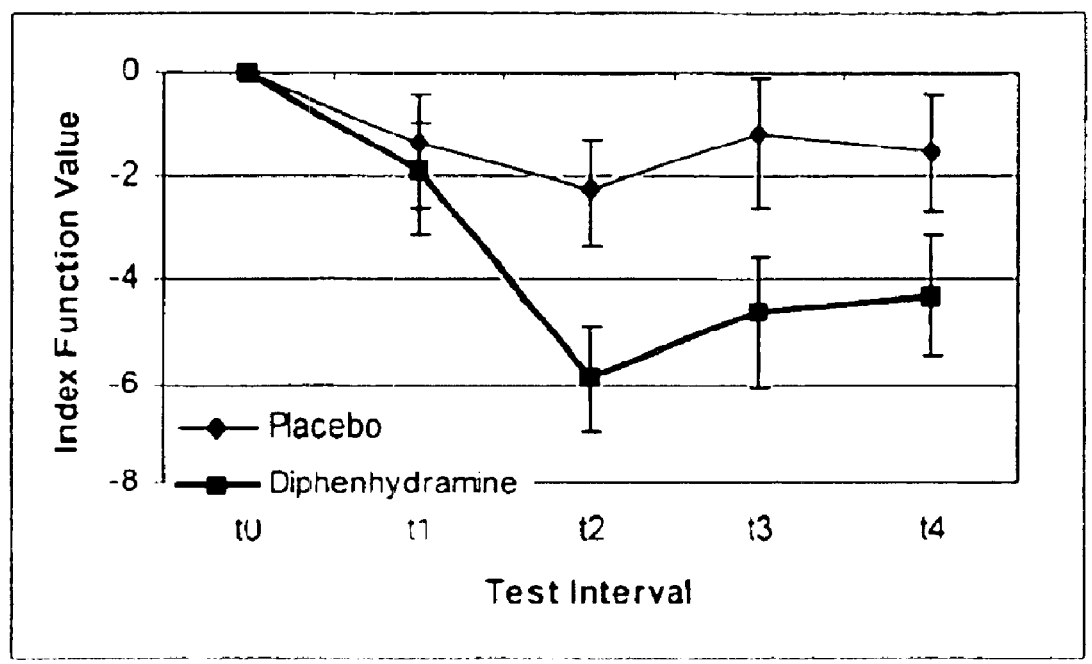

FIG. 16. Mean (+/−SEM) Neurocognitive Function Change index values for a group of elderly patients (N=12) who had received either an inactive placebo or 50 mg of the antihistamine diphenhydramine. The index values were computed as deviations from the pre-drug test interval for each subject, with negative values indicating impaired function. This graph illustrates Experiment 8.

Figure 17:
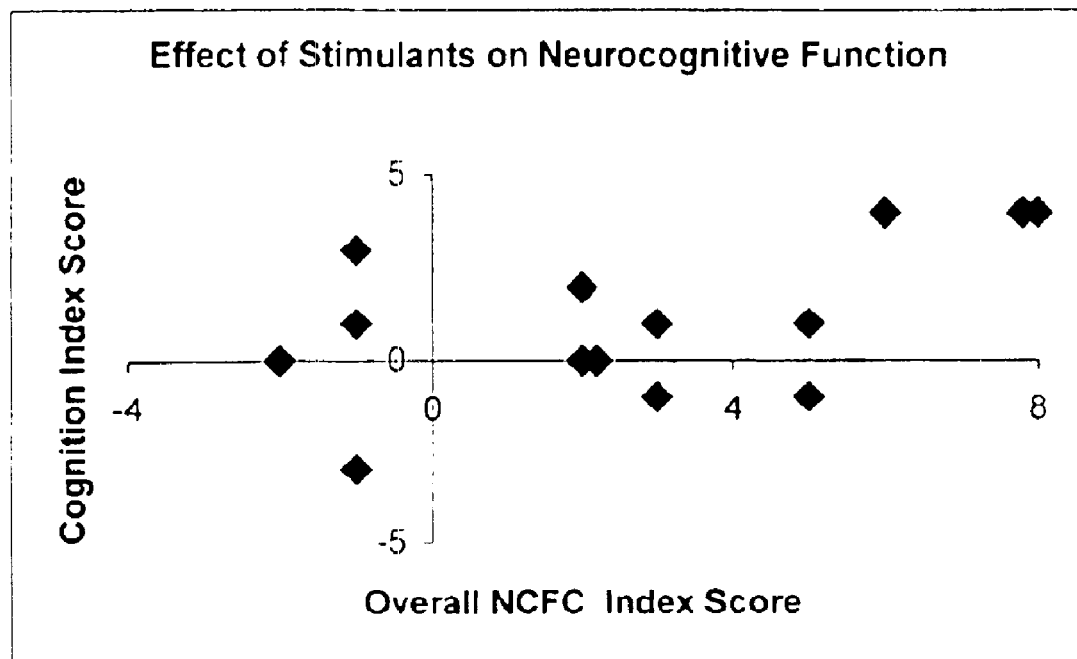

FIG. 17. Effects of stimulant treatment in children with ADHD on the overall multivariate NCFC index and the Neurophysiological Cognition sub index that characterize magnitude and direction of changes in neurocognitive function following an intervention. Each data point reflects an individual patient's change relative to an unmedicated baseline; positive values indicate relative improvement, and negative values relative impairment. This graph illustrates Experiment 9.

DETAILED DESCRIPTION OF THE INVENTION

The present invention is illustrated in FIG. 1. As shown therein, a human subject 10, whose head is illustrated, wears a cloth hat 11, or headset having electrode leads which contact the scalp of the subject. The leads detect the subject's weak analog brain waves and also the electrical activity of his eyes and scalp muscles. A suitable EEG hat is described in the inventor's U.S. Pat. No. 5,038,782, issued Aug. 13, 1991. The hat has preferably 1–32 independent electrodes, although more electrodes may be used. The brain waves are amplified, preferably as described in the U.S. Pat. No. 5,038,782 and artifacts detected and removed, for example, as described in the inventor's U.S. Pat. No. 4,736,751 issued Apr. 12, 1988 and entitled "Brain Wave Source Network Location Scanning Method and System," and as described in the inventor's U.S. Pat. No. 5,513,649 issued May 7, 1996 and entitled "Adaptive Interference Canceler for EEG Movement and Eye Artifacts," all of which are incorporated by reference herein.

Simultaneously with the detection of the subject's brain waves and other physiological signals, the subject is presented with tasks that test fundamental cognitive functions, preferably the functions of sustained focused and divided attention, selective and transient focused attention, preparatory attention, working and intermediate term memory, and receptive and expressive language, for example as described in Gevins and Smith, 2000, in Gevins et al, 1998, 1997, 1996, 1995, in McEvoy, Smith and Gevins, 2000, 1998, and in Smith, McEvoy, and Gevins, 1999. A series of trials of preferably easy and more difficult versions of one or more of the tasks is presented. The task is presented preferably on the screen 13 of a computer monitor, and/or by a loudspeaker 17 connected to the digital computer workstation 14. The subject regards the monitor screen and/or listens to the loudspeaker and responds using a keyboard key 15, or alternatively a switch 12 or a joystick 16. Examples of working and intermediate memory tasks are set forth in detail below. For comparison, the subject's brain waves are also recorded briefly while he or she rests both with eyes open and eyes closed.

Following completion of the task, the task performance and EEG data are analyzed to extract summary measures from the data as described in Gevins, et al., 2002, 1998, 1997, 1996, and Gevins and Smith, 2000, 1999.

A plurality of primary measures are computed from the data, preferably including: 1) the mean, standard deviation and variability of the subject's reaction time to each task trial; 2) the mean, standard deviation and variability of the accuracy of the subject's response to each task trial; 3) the amplitude of the subject's EEG alpha band activity recorded over parietal and prefrontal cerebral cortical brain regions; 4) the amplitude of the subject's EEG frontal midline theta activity; 5) the peak time of the subject's Contingent Negative Variation, N100, P200, P300, N400, P600 and Slow Wave averaged evoked potential peaks elicited by the task stimuli; 6) the peak amplitude of the subject's Contingent Negative Variation, N100, P200, P300, N400, P600 and Slow Wave averaged evoked potential peaks elicited by the task stimuli; 7) the amplitude of the subject's frontal delta power associated with slow horizontal eye movements; 8) the amplitude of the subject's posterior theta and delta powers; 9) ratios of certain primary measures 1–6, for instance theta divided by alpha EEG power, or response accuracy divided by reaction time; 10) ratios of each of primary measures 3–8 between different locations on the scalp; and 11) measures of time series interdependency such as covariance, correlation, coherence or mutual information of primary measures 3, 4, 6 and 8 between different locations on the scalp. Secondary measures are then computed preferably including: 1) differences between or ratios of the primary measures between resting and the easy task version; 2) differences between or ratios of the primary measures between easy and more difficult task versions; 3) differences between or ratios of the primary measures between initial and subsequent repetitions of the task in the same session; and 4) differences between or ratios of secondary measures 1 and 2 between initial and subsequent repetitions of the task in the same session. The primary and secondary measures are then grouped into classes, preferably three classes called Behavioral Performance, Neurophysiological Cognitive, and Neurophysiological Alertness.

The preceding procedure of collecting and analyzing data is repeated over one or more normative groups of subjects recorded while in a baseline state and after one or more drugs or other means or conditions have altered their cognitive functioning. The system provides provide a plurality of ways to specify the Baseline state, including a subject's first recording, a subject's most recent recording, a weighted average of all a subject's prior recordings, a particular prior recording before initiation of a drug or other therapy, a chosen set of prior recordings from a subject, or Baselines previously determined from a normative reference group of subjects with demographic or health characteristics similar to those of a subject being tested.

For each subject within a reference group of normative subjects, rules based on specialized expert neuropsychological and neurophysiological knowledge are then applied to the individual measures within each class of measures. The rules test whether and to what extent each measure differs in an expected manner between each subject's baseline and altered states. For instance, an important Behavioral Performance rule is that performance should be more accurate when a subject is in their baseline state as compared to when they are impaired. Accordingly, this rule returns a negative value when a subject is recorded in an impaired state and their accuracy is lower than in the Baseline state. An example of an important Neurophysiological Alertness rule is based on the fact that a subject's eyes open posterior theta EEG power should be greater when they are drowsy as compared to when they are alert. Accordingly, this rule returns a negative value when their posterior theta EEG power is greater than the value in their Baseline. The outputs of the rules within each class of measures are then weighted and summed, yielding a total output value for the expert rules for that class of measure. An equation is then computed, preferably using a neural network or other type of statistical decision function, that weights and combines the outputs of the classes of expert rules into a Neurocognitive Function Change (NCFC) score that distinguishes baseline from altered states in each normative group of subjects. An example of such an equation is:

$$NCFC = w_1 * \sum_{i=1,m} f_i(x_i t_1 - x_i t_2) + w_2 * \sum_{j=1,n} f_j(y_j t_1 - y_j t_2) + w_3 * \sum_{k=1,p} f_k(z_k t_1 - z_k t_2)$$

where
  NCFC is the Neurocognitive Function Change score,
  $w_{1,2,3}$ are functions that weight the relative importance of the Behavioral Performance, Neurophysiological Cognitive, and Neurophysiological Alertness sub indices to the NCFC,
  $f_i$, $f_j$, $f_k$ are functions that respectively apply expert rules to the component measures and weight the relative importance of the outputs of the rules to Behavioral Performance, Neurophysiological Cognitive, and Neurophysiological Alertness sub indices,
  $x_i$ are component measures to the Behavioral Performance sub index,
  $y_j$ are component measures to the Neurophysiological Cognitive sub index,
  $z_k$ are component measures to the Neurophysiological Alertness sub index,
  m, n, and p are respectively the number of rules and measures in the Behavioral Performance, Neurophysiological Cognitive, and Neurophysiological Alertness sub indices, and
  $t_1, t_2$ are two tests being compared, representing for instance baseline and altered states The NCFC score of a new subject is determined by first measuring her or his behavioral responses and EEG while performing the same task battery in the baseline state and in a subsequent, possibly altered state, then computing the appropriate primary and secondary measures and applying the rules, and finally combining the weighted outputs of the rules according to the equation determined from an appropriate normative reference group.

An analysis is then performed to determine whether a subject's baseline state data are within normal limits by comparing the subject's baseline state to the baseline states of a normative reference group of subjects with similar demographic or health and treatment characteristics.

If a subject's baseline data was accumulated on several occasions, preferably three or more occasions, another analysis determines a normal range of variation of a subject's NCFC score from the set of NCFC scores resulting from comparing the subject's prior baseline states to each other. This comparison is done by computing the appropriate primary and secondary measures, applying the rules, and combining the weighted outputs of the rules according to the equation determined from an appropriate normative reference group.

A typical normal range of variation of the NCFC score for a normative reference group can be determined from the set of normal ranges of the NCFCs of each member of that normative reference group.

It is then determined whether a subject's NCFC score on a particular test day or days represents an altered neurocognitive state by comparing the NCFC score from that day or days with the normal range of variation of the subject's NCFC scores. Alternatively, whether or not a subject's NCFC score represents an altered state can determined by comparing the score with the typical normal range of variation of the NCFC scores of a normative reference group of subjects with similar demographic or health and treatment characteristics.

If a subject's NCFC score on a particular test day or days was determined to represent an altered neurocognitive state, an analysis then determines the manner in which the subject's state was altered by comparing each of the classes of measures from that day or days with their respective values in the baseline. For instance, if Behavioral Performance, Neurophysiological Cognitive, and Neurophysiological Alertness classes all declined from baseline, the subject was probably drowsy. If Neurophysiological Alertness was unchanged, while Behavioral Performance was unchanged or lower and Neurophysiological Cognitive was unchanged or higher than baseline values, the subject was alert and making an effort but probably had impaired neurocognitive functions. If the Neurophysiological Cognitive class of measures differed from baseline, an analysis then determines which of the measures differs and their significance. For instance, if the alpha band EEG power was less than baseline, the subject was probably making a greater mental effort to perform the task battery.

The various data mentioned above are stored in a database as they are collected and computed. Reports generated for each analysis are also stored in the database. A user of the system can examine data in the database either locally or over the Internet.

As an alternative to the EEG recordings, or in addition to the EEG recordings, the information about a subject's brain function is obtained from functional magnetic resonance imaging (fMRI) recordings alone or in combination with EEG recordings.

As an alternative to the EEG or fMRI recordings, or in addition to the EEG and fMRI recordings, the information about a subject's brain function is obtained from magnetoencephalogram (MEG) recordings, alone or in combination with EEG and/or fMRI recordings.

The following description is of an experiment that measured performance and neurological variables of a working memory task when subjects consumed diphenhydramine, caffeine, alcohol, or placebo on separate occasions.

METHOD AND RESULTS OF EXPERIMENT I

Tracking the Cognitive Pharmacodynamics of Psychoactive Substances with Combinations of Behavioral and Neurophysiological Measures Abstract: Many common pharmacological treatments have effects on cognitive ability. Psychometric task batteries used to characterize such effects do not provide direct information about treatment-related changes in brain function. Since overt task performance reflects motivation and effort as well as ability, behavioral measures alone may over- or under-estimate the impact of a pharmacological intervention on brain function. Here we present a method that combines behavioral and neurophysiological measures in order to detect the psychoactive effects of pharmacological treatments with greater sensitivity than that provided by behavioral measures alone. Initial application of the method is made to the data from a double blind, placebo-controlled, crossover study in which caffeine, diphenhydramine, and alcohol were used to alter the mental state of 16 healthy subjects at rest and while they performed low load and high load versions of a working memory task. For each intervention, more sensitive detection of drug or alcohol effects over a four-hour period was obtained when EEG variables were included in multivariate analyses than when only behavioral variables were used. These results suggest that it can be useful to incorporate neurophysiological measures of brain activity into inferences concerning the acute impact of drugs on mental function, and demonstrate the feasibility of using multivariate combinations of behavioral and neurophysiological measures to sensitively characterize the pharmacodynamics of drug-induced changes in cognition.

Background: Many medications affect performance, attention, and alertness; the most common such side effect is sedation. Patients complain of somnolence, drowsiness, inability to concentrate, and diminished energy. On testing, they tend to demonstrate diminished speed and accuracy of psychomotor and cognitive performance. Psychoactive medications may also impair memory, attention, and concentration in the absence of sedative effects. There is a growing literature on the cognitive side effects of treatments for many types of disorders. For example, recent articles have described acute cognitive impairments associated with interferon-α treatment, chemotherapy, antianxiety treatments, and treatment for allergies.

A major problem in determining whether and to what extent drugs produce cognitive effects is that there are no standard effective means for objectively assessing cognitive impairments associated with pharmacological treatments. This lack of a clinical standard has been cited as a major confounding factor in the discrepancies between the results of different clinical trials. In most cases, performance on an ad hoc battery of rating scales and behavioral tests of cognitive and psychomotor functions is employed. Such tests likely vary widely in their sensitivity. A subtler problem with this approach is the fact that behavior is the product of many neural systems, some of which may be recruited or adapted in some way to compensate for deficits. That is, an individual might be able to temporarily mobilize the necessary mental resources to perform a cognitive test even when mildly debilitated, but not be able to maintain such extra effort over the course of a workday. Conversely, a low level of test performance may reflect motivational rather than ability factors. Hence, in isolation, behavior may not provide an accurate picture of the effects of a medication on cognitive brain function.

EEG data can provide assessments of cognitive changes that complement the information provided by self-report and behavioral measures. When other factors are held constant, EEG signals tend to have high test-retest reliability. Despite this stability under normal conditions, EEG signals can be very sensitive to variations in alertness, and/or the amount of effortful attention exerted during task performance. Because of such characteristics, EEG measures have often been used to help characterize the central effects of alcohol, and psychoactive medications.

In the context of such research, a large number of studies have employed multivariate pattern classification techniques, including both linear discriminant analysis and neural network approaches, in efforts to automatically detect and classify patterns of EEG changes associated with pharmacological interventions. This has included efforts to discriminate the effects of different classes of psychoactive drugs (e.g. stimulants, antidepressants, tranquilizers, and neuroleptics) as an aid in the evaluation of new pharmacological agents, to discriminate the effects of different drugs within a class such as different hypnotics used to induce anesthesia, and different benzodiazepines used to promote sleep, and to examine dose-response relationships.

Most such pattern classification studies have been conducted using as input data EEG recorded from subjects that were passively resting or even unconscious. However, recent studies have demonstrated that similar results can be obtained from subjects actively engaged in cognitive task performance. For example, we have used neural network based methods to compare task-related EEG features between alert and mildly intoxicated states, and between alert and drowsy states, in individual subjects. Utilizing EEG features in the alpha and theta bands, an average cross-validation classification accuracy of 98% was obtained across subjects for the alert versus mildly intoxicated comparison (average binomial $p<0.0001$). Similarly, a cross-validation accuracy of 92% (range 84%–100%) was obtained for the alert versus drowsy comparison (average binomial $p<0.001$). This indicates that task-related EEG variables can be used to detect neurofunctional states associated with mild and transient cognitive impairment.

To our knowledge no studies have yet systematically compared the relatively effectiveness of detecting the psychoactive effects of pharmacological interventions using behavioral versus EEG indices of functional status. Similarly, no reported studies have examined the utility of combining behavioral and neurophysiological measures in multivariate classifiers of drug effects, or have asked whether task related EEG measures complement or are redundant with resting EEG measures. By combining behavioral, resting state EEG measures, and task-related EEG measures it might be possible to detect the effect of medication on CNS function with greater sensitivity. The study reported herein examines this possibility. Multivariate pattern classification methods are applied to behavioral and EEG measures in an attempt to detect the acute CNS effects of several common psychoactive substances (caffeine, alcohol, and the antihistamine diphenhydramine) and to characterize their pharmacodynamics over an extended test session.

Experiment Methods: All participation was fully informed and voluntary, and the experiment was conducted under appropriate guidelines for the protection of human subjects. Sixteen healthy adults (21–32 years, mean age 26 years, 8 females) received monetary compensation for participation in the study. All subjects were non-smokers, social drinkers (1–10 drinks per week) and moderate consumers of caffeine (1–4 cups of coffee per day). All subjects had consumed antihistamines at some time in the past, but none were currently taking antihistamines or any other psychoactive medications.

Subjects performed two difficulty levels of a continuous performance, n-back working memory task, versions of which we have employed in many other EEG studies. In this task, subjects were required to compare the spatial location of the current stimulus with that of one presented previously. Briefly, single capital letter stimuli, drawn randomly from a set of twelve, were presented for 200 msec once every 4.5 sec on a computer monitor. At 1.3 sec prior to stimulus onset, a warning cue (a small "x") appeared in the center of the screen for 200 msec. The letter stimulus occurred 1.3 sec after the cue in one of twelve possible locations on the monitor. The identity of the letter and its spatial position varied randomly from trial to trial. A small fixation dot was continuously present at the center of the screen. In a low load version of the task, subjects were required to match the position of the current stimulus with the position of the very first stimulus presented in the block. In a high load version of the task, subjects compared the current stimulus with that presented two trials previously. In this version subjects were required to remember two positions (and their sequential order) for the duration of two trials (nine seconds), and to update that information on each subsequent trial. In both versions of the task, stimuli were presented in blocks of 53 trials (the first three trials were warm-up trials and were discarded from analysis). Matches occurred randomly on 50% of the trials. Subjects were instructed to respond as quickly and as accurately as possible.

Each subject participated in six sessions. The first session was a practice session in which subjects learned to perform the working memory tasks. After training, all subjects participated in 4 sessions, separated by at least one week. These sessions involved recording from subjects after they had ingested alcohol, caffeine, diphenhydramine, or placebo. Eleven of the sixteen subjects returned for an extra session, which was a retest of the diphenhydramine condition. The four drug sessions were conducted according to a double blind, placebo-controlled, randomized, counterbalanced, crossover design. In each session, subjects consumed two pills (unmarked gelatin capsules) and a mixed drink. The pills contained either 50 mg of the antihistamine diphenhydramine (active ingredient in Benadryl), 200-mg of caffeine (equivalent to approximately 2 cups of coffee), or a placebo consisting of powdered sugar. The pills were given with a 500 cc drink containing either 0.88 g/kg 95% ethanol mixed in fruit juice (adequate to produce an average peak blood alcohol content (BAC) of 0.08), or containing 495 cc of fruit juice with 5 cc of alcohol floated on top to mimic the smell and taste of the treatment drink. The diphenhydramine retest condition was also performed in a double-blind manner, with both the subjects and the experimenters unaware of the nature of the test condition being repeated.

Each drug session involved a baseline recording before drug administration. This was followed by four post-drug recording intervals, each lasting approximately 40 minutes. The first interval began 0.5 hrs after drug ingestion; the remaining three intervals occurred hourly thereafter. A scientist not otherwise involved in the experiment administered a Breathalyzer test at the beginning of each interval. Subjects also completed the Karolinska and Stanford sleepiness scales at each test period. Task-related EEG was then recorded while subjects performed two blocks of the low load and high load versions of the working memory task (order of tasks counterbalanced across subjects) and while they rested quietly with their eyes open and closed.

EEG was continuously recorded from 28 scalp electrodes using a digitally linked-mastoids reference. EOG was recorded from electrodes placed above and below one eye, and at the other canthi of each eye. Physiological signals were band-pass filtered at 0.01 to 100 Hz and sampled at 256 Hz. Automated artifact detection was followed by application of adaptive eye contaminant removal filters. The data were then visually inspected and data segments containing possible residual artifacts were eliminated from subsequent analyses. To examine the effects of the pharmacological interventions on individual EEG or behavioral variables, univariate repeated measures analyses of variance (ANOVAs) were used to compare data from each of the three treatment conditions with the placebo condition.

For neurophysiological features, average power was extracted from individual spectral bands at individual electrode sites, and then compared across test conditions. Decisions as to which parameters to extract from the spectra were based on the results of prior studies. For the task related EEG, past studies indicate that the frontal midline theta rhythm and the parietal alpha rhythm are sensitive to variations in the attentional demands of tasks, and, in particular, to the increase in difficulty in the working memory tasks employed here. For the EEG recorded under passive resting conditions, past studies indicate that activity in the delta and theta bands at posterior sites, and the alpha rhythm measured over the occipital region, are highly sensitive to variations in alertness and arousal. Each of the individual features was compared between placebo and each drug condition in univariate ANOVAs with repeated measures.

In a second series of analyses, multivariate methods—stepwise linear discriminant analysis (LDA)—were used to determine whether the various treatments could be discriminated from placebo. In particular, for each treatment condition (caffeine, alcohol, or diphenhydramine), three sets of stepwise LDAs were performed in which the treatment was compared to the placebo in two-class discrimination problems. The three sets of analyses differed in the constellation of independent variables used. In one, task-related behavioral variables were used (Behavior LDA Analysis). In a second, neurophysiological variables recorded during task performance and during passive resting conditions were used (EEG LDA Analysis). The third used both behavioral and EEG variables (Combined LDA Analysis). In all three analyses, discriminant functions were restricted to a maximum of four variables. In each case LDA functions were derived from a set of measures that included both first-order predictor variables (e.g. performance speed or accuracy, EEG power in particular bands, etc.) and second-order, derived predictor variables. The second-order variables included measures such as changes in variables between high load and low load tasks, or between eyes-open and eyes closed resting conditions, or ratios of power in different EEG bands.

For each type of analysis, a two-step process was used to analyze the data from each session. First, data from all the post-treatment intervals were submitted to a stepwise LDA to discriminate between treatment and placebo conditions. The variables (features) chosen in this analysis (restricted to a maximum of four) were then submitted together to an LDA to discriminate treatment from placebo data in each interval (including the baseline interval as a control). The LDAs on the baseline interval and on all four post-treatment intervals were performed using a leave-out-one jack-knife cross-validation approach. In this approach the data from each of the 16 individual subjects was classified using equations that were first derived from the data provided by the other 15 subjects, and then independently applied to the remaining subject. The mean classification accuracy of the 16 such cross-validation analyses was computed and the significance assessed using the binomial probability distribution. A conservative $p<0.01$ criterion was adopted to impute statistical significance to the classification results.

Experiment Results

Subjective Ratings. Following treatment, participants' self-reports on the Karolinska Sleepiness Scale indicated that they felt most alert in the caffeine test condition and least alert during the diphenhydramine test condition. These differences were reflected in a Drug by Recording Interval interaction ($F(12,168)=6.54$; $p<0.001$). Treatment with caffeine did not produce subjective sleepiness ratings significantly different from placebo. This lack of significant change may reflect a floor effect in the well-rested subjects. Treatment with diphenhydramine led to a significant increase in subjective sleepiness relative to placebo at the 2.5–3 hr and 3.5–4 hr post-treatment intervals. Treatment with alcohol, which reached peak BAC=0.08 on average during the first post-treatment interval and which declined steadily to a BAC=0.03 on average by the last post-treatment interval, produced a significant increase in subjective sleepiness relative to placebo at the 1.5–2 hr, 2.5–3 hr and 3.5–4 hr post-treatment intervals. Results with the Stanford Sleepiness Scale were in accordance with these observations.

Behavioral Performance. In all drug conditions, subjects responded faster ($F(1,14)=61.60$; $p<0.001$) and more accurately ($F(1,14)=23.77$; $p<0.001$) in the low load WM task condition than in the high load condition. The pattern of drug-related changes in overt task performance was similar to that observed for the subjective ratings, with significant Treatment by Recording Interval interactions for both RT ($F(12,168)=4.63$; $p<0.001$) and accuracy ($F(12,168)=4.54$; $p<0.001$). No significant behavioral differences were observed when comparing caffeine to placebo. For the alcohol treatment, no significant main effects were observed for either accuracy or reaction time relative to Placebo. Alcohol did have a more subtle effect on reaction times though, producing a treatment by task load interaction whereby reaction times following alcohol were slightly faster in the high load task, and slightly slower in the low load task, relative to responses in the placebo condition ($F(1,14)=11.60$; $p<0.01$). In contrast, after treatment with diphenhydramine subjects performed the both task levels significantly more slowly ($F(4,60)=4.98$; $p<0.001$) and less accurately ($F(4,60)=9.67$; $p<0.001$) than in the placebo condition, with a nadir in the third post-ingestion interval (2.5–3 hours post drug).

Neurophysiological Effects. In the placebo condition and in the pre-treatment baseline test sessions, neurophysiological parameters varied across the different test conditions in a predictable fashion. For example, alpha band EEG measures were attenuated in the eyes-open resting condition relative to the eyes-closed resting conditions. The major differences in EEG parameters between the high load and low load versions of the WM task also replicated past studies. In particular, the frontal midline theta signal reliably increased with increased task difficulty, and the parietal alpha signal was attenuated in the more difficult task.

When compared with the placebo condition, the different pharmacological treatments resulted in distinct changes to neurophysiological parameters. These changes are summarized in Table 1. Caffeine had the least effect on neurophysiological parameters. Caffeine did not produce significant differences in resting EEG data relative to placebo; however it did produce a significant reduction in alpha band power at parietal sites during the performance of both task conditions ($F(4,60)=4.91$; $p<0.01$).

Alcohol had the largest effect on neurophysiological parameters. Alcohol increased the power in the delta ($F(4,56)=3.56$; $p<0.05$) and theta ($F(4,56)=6.73$; $p<0.01$) EEG bands during both resting conditions. During task performance alcohol was associated with an increased in the amplitude of both the frontal midline theta rhythm ($F(4,56)=12.45$; $p<0.01$) and the parietal alpha rhythm ($F(4,56)=14.71$; $p<0.001$) in both high load and low load task conditions. Diphenhydramine had large effects on neurophysiological parameters during resting conditions, but relatively subtle effects on the EEG during task performance. In particular, diphenhydramine was associated with an increase in power in the delta ($F(4,60)=4.37$; $p<0.01$) band during both resting conditions. Power in the theta band also showed a trend towards increasing with diphenhydramine in both resting states ($F(4,60)=2.83$; $p<0.07$). In contrast, diphenhydramine was associated with an attenuation of power in the alpha band in the eyes-closed resting condition ($F(4,60)=6.37$; $p<0.01$), but no significant change in power during the eyes-open resting condition. During task performance diphenhydramine was associated with a reduction in power for the frontal midline theta rhythm in the high load task only ($F(4,60)=3.99$; $p<0.05$). This task-specific reduction in the frontal midline theta rhythm effectively eliminated the difference in frontal midline theta power that was otherwise observed between high load and low load task conditions.

TABLE 1

Direction of significant ($p < .05$) change in spectral power (vs. placebo) for each EEG feature in each treatment condition.

| | | Caffeine | Alcohol | Diphenhydramine |
|---|---|---|---|---|
| Resting EEG Eyes Closed | Pz delta | ■ | ▲ | ▲ |
| | Pz theta | ■ | ▲ | ■ |
| | Oz alpha | ■ | ■ | ▼ |
| Resting EEG Eyes Open | Pz delta | ■ | ▲ | ▲ |
| | Pz theta | ■ | ▲ | ■ |
| | Oz alpha | ■ | ■ | ■ |
| Task EEG Low Load | aFz theta | ■ | ▲ | ■ |
| | Pz alpha | ▼ | ▲ | ■ |
| Task EEG High Load | aFz theta | ■ | ▲ | ▼ |
| | Pz alpha | ▼ | ▲ | ■ |

Figure 2:
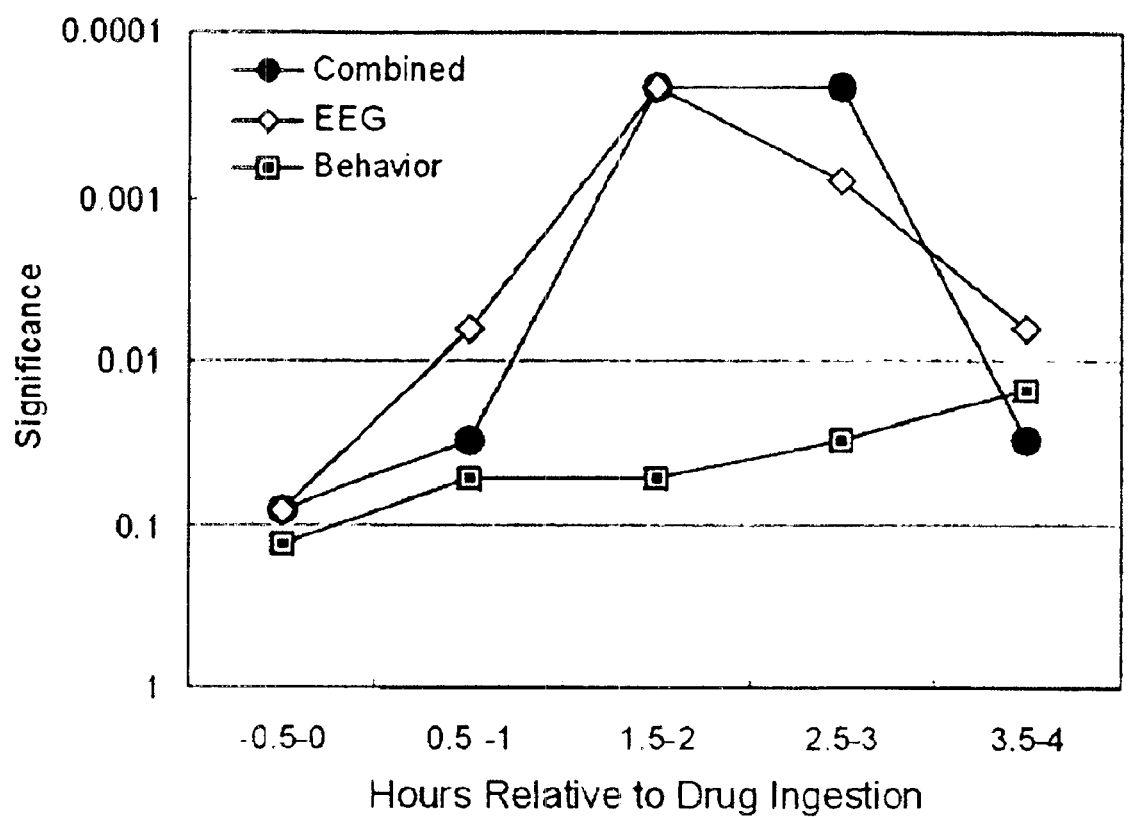
FIG. 2. Binomial significance of the cross-validated classification outcomes of the linear discriminant functions distinguishing data obtained in the caffeine condition from that obtained in the placebo condition, using three types of indices. The Behavioral index used working memory task performance measures, the EEG index used EEG measures recorded during task performance or passive resting states.

Multivariate Detection of Caffeine. The Behavior LDA Analysis did not produce significant discrimination between the caffeine and placebo conditions in any interval. In contrast, the EEG LDA Analysis significantly discriminated caffeine from placebo beginning with the first post drug interval (0.5–1 hr post drug; binomial $p<0.01$). The difference peaked in the second interval (1.5–2 hrs post drug; binomial $p<0.001$), and remained significant throughout the session (FIG. 2). This analysis used a combination of resting and task-related EEG features. It consisted of two resting EEG features (posterior delta power recorded during eyes open and eyes closed states) and two second-order task-related EEG features (the difference in frontal midline theta power between the low load and high load task, and the difference in alpha power between the eyes open resting state and performance of the high load task). At the peak discrimination interval, the highest weights were given to the two resting variables, with slightly greater weight given to the eyes open variable. The frontal midline theta variable received the lowest weight. In the Combined LDA Analysis, significant discrimination occurred in the second (1.5–2 hours) and third (2.5–3 hours) post treatment intervals only (binomial $p<0.001$). This analysis used three of the variables included in the EEG analysis (posterior delta power during the eyes open state, the difference in frontal midline theta power between the low load and high load task, and the difference in alpha power between the resting, eyes open state and performance of the high load task) in addition to a behavioral variable (reaction time variability in the high load task). Again, the highest weight was given to the resting EEG variable, with the task-related frontal midline theta variable receiving the second highest weight, and the task-alpha variable receiving the lowest weight.

Multivariate Detection of Alcohol. The Behavior LDA Analysis produced significant (binomial $p<0.01$) discrimination between the alcohol and placebo conditions in the second (1.5–2 hrs post drug) post-treatment interval only. This analysis used two behavioral features, reaction time variability in the low load level of the task, and a measure of the speed/accuracy tradeoff (reaction time divided by accuracy) in the high load level of the task. At the interval of significant discrimination, both variables were almost equally weighted in the discriminant equation. In contrast, the EEG LDA analysis showed significant discrimination (binomial $p<0.001$) between alcohol and placebo conditions in all post-treatment intervals, with the peak difference occurring 2.5 to 3 hrs post treatment. This analysis used two alpha features in the eyes closed resting state: one recorded over frontal areas and the other recorded over occipital areas. It also used alpha over frontal areas during performance of the low load task, and posterior theta power during performance of the high load task. The highest weight was given to the frontal alpha measures, with the resting alpha receiving the highest weight during the first two post drug intervals and the task alpha receiving the highest weight during the third and fourth post drug intervals. The remaining two measures received equivalent low weightings for all four post drug intervals. The Combined LDA used the same three alpha features as the EEG LDA analyses and also used a behavioral measure: average reaction time divided by reaction time variability in the high load task, although this feature received a very low weight in the equations. The results of the Combined LDA were very similar to those of the EEG LDA (FIG. 3), and the three EEG measures received similar relative weightings as in the EEG LDA.

Multivariate Detection of Diphenhydramine. All three sets of analyses produced significant discrimination between the diphenhydramine and placebo conditions (FIG. 4). The Behavior Analysis used two variables (reaction time variability in the low load task and response accuracy in the high load task; the former received the highest weighting in the equations). Significant classification was only obtained in the second and third post-drug intervals, with peak discrimination occurring in the third post drug interval (binomial $p<0.001$). Discrimination returned towards chance levels in the final post-drug interval (3.5–4 hrs post drug). The EEG Analysis used two second-order task-related EEG variables and two second-order resting EEG variables. The task related variables included the difference in frontal midline theta power between the low load and high load task and the difference in alpha power between the resting, eyes open state and performance of the high load task. The resting EEG variables included the ratio of theta to alpha power over occipital channels in the eyes open state and the equivalent ratio in the eyes closed state. It revealed a similar pattern of discrimination as the Behavior Analysis, although with greater classification accuracy (binomial $p<0.00001$) at the peak interval and with significant discrimination extending through the final post-drug interval (3.5–4 hrs post drug; binomial $p<0.01$). The highest weightings were given to the resting EEG variables, followed by the frontal midline theta feature.

The Combined Analysis used one behavioral feature (reaction time variability in the low load task), two second order task-related EEG features (the difference in frontal midline theta power between the low load and high load task and the difference in alpha power between the resting, eyes open state and performance of the high load task) and one second-order resting EEG variable (the ratio of theta to alpha power over occipital channels in the eyes closed state). It produced better discrimination between diphenhydramine and placebo than did the other two analyses at the second post-drug interval (1.5–2 Hr post drug; binomial $p<0.0001$). This analysis also showed peak discrimination during the third post drug interval (2.5–3 Hr post drug, binomial $p<0.00001$), and significant discrimination during the final interval (3.5–4 hr post drug; binomial $p<0.01$). Again the resting EEG feature received the highest weighting, with the other three features receiving equivalent moderate weights. As with the analysis of the caffeine data, this analysis also resulted in the selection of both EEG and behavioral variables, again suggesting that the two classes of inputs provided complementary rather than redundant information.

Retest Reliability of Diphenhydramine Effects. The eleven subjects who participated in the retest of the diphenhydramine treatment condition experienced similar levels of subjective drowsiness in the retest session as in the first diphenhydramine session. With respect to behavioral performance, subjects also showed similar increases in reaction time and decreases in accuracy in the retest session as in the original diphenhydramine session, with significant performance decrements in the second and third recording interval. EEG variables also showed similar effects between the two test sessions. That is, diphenhydramine was associated with an increase in the incidence of power in the delta and theta EEG bands during both resting conditions, attenuation of power in alpha band in the eyes-closed resting condition, and a relative reduction in power for the frontal midline theta rhythm in the high load task.

Two approaches were used to examine the reliability of the multivariate method for detecting the effects of diphenhydramine. In the first, we attempted to discriminate the data obtained from the original diphenhydramine session from that obtained in the second diphenhydramine session for the 11 subjects who participated in the retest condition. No variables could be found to discriminate between the two data sets, signifying that there were no systematic differences between the retest diphenhydramine data and the original data. In a second analysis, we tested the reliability of the multivariate method for discriminating drug data from placebo data. For this analysis, we first recomputed the Combined Analysis (described above) to discriminate the original diphenhydramine data from the placebo data using only the 11 subjects who participated in both the original and retest sessions. Since there were fewer subjects in this analysis than in the original analysis (n=11 vs. n=16), we restricted the discrimination function to a maximum of three variables. The recomputed index again included both EEG and behavioral variables, and it showed significant discrimination of drug from placebo data beginning at 1.5 hours post drug and lasting until the end of the session, with peak discrimination occurring at 2.5–3 hours post drug. The function obtained on the original data was then used to discriminate the retest data from the placebo data. Similar levels of discrimination were found for the retest data as for the original data (FIG. 5), confirming that the effects of diphenhydramine on EEG and behavioral variables were very similar in the two sessions.

Experiment Discussion: The objective of this study was to determine whether multivariate pattern classification methods applied to combinations of EEG measures and measures of overt task performance could be used to detect the acute CNS effects of common psychoactive substances (caffeine, alcohol, and the antihistamine diphenhydramine) and to characterize their pharmacodynamics over an extended test session. The pharmacological interventions produced changes in behavior and brain function consistent with past studies of their effects. For each treatment, multivariate detection functions could be derived that were sensitive and specific, and the cross-validation strategy indicated that such functions could generalize to data from new subjects. These findings are discussed below.

Changes in task performance following treatment with caffeine, alcohol, or diphenhydramine. The observed effects of the pharmacological treatments on task performance are largely consistent with the findings of past studies. Caffeine increases arousal, reduces fatigue, and, in moderate doses, can speed responses and improve performance on attention tasks. In the current study, subjects performed the tasks slightly faster and more accurately following caffeine ingestion, but this trend was not statistically significant. This lack of a performance enhancing effect of caffeine is not surprising given the test conditions employed here. First, the subjects had been highly practiced on the tasks on several occasions before the point at which the critical data were collected; because of this extensive practice their accuracy and response speed had likely reached asymptotic levels. Second, performance improvements with caffeine ingestion are typically larger in fatigued subjects. In the current study, subjects were well rested at the beginning of the test sessions, and subjective ratings suggest that they did not experience any significant increase in fatigue over the course of the test session in the placebo or caffeine conditions.

Alcohol is a central nervous system depressant. In past studies of the cognitive effects of alcohol it has been observed to slow psychomotor responses and to decrease accuracy in simple vigilance and sustained attention tasks, and to modify response biases in immediate memory and continuous performance tasks. Such effects were most reliably observed at dose levels approximately 20% higher than those used in the current study. At the dose level employed in the current study, alcohol did not significantly reduce accuracy but it did have complex effects on response speed, slowing responses to stimuli in the low load task and speeding them in the high load task. Relatively subtle effects of low doses of alcohol on performance were also found in our prior study that utilized the same tasks employed here.

The antihistamine diphenhydramine has been noted to produce subjective sedation and to impair cognitive function, particularly in tasks that require sustained attention and speeded visual-motor responses. In the current study we found that responses were significantly slower and less accurate following ingestion of diphenhydramine relative to the other test conditions. Of particular interest is the observation that the behavioral impairment produced by 50 mg of diphenhydramine was substantially greater than the behavioral change observed following a dose of alcohol adequate to raise blood alcohol to the level of legal intoxication in many states.

Changes in neurophysiological measures following treatment with caffeine, alcohol, or diphenhydramine. The particular measures of brain electrical activity made in this study were selected based on past studies that have shown them to be sensitive to variations in alertness or attentional effort. For example, past studies have shown that in the EEG recorded under passive resting conditions, drowsiness is associated with an increase in spectral power in the delta band (<4 Hz) and the lower portion (4–6 Hz) of the theta band, and with attenuation of alpha band (8–12 Hz) signals under eyes closed states. Past studies with the tasks employed here have also identified signals that vary systematically with changes in task difficulty and hence the degree of attentional effort demanded for accurate task performance. In particular, such studies have demonstrated that the frontal midline theta (5–7 Hz) rhythm tends to be larger in the high load task condition, whereas the lower portion (8–10 Hz) of the alpha band tends to be attenuated with increased task difficulty.

Because the neurophysiological measures described above are sensitive to variations in alertness or attentional effort, it was anticipated that they might also be affected by the pharmacological treatments that were introduced. The results confirmed this expectation. Caffeine, alcohol, and diphenhydramine each produced a distinct pattern of changes in these variables. Consistent with the data on subjective alertness and with the overt performance results, the neurophysiological measures recorded following treatment with caffeine differed relatively little from those recorded in the placebo condition. In the eyes-closed resting data, caffeine tended to be associated with a decrease in EEG activity in the delta and theta bands, and an increase in EEG activity in the alpha band. While these findings are suggestive of increased alertness, the changes were not statistically reliable across the group of subjects. The only significant change produced by caffeine was a reduction in alpha band activity during task performance, a result suggesting that subjects were somewhat more attentive to task performance than they were under placebo conditions.

In contrast, alcohol produced large significant effects on both the resting and task related EEG. These effects were disproportionate to the relatively subtle behavioral changes it produced. During both resting conditions, the largest alcohol-related changes were an increase in spectral power in the delta and theta bands. While such a change is consistent with a relative decrease in arousal, such an inference must be made with caution given the absence of neurophysiological signs of drowsiness characteristic of passive resting conditions. During both task performance conditions, alcohol was associated with an increase in spectral power for the frontal midline theta rhythm and in the lower portion of the alpha band. Since these changes occurred independently of the task demands placed on the subject, they are unlikely to reflect specific changes in the way that attentional resources were allocated to the tasks. Rather, the general increase in rhythmic EEG activity following alcohol ingestion observed here and in other studies suggests that acute treatment with alcohol changes the intrinsic oscillatory properties of cortical neurons.

Past studies have indicated that diphenhydramine produces changes in EEG signals that are similar to those associated with increased drowsiness. The data from the current experiment are consistent with this view. In particular, during resting conditions treatment with diphenhydramine produced an increase in power in the delta band, a decrease in alpha band power during eyes-closed conditions, and an increase in the incidence of slow eye movement activity. These changes in neurophysiological indicators of drowsiness are consistent with the subjective reports of increased drowsiness following diphenhydramine ingestion, and with the impaired task performance. In contrast to the effects of alcohol, diphenhydramine had relatively subtle and specific effects on the task-related EEG. In particular, diphenhydramine attenuated the increased power for the frontal midline theta rhythm that is otherwise observed in the high load task relative to the low load task. To the extent to which the typical task load-related increase in this signal reflects effortful attention, this task-specific increase suggests that following diphenhydramine administration subjects were unable or unwilling to expend additional mental effort to confront the increase in task demands.

Multivariate Detection of Drug Effects. The LDA analyses performed in the current study established that the types of pharmacologically-induced behavioral and EEG changes described above are robust enough to be detected in most individual subjects. Moreover, for each treatment intervention the sensitivity of the classification function was greatly improved by the inclusion of BEG measures. For caffeine, it was not possible to derive a function capable of discriminating treatment and placebo data at above chance levels during any time period when only behavioral measures were used. In contrast, when EEG and behavioral measures were both included in the LDA, highly significant detection of the caffeine treatment was obtained. Similarly, an LDA restricted to behavioral measures was only able to detect treatment with alcohol at a weakly significant level in one post-treatment interval; with the addition of EEG variables, highly significant classification was achieved in all post-treatment intervals. Even in the case of diphenhydramine, where treatment was found to produce significant response slowing and decreased accuracy relative to the placebo condition, the addition of EEG variables was found to dramatically improve the sensitivity of LDA based classification functions. Together these results provide strong evidence that there is substantial value added by the inclusion of physiological measures of brain function in efforts to sensitively characterize the pharmacodynamics of psychoactive substances.

The results also suggest that there is value to recording the EEG during resting states as well as during active task performance conditions. When considering the treatment effects on univariate neurophysiological parameters, each treatment was found to produce a distinct pattern of changes across the various test conditions. For example, for caffeine EEG parameters most reliably differed from placebo during performance of both low load and high load WM tasks, but not during resting states. For alcohol, EEG parameters reliably differed from placebo during both resting states and performance of both WM task versions. For diphenhydramine, EEG parameters reliably differed from placebo during resting states and selectively during performance of the high load WM task. These different patterns of results indicate that the neurophysiological changes that accompany a particular psychoactive treatment are dependent upon the functional demands placed on the individual being tested. Furthermore, each stepwise LDA analysis performed using neurophysiological measures as input variables yielded classification functions that included combinations of resting and task-related data. This pattern of results implies that measures of changes in EEG variables across levels of functional demand provide particularly sensitive indices of the way in which brain function is affected by pharmacological interventions.

Finally, even though examples of a particular subject's behavior and EEG data were not used in the development of the functions used to classify their data, a high degree of classification accuracy was nonetheless achieved. The successful leave-out-one-subject cross-validation strategy indicated that there was a good deal of commonality across individuals in the characteristic effects of the treatments, and that the classification functions did not just reflect serendipitous fits to the particular training datasets from which they were derived. Furthermore, the successful cross-validation of a combined function derived from the first test day with diphenhydramine accomplished by applying it to the data from the diphenhydramine retest session illustrates the high degree of reliability in neurocognitive responses to the pharmacological treatment.

Conclusions. The results from this study lend themselves to several conclusions. First, whereas behavioral measures are sometimes adequate for detecting the effect of a pharmacological treatment on cognitive function, it is possible to detect such effects with much greater sensitivity with the addition of EEG measures of brain activity. Second, different pharmacological interventions appear to elicit different patterns of EEG changes depending upon whether or not an individual is actively engaged in task performance. As a result, there is also a benefit to classifier performance derived from including samples of both resting and task related EEG data. Third, the behavioral and EEG effects produced by pharmacological interventions appear to be homogenous across individuals and stable within individuals across multiple test sessions. Because of this stability, it is possible that standardized multivariate detectors of EEG and behavioral changes could be used to characterize the cognitive effects of particular pharmacological interventions across time, experiments, and laboratories. Such results provide compelling evidence to suggest that physiological indices add substantial value when assessing the neurocognitive effects of pharmacological interventions. They also suggest that the multivariate procedures used here could be developed into a sensitive test of the psychoactive properties of new drugs, or of existing drugs that have effects that are less well understood than those observed for caffeine, alcohol, and diphenhydramine.

The following is a description of an experiment in which a combined rule-based and neural network method was used to detect changes in neurocognitive function using the data from Experiment 1.

METHOD AND RESULTS OF EXPERIMENT 2

Hybrid Expert-Rule & Neural Network Method that Combines Three Classes of Measures to Detect Changes in Neurocognitive Function In addition to plain neural network and linear statistical approaches (as in Experiment 1), we have developed a new improved method to detect cognitive impairment that combines rule-based decision algorithms and neural networks. In this hybrid approach, multiple if-then rules gleaned from expert knowledge are applied to data to produce many low-level decisions about the direction of a change between two states. These local decisions are made with respect to single data parameters and the output of these rule-based functions serve as the inputs to a combinatorial network that in turn produces a single summary index of the direction and magnitude of change of neurocognitive function from a baseline state to a test state. As with a knowledgeable human expert assessing an ambiguous problem, decisions about the direction and severity of a change are based on consideration of a variety of pieces of diagnostic evidence, no one of which is central to the overall decision. Since no one parameter is central to the output, since the weighting scheme used for decision making does not rely on statistical parameters derived from a narrowly defined subject population, and since any decision made is computed relative to an individual's own personal baseline, it might be expected that such a decision making approach should work well across a variety of conditions that affect neurocognitive function.

To illustrate the effectiveness of this approach, FIG. 6 summarizes the results of applying such a hybrid algorithm to the data from the 16 subjects in Experiment 1. The output from the algorithm is the composite of three sub indices. The Behavioral Performance sub index incorporates measures of psychomotor speed and accuracy during task performance. The Neurophysiological Cognitive sub index incorporates attention-related EEG variables recorded during task performance (e.g. parameters of attention-related ERP components such as P300 and spectral measures of task load-related EEG modulation). The Neurophysiological Alertness sub index incorporates alertness-related physiological variables (e.g. measures of low frequency EEG activity and slow, rolling eye movement activity) recorded during passive resting conditions. The composite Neurocognitive Function Change (NCFC) index provides a summary score indicating direction and degree of change in neurocognitive status from a baseline state. In FIG. 6, each time point reflects change from the pre-medication baseline at t0. The NCFC index values indicate that there was little change from baseline in the caffeine condition. In contrast, following administration of diphenhydramine the index displayed a large drop in value. The low dose of alcohol resulted in a similar, though less extreme, pattern of impairment. At t1 there was no significant difference between the different treatment conditions. However, beginning at t2 the test conditions significantly diverged and remained that way throughout the remaining test periods (p<0.01 or better for each period from t2–t4). In addition to the summary NCFC score presented in FIG. 6, consideration of the output of the sub indices can also provide specific information concerning the manner in which neurocognitive function has changed from baseline. For example, a confusional state unaccompanied by alertness changes might be reflected in a decrease of the Behavioral Performance and Neurophysiological Attention sub indices without significant change in the Neurophysiological Alertness sub index. In the current experiment, alcohol was found to have a relative greater effect on the Neurophysiological Attention sub index, whereas diphenhydramine had its largest impact on the Neurophysiological Alertness sub index.

The following is a description of an experiment in which subjects stayed up all night while they performed a working memory task and other tasks and had their EEG recorded.

METHOD AND RESULTS OF EXPERIMENT 3

Assessing Neurocognitive Effects of Sleep Deprivation

Background: A large number of experiments demonstrate that sleep loss can have an adverse impact on behavioral tests. For example, experiments with military personnel indicate that overall cognitive ability may decline by 30% following one night of simulated sustained operations without sleep, and by more than 50% following a second such sleepless night. The problem of fatigue-related performance impairment is not limited to individuals working in military environments. Anyone experiencing excessive sleepiness during normal waking hours may perform rote activities adequately, yet may be error-prone in unexpected situations that tax attentional capacity. As a result, fatigue is frequently implicated in major workplace accidents. For example, it has been cited as a probable contributing factor in the crash of the Exxon Valdez oil tanker in Alaska, as well as in the catastrophes at the Three Mile Island nuclear power plant in Pennsylvania and the Union Carbide chemical plant in Bhopal, India. Furthermore, the sleep deprivation imposed by shift work scheduling has been noted to be a source of severe performance decrements, and implicated as a probable cause in a number of major aviation and locomotive accidents. Finally, fatigue has been estimated to be a contributing factor in over 50% of fatal truck accidents and 10% of fatal car accidents, with total economic costs reaching tens of billions of dollars annually. Although the exact incidence of fatigue-related accidents is subject to debate, there is little disagreement that the problem is serious and substantive.

Although less dramatic than sleepiness that results in serious accidents, chronic fatigue-related reductions in performance at work or school, and associated psychosocial stress, is more insidious and perhaps more costly to society as a whole. Indeed problem daytime sleepiness affects a large and growing portion of the population, and the National Commission on Sleep Disorders Research has identified it as a major public health. For example, in recent years awareness has grown that many children and adolescents are, for various reasons, chronically sleep-deprived. Such sleep loss tends to be associated with impaired performance on neuropsychological tests and lower levels of scholastic achievement. Equivalent patterns of degraded performance on the job or on controlled tests have been observed in working adults experiencing interruption of normal sleep patterns. The incidence of sleep disruption increases with advanced age, and in older adults it may interfere with routine daily living functions, compromise emotional well-being, enforce a more sedentary and socially-isolated lifestyle than is consistent with good health maintenance, and mask, complicate, or confound early diagnosis and treatment of dementia. Drowsiness is also a debilitating symptom of many sleep disorders including narcolepsy, a problem afflicting as many as 375,000 Americans, obstructive sleep apnea, which has been estimated to affect from 7 to 18 million Americans, and idiopathic hypersomnia. In sum, across the life span, in health and in disease, problem sleepiness appears to have a significant social and personal impact. Although definitive population studies of prevalence are lacking, problem sleepiness has been estimated to affect 5% or more of the U.S. population. There is thus a clear and pressing need for better scientific understanding of the problems associated with compromised alertness as well as for improved methods for diagnosing and remediating them.

In clinical contexts initial evidence that an individual is experiencing problem sleepiness is typically obtained from subjective reports and/or questionnaires. More definitive and objective evidence of compromised alertness can be provided by tests that assess the tendency to fall asleep, such as the Multiple Sleep Latency Test (MSLT) or the Maintenance of Wakefulness Test (MWT). Subjective measures are imprecise and often unreliable, while the objective measures are expensive and time consuming to administer and must be conducted in a specialized sleep lab over a several hour period. The most widely used objective measure, the MSLT, has been questioned on grounds that it measures sleepiness in a setting conducive to sleep, and thus may not be relevant to sleepiness experienced by patients in their normal daily environments. It has also been criticized on grounds that it confounds sleepiness with the learned ability to fall asleep. In response to these issues, the MWT was developed. This test is similar to the MSLT but instead of instructing subjects to sleep, subjects are instructed to remain awake while seated in a darkened room. Although this test has greater face validity than the MSLT in assessing a subject's ability to remain awake, its expense and length of administration restrict its more widespread adoption. Additionally, the ability to remain awake is not the same as the ability to think clearly.

As a more practical alternative to these clinical gold standards, assessment of compromised alertness and fatigue-related diminution of cognitive function in field contexts is typically accomplished through administration of an ad hoc battery of rating scales and behavioral tests. Such measures vary widely in their sensitivity, and hence it becomes difficult to directly compare results across studies. A subtler problem with this type of approach is the fact that behavior is the product of many neural systems, some of which may be recruited or adapted in some way to compensate for deficits. That is, an individual might be able to temporarily mobilize the necessary mental resources to perform a cognitive test even when mildly debilitated, but not be able to maintain this effort over the course of a workday. Conversely, a low level of test performance may reflect motivational rather than ability factors. Hence, behavioral measures, since they do not provide a direct window on the "neurophysiological cost" involved with producing a certain level of performance, may under- or over-estimate a person's capabilities.

A number of electrophysiological methods have also been used to detect sleepiness. For example, eye movements are well known to be sensitive to drowsiness. As measured electrophysiologically with the electro-oculogram (EOG), or directly with video cameras or LED devices, drowsiness can affect blink rate and amplitude and increase the occurrence of slow, rolling, horizontal eye movements. Spectral features of the ongoing electroencephalogram are also highly sensitive to sleepiness and fatigue. For example, in a recent, we used neural network based pattern recognition methods to compare EEG between alert and sleep-deprived states in each of nine individual subjects. Utilizing alpha and theta band EEG features, we obtained an average cross-validation classification accuracy of 92% (average binomial $p<0.001$) for the alert versus sleep-deprived comparison in individual subjects.

Although physiological measures alone may be sensitive to variations in alertness levels, they do not provide direct information about cognitive ability, i.e. an individual's ability to focus and sustain attention to a task, to efficiently assess the importance of environmental events, and to respond quickly and appropriately. Our recent research has focused on developing an assessment approach that succeeds in incorporating such information. In brief, it requires that a subject perform a brief computer-administered test of sustained focused attention and working memory (sustained attention and working memory are fundamental to many higher cognitive activities and performance problems in sleepy people are especially likely to occur in tasks that require sustained attention). EEG is recorded during the performance of this test and automated signal processing mechanisms extract pertinent measures from the physiological and behavioral data streams. These measures are then used to compute combinations of variables that are weighted in such a manner as to be sensitive to changes in neurocognitive function. These parameters include measures of subject's behavioral performance, and EEG measures recorded under both passive resting and task performance conditions. In combination, the different measures provide an index that incorporates information about the subject's level of alertness, his or her performance ability, and whether brain indices of attention and memory have been altered. Both behavioral and EEG measures can provide information about changes in cognition. Behavioral measures provide direct evidence of functional impairment. However, compensatory efforts by subjects might mask real, functionally relevant, treatment-related changes in brain state. As shown in Experiments 1 and 2 above, by combining behavioral and EEG measures it is possible to detect the effects of compromised alertness on cognitive function with greater sensitivity than either modality can provide in isolation.

Methods: As described in Experiment 1, 16 healthy young adult subjects participated in five testing sessions, separated by at least one week. The fifth experimental session was an extended wakefulness manipulation that began in the evening and lasted until 6:00 am the following morning. This extended wakefulness session is the focus of the current experiment. However, since each of the four drug sessions involved a baseline recording prior to drug administration (around 12:00 PM on each day), the average of these alert daytime baseline sessions was used as a comparison point for the data collected in the extended wakefulness session. In the week prior to the extended wakefulness session subjects were required to keep a sleep diary indicating (among other things) the time on each day they went to sleep and the time they awoke. In the overnight, extended wakefulness session, subjects arrived at the laboratory at approximately 8:30 PM, were given a warm-up block of the working memory task and other tasks, and were prepared for the EEG recording. They then participated in five 40-minute recording intervals spaced throughout the night. The first interval occurred on average at 11:00 PM, the second at 12:30 AM, the third at 1:30 AM, the fourth at 3:30 AM and the fifth at 5:00 AM. The internal structure of each interval was the same as that during the daytime baseline sessions. Within each interval, subjects completed the Karolinska Subjective Sleepiness rating scale and had their EEG recorded while performing two blocks of both easy and difficult versions of the working memory task. At each interval, EEG data were also recorded while the subjects rested quietly with their eyes open and closed. In the intervals between recording blocks, subjects performed other repetitive computer tasks to insure continued wakefulness and to help induce mental fatigue. EEG was recorded and analyzed as described in Experiment 1. To examine how individual behavioral and physiological measures varied over the extended test session, univariate repeated measures analyses of variance were used to compare data from the 12:00 PM baseline to data recorded across the different test intervals of the extended wakefulness session. The experiment-related sources of variance in each of the individual measured parameters were assessed in univariate Task (easy versus difficult) or Resting Condition (eyes-open vs. eyes-closed) by Test Interval repeated measures ANOVAs. Changes in mental function related to extended wakefulness would thus be expected to manifest as a main effect of Test Interval or as an interaction involving Test Interval. The Greenhouse-Geisser correction to degrees-of-freedom was employed to correct for any violations of the sphericity assumption in analyses involving repeated measures. In such cases the reported p-values correspond to the corrected degrees-of-freedom.

Results

Sleep Log and Subjective Scale. The sleep diary data indicated that, on average, participants awoke around 8:00 AM the morning of day of the extended wakefulness session, after having obtained about seven hours of sleep. Thus, the test session of the evening at 11:00 PM occurred, on average, after 15 hours of wakefulness, and the final test session at 5:00 AM took place after about 21 hours of wakefulness. Over the prior week subjects reported falling asleep, on average, between 12:30 and 1:00 AM, and receiving about seven hours of sleep each night. Subjectively, subjects reported that they felt most alert in the 12:00 PM baseline interval, and progressively less alert at later test intervals with minimal alertness usually reached during the final test at about 5:00 AM. This change was reflected in a significant main effect of Test Interval ($F(5,75)=23.31$; $p<0.001$). Post hoc pair wise comparisons indicated that there was no significant difference between the 11:00 PM interval and the 12:00 PM baseline. However, a significant increase in sleepiness was obtained when comparing each subsequent interval to either the baseline or the 11:00 PM intervals ($p<0.005$ for all comparisons).

Neurophysiological Alertness. To provide convergent evidence that the extended wakefulness manipulation had a significant impact on the subjects' level of alertness, eye movement activity and EEG spectra recorded while subjects rested quietly were analyzed for classical signs of sleepiness. Slow eye movements (SEMs) increased over test intervals in the eyes-open resting condition ($F(5,75)=10.52$; $p<0.001$). As with the subjective ratings, at the 11:00 PM session SEM activity did not differ from the 12:00 PM baseline. However, SEM activity had begun to significantly increase by the 12:30 AM test session, and reached a maximum by 5:00 AM when subjective sleepiness also was greatest. EEG spectral power in the delta and theta bands during eyes-closed resting conditions increased over the course of the extended wakefulness session, whereas alpha band power decreased. A Resting Condition (Eyes Closed, Eyes Open) by Test Interval repeated measures ANOVA performed on delta power showed a significant difference between resting conditions, with less delta occurring in the eyes-open condition than in the eyes-closed condition ($F(1,15)=25.9$, $p<0.001$). A significant effect of Test Interval was also obtained, with an increase in delta power in the late night testing sessions ($F(5,75)=3.87$, $p=0.01$). An equivalent pattern of results was obtained for the posterior theta band measure, with less theta band power in the eyes-open condition than in the eyes closed condition ($F(1,15)=64.01$, $p<0.001$), and an overall increase in theta band power over the course of the night ($F(5,75)=4.3$, $p=0.01$). Occipital alpha power displayed a more complex response pattern than that observed for the lower frequency bands. During the earlier test intervals greater alpha power occurred in eyes-closed condition than in the eyes-open condition, whereas the opposite was true during the later test intervals. At the 1:30 AM test interval alpha power was approximately equal in the two conditions. The cross-over interaction was significant ($F(5,75)=4.61$ $p<0.01$). This effect was caused by a significant decrease in alpha power in the eyes closed condition across the night, whereas alpha power in the eyes open condition did not change much over test intervals.

Behavioral Performance. Across test intervals subjects responded more accurately ($F(1,15)=38.22$; $p<0.001$) and faster ($F(1,15)=53.58$; $p<0.001$) in the low load task than in the high load task. These effects of task load did not interact with test interval. Accuracy was around 15% lower late at night than during the 12:00 PM baseline ($F(5,75)=4.90$; $p<0.02$), and reaction times were slowed on average by about 100 msec ($F(5,75)=6.53$; $p<0.001$). Independently of the overall slowing, reaction times also became relatively more variable over test intervals ($F(5,75)=4.28$, $p<0.007$). There were no significant interactions between task load and interval for accuracy, reaction time, or reaction time variability measures. Across tasks, neither accuracy, nor average reaction time or reaction time variability significantly differed between the 12:00 PM baseline and the 11:00 PM test interval. Marginal impairment in performance could be observed by the 12:30 AM test interval, and performance reached a nadir by the 1:30 AM test interval. That is, performance in both the low and high memory load tasks had become significantly impaired by a relatively early stage of the extended wakefulness session. Performance remained at that degraded level through the remaining test intervals, with no further decrement between 1:30 AM and 5:00 AM.

Neurophysiological Cognitive. In order to minimize differences due to general sleepiness-related changes in the EEG and instead focus on changes in the tonic mental effort allocated towards task performance, measurements of task related EEG were computed as difference scores from corresponding measurements made in the eye-open resting condition. Spectral power of the task related EEG was significantly modulated by variations in working memory load. The frontal midline theta rhythm was higher in the high load task than in the low load task ($F(1,15)=7.08$, $p<0.02$). In contrast, increasing working memory load was also associated with attenuation of alpha band power ($F(1,15)=40.78$, $p<0.0001$) atparietal sites. Neither of these signals showed a significant effect of test interval or a significant test interval by task load interaction ($p$'s$>0.1$). This implies that despite an increase in sleepiness over the night, subjects continued to make a mental effort to sustain attention to task performance.

Several components of the ERP response in the current study appeared to be associated with attention and decision making in that they varied systematically between correctly classified matching versus non-matching stimuli and/or between task loads. These components included: 1) an N100 recorded over parieto-occipital regions; 2) a central P200; 3) a P300; and 4) a positive slow wave (SW) recorded over central and parietal regions. To quantify these phenomena, ERP component peak latencies were measured with respect to the time of stimulus onset, and amplitudes were measured with respect to the average amplitude 200 msec pre-stimulus onset. The peak latency of the N100 as measured at lateral parieto-occipital electrode P8 did not significantly differ as a function of stimulus type (match or no match) or working memory load. Latency did, however, increase over test intervals ($F(5,75)=7.46$, $p<0.001$), with a total increase of about 10 msec between the 12:00 PM baseline measure and the 5:00 AM test interval. Post hoc comparisons indicated that this latency increase first reached significance ($p<0.01$) at the 1:30am test interval, with no significant further increases in latency beyond that time. Amplitude of the N100 was related to both task manipulations and time of testing. In particular, across test intervals amplitude of the N100 was larger in the low load task ($F(1,15)=5.20$, $p<0.04$), and larger to match stimuli than to non-match stimuli ($F(1,15)=4.68$, $p<0.05$). There was also a significant task load by stimulus type interaction ($F(1,15)=11.07$, $p<0.005$). Post hoc comparisons indicated that there was no difference in N100 amplitude between the two task types for non-match stimuli. In contrast, the N100 to match stimuli was much larger in amplitude in the low load task than in the high load task ($p<0.01$). Finally, across conditions N100 amplitude was attenuated over test intervals ($F(5,75)=6.33$, $p<0.001$), but this overall attenuation did not interact with stimulus type or task load factors. Post hoc analyses revealed that by the 1:30 AM test interval amplitude of the N100 had been significantly ($p<0.01$) attenuated in comparison to the 12:00 PM baseline. This attenuation in amplitude persisted at approximately the same level throughout the remaining test intervals, and it did not interact with the other factors. Peak latency of the P200 at central midline electrode Cz did not vary as a function of task load or of test interval. Peak amplitude of the P200 varied with test interval ($F(5,75)=4.09$, $p<0.01$), such that relative to the 12:00 PM baseline there was a significant (p<0.01) reduction in P215 amplitude by the 1:30 am test interval. As with the N100, this attenuation in amplitude persisted throughout the remainder of the session, but it displayed a trend towards recovery at the 3:30 and 5:00 AM test intervals. Peak latency of P300 at parietal midline electrode Pz did not differ as a function of task load or of test interval. P300 amplitude varied as a function of test interval (F(5,75)=5.58, p<0.04). As with the N100 and P200, post hoc analyses revealed that by the 1:30am test interval P300 amplitude was significantly (p<0.01) attenuated in comparison to the 12:00 PM baseline. This attenuation in amplitude persisted at approximately the same level throughout the remaining test intervals. The effect of test interval did not interact with the task load or stimulus type factor. Finally, the positive Slow Wave component occurring around 500–600 msec following stimulus onset did not vary as a function of task load or test interval, or any interaction of test interval with the other factors (each F<1).

Multivariate Analysis. To automatically detect changes in cognitive function associated with compromised alertness from extended wakefulness, Stepwise Linear Discriminant Analyses (SLDAs) were performed in which functions were developed to discriminate the 5:00am testing interval from the average of daytime pre-drug baseline intervals, and the resulting equations were then applied to data from the intervening intervals. Preliminary analyses indicated that either behavioral or EEG variables alone were adequate for accurately categorizing data sets as coming from subjects who were very alert or very sleepy. When both behavioral measures and neurophysiological measures from both resting conditions and task performance conditions were submitted to SLDA, the results indicated that a very regular progression in the number of subjects classified as drowsy as the night progressed. FIG. 7 illustrates these results. During the daytime session, 15 of the 16 subjects were classified as alert, as were 14 of the 16 subjects at the first night time test interval at 11:00 pm. In contrast, by the 5:00 am test interval only two of the 16 subjects were still classified as being alert (binomial significance of classification frequencies at the daytime and 5:00 am test intervals were both p<0.001). Thus, these data provide evidence for assessing variations in attention and alertness using multivariate combinations of EEG and behavioral measures.

While a linear statistical approach such as SLDA is suitable for analyzing the group data from a particular experiment, it does not provide a general-purpose index of subject-specific cognitive change that could be applied across test conditions and diverse subject groups. For example, the function used to discriminate the effects of sleep deprivation across a group of subjects would not be expected to effectively discriminate the effects of a drug from a placebo unless the drug happened to have the same effect on the EEG and/or behavior as sleep deprivation. Similarly, although single-subject pattern recognition functions can be very effective at detecting conditions they are trained to detect, they are also unlikely to generalize well to conditions that differ substantively from those included in the training data. Furthermore, statistical multivariate classification methods by themselves do not directly indicate whether a change in state represents a net impairment or a net improvement. Such inferences of relative impairment or improvement require expert knowledge about the individual measures included in the model, or about other convergent information that indirectly imputes directionality. As described in Experiment 2, we have developed a hybrid method that circumvents these limitations by combining expert-rules with statistical pattern classification algorithms.

To illustrate the effectiveness of this approach, FIG. 8 provides a summary of the results of applying such a hybrid algorithm to the data from the 16 subjects in Experiments 1 and 3 in each of the experimental conditions. For the drug conditions, each time point reflects change from the analogous time in the placebo condition, with t0 being the pre-drug baseline. For the overnight (fatigue) data, each time point represents a comparison with the average of the four drug-day t0 values. For the fatigue condition t0 occurs at the start of the overnight recording session. The results suggest that subjects who remained awake overnight suffered from a steady decrease in neurocognitive function as the night progressed. Along with the results of Experiment 2, these results indicate that it is possible to implement a general purpose multivariate index function that combines EEG and behavioral performance measures in a manner that permits direct inference as to whether a positive or a negative change in neurocognitive function has occurred relative to an individual's own baseline state.

FIG. 9 illustrates the range of results obtained for individual subjects in the experiment during the extended wakefulness session (data from only half the subjects are presented to improve legibility). In contrast to the approximation to a monotonic decrease in cognitive function portrayed by the mean results depicted in FIG. 8, a wide range of individual variability becomes obvious. For example, while most subjects display a decline by the 11:30pm session relative to their average daytime index value, some subjects appear to actually be more alert and attentive at this test period. Similarly, while the majority of the subjects appear impaired at the latest test session, some subjects display an improvement relative to their late night test sessions. These results suggest that this approach could be a useful tool for assessing individual differences in circadian rhythms and sensitivity to sleep loss, as well as the implications of such differences for alertness, attention, and performance.

In sum, in Experiments 1–3, we have compiled a substantial body of evidence suggesting that our approach of measuring variations in neurocognitive function using multivariate combinations of behavioral and EEG measures is a highly sensitive one and that it can generalize to a relatively wide range of interventions.

The following is a description of an experiment in which patients receiving treatment for obstructive sleep apnea were tested before and after treatment with our method and system for measuring changes in neurocognitive function.

METHOD AND RESULTS OF EXPERIMENT 4

Neurocognitive Effects of Continuous Positive Airway Pressure Therapy for Treatment of Sleep Apnea Methods: This collaborative study was a randomized, double-blinded, placebo-controlled trial of nasal continuous positive airway pressure (CPAP) therapy for treating obstructive sleep apnea syndrome (OSAS). It was performed in collaboration with Drs. W. Dement and C. Kushida at the Stanford Sleep Disorders Clinic and Research Center. The goal of this pilot study was to determine whether CPAP therapy has a beneficial effect on patients' cognitive abilities. Patients are tested on a battery of cognitive tests, mood and sleepiness scales, and an objective measure of sleepiness, the Maintenance of Wakefulness Test (MWT), before and one month after beginning therapeutic or sub therapeutic (placebo) CPAP treatment. The Stanford University Panel on Human Subjects in Medical Research approved human subjects involvement in this study. The cognitive task battery included our working memory task with concomitant EEG recordings, and a variety of other popular cognitive tests used in clinical neuropsychological research including the Psychomotor Vigilance Task. Sixteen patients diagnosed with sleep apnea participated in the study. Patients were randomly assigned to therapeutic or sub therapeutic (placebo) treatment groups. Patients and experimenters working with the patients were blind to treatment group. The two groups did not differ in age, body mass index, (BMI), or other factors related to the sleep disorder such as respiratory disturbance index (RDI—the number of abnormal respiratory events per hour of sleep), or the minimum oxygen saturation (Min O2) during the sleep study. After obtaining informed consent, patients were taught to perform the cognitive tasks, typically on the evening before the first test day. Univariate analyses were performing using repeated measures analyses of variance with session (baseline, post-treatment) as a within subject factor and Treatment as a grouping factor. Differences due to Treatment were expected to manifest as significant Treatment by Session interactions.

Results:

MWT, subjective and behavioral performance. The Multiple Waking Test showed a significant effect of Treatment, as evidenced by the significant Session by Treatment Group interaction ($F(1,14)=64.42$; $p<0.001$). The average sleep latency for the Active CPAP group improved from an average of 7.9 minutes to 17.5 minutes. In contrast, the placebo treatment group did not show significant change between sessions (8 minutes versus 6.3 minutes). For both Treatment Groups there was a significant main effect of Test Interval ($F(3, 42)=3.26$; $p<0.05$), with the shortest sleep latency occurring at the 2:00PM test interval. SSS). The scores on the Stanford Sleepiness Scale (SSS) indicated that subjects did not perceive a decrease in sleepiness as a function of treatment. The average decrease in subjective sleepiness as a function of treatment was 0.5 (on a 7-point scale) points for both groups. There was no significant Treatment Group or Treatment Group by Session effects (Fs<1). There was a significant effect of working memory task memory load ($F(1,14)=17.07$; $p=0.001$), with subjects performing more accurately in the low load task than in the high load task (98%±0.74 versus 94%±1.24). There was a significant effect of test interval ($F(2,28)=5.09$; $p<0.02$), with subjects performing less accurately during the 2:30 PM interval than during the 11:30AM or 4:30 PM intervals (94.6±1.31 versus 96.6±0.66, 96.5±0.86, respectively). There was no overall difference between treatment groups in accuracy ($F(1,14)=1.768$; $P>0.1$), nor did Treatment Group interact with any of the other factors. There was a significant effect of memory load on reaction time ($F(1,14)=64.04$; $p<0.001$), with subjects responding more quickly in the low load task than in the high load task (686±27 versus 941±58). There was a significant effect of test interval ($F(2,28)=11.0$; $p=0.001$), with subjects responding more quickly during the 4:30 PM interval than during the earlier intervals (by an average of about 50 ms). There was no overall difference between treatment groups in reaction time ($F(1,14)=1.48$; $p>0.1$), nor did Treatment Group interact with Session. Several Psychomotor Vigilance Task measures were assessed including mean reaction time (log transformed), reaction time variability (standard deviation), number of lapses (defined as reaction times longer than 500 msec), median reaction time, slowest 10% of responses, fastest 10% of responses. None of these measures showed any significant Group or Treatment effects.

Neurophysiological Alertness. Slow eye movements in the resting, eyes closed condition were smaller following treatment in the active group and larger following treatment in the sham group, resulting in a significant Treatment Group by Session interaction ($F(1,14)=4.77$; $p<0.05$). Within the active treatment group, paired sample t-tests did not show significant differences between pre- and post-treatment at any of the four test intervals, nor was there a significant effect of treatment when examining the active group only in a treatment by interval ANOVA. The two groups did not significantly differ in the pre-treatment session for either eyes closed or eyes open slow eye movements. There were no significant differences between the groups in EEG fast alpha power; nor were there any Group by Session interactions, indicating that fast alpha power was not significantly affected by treatment. As expected there was a highly significant state effect ($F(1,14)=231.00$; $p<0.001$), with greater alpha power in the eyes closed state than in the eyes open state. There was also a significant Test Interval by Treatment Group interaction ($F(3, 42)=3.89$; $p<0.05$) but this effect did not interact with Test Session. In general, the placebo group showed little change in alpha power across the first 3 intervals, with an increase in power during the $4^{th}$ interval. The active treatment group showed decreased alpha power during the first interval relative to the placebo group, and relative to the later testing intervals. Resting parietal theta did not significantly differ between the two treatment groups either before or after treatment. There was a main effect of state, with greater theta power in the eyes closed state ($F(1,14)=28.48$; $p<0.001$). There was also a significant main effect of interval ($F(3,42)=4.23$; $p=0.016$) with theta power increasing from the first interval to the third interval. There was also an interval by treatment interaction, but this was not very interesting and it did not interact with session.

Neurophysiological Cognitive. Frontal midline theta did not between groups as a function of task load or session. FM theta showed a main effect of interval, increasing across the session ($F(3,42)=4.32$; $p=0.023$). However, this effect interacted with session, load and treatment group (4-way interaction $F(3,42)=4.46$; $p<0.01$). In general, theta power increased across the session (at least from the first to third interval) for all cases except the post-treatment, high load condition for the sham group. In that case, fm theta decreased from across the session. Slow alpha power did not significantly differ between the two treatment groups either before or after treatment. There was a main effect of task load ($F(1,14)=16.71$; $p<0.01$), with larger alpha power in the low load than in the high load task. Although the load effect was significant for both groups, the effect was smaller for the active group, both before and after treatment. This resulted in a near-significant Load by Treatment interaction ($F(1, 14)=3.12$; $p=0.095$). There was also a main effect of recording interval ($F(3,42)=4.22$; $p<0.05$), with alpha increasing across the session for both groups. Although the omnibus ANOVA showed a significant effect of session, but not a session by treatment group interaction, post-hoc analyses on the active group and sham groups separately demonstrated that the active group had a significantly smaller P300 response in the second session than in the first, whereas the P300 of the sham group did differ between sessions. Neither the latency nor the amplitude of N100 was affected by treatment (no main effect of session, nor any significant interactions involving session).

Neurocognitive Function Change Index. The active CPAP group showed an improvement in function whereas the sham CPAP group showed a decrement (FIG. 10).

Conclusion: The NCFC appears to be sensitive to CPAP treatment in this sample of patients.

The following is a description of an experiment in which healthy subjects receiving the anxiolytic alprazolam were tested before and after treatment with our method and system for measuring changes in neurocognitive function.

METHOD AND RESULTS OF EXPERIMENT 5

Assessing Neurocognitive Effects of Psychiatric Medications

Summary: Psychiatric disorders such as anxiety or depression are often treated by medications that can produce undesirable cognitive side effects. Currently there are no standard means for assessing either medication-induced impairment, or the effects of medications intended to improve cognitive function. To address this technology gap, we developed a method and system to objectively assess medication-related changes in cognitive function. The device automatically combines neurophysiological signals and behavioral measures to provide a sensitive measure of a change in cognitive function, as described in Experiment 2. To develop and test the device, we collected a dataset of behavioral measures, as well as resting and task-related EEG measures from a small group of subjects acutely treated with a commonly prescribed anti-anxiety medication, alprazolam. Relative to placebo, alprazolam was associated with subjective, behavioral, and neurophysiological alterations in alertness, sustained attention, and working memory. We then applied a multivariate index function that combines behavioral and neurophysiological parameters to this data set and found that it could serve as a sensitive detector of medication-induced impairment in cognitive function.

Experiment: The motivation behind this experiment was to evaluate whether EEG and/or behavioral indices could be used to detect cognitive side effects of a common psychiatric medication. To meet this objective data were collected from N=10 healthy subjects (21–35 yrs; 5 women, 5 men) before and after consuming a placebo or 1 mg of alprazolam (Xanax). Alprazolam is commonly prescribed for treatment of anxiety disorders. It acts primarily on the GABAergic system, enhancing the inhibitory effects of this neurotransmitter. In increasing doses, alprazolam produces increased CNS depression ranging from sedation to coma. At anxiolytic therapeutic doses, alprazolam has clear sedating properties. It adversely affects memory functions and psychomotor performance following acute administration, and its CNS effects can be detected in EEG measures. For experimental purposes it is attractive because it is fast acting and has a short half-life (Tpeak of 1–2 hrs, a plasma half-life of 6–16 hrs). The experiment was performed according to a double blind, fully counterbalanced design, and all participation was fully informed and voluntary.

Participants were admitted to the study following a medical exam by a neurologist to insure that they were healthy and free from any contraindications for alprazolam. They then participated in three sessions: a training session and two experimental sessions. In the initial session, following informed consent procedures, subjects were familiarized with the recording methods and apparatus, and given a sham (placebo) drug dose. They then practiced the tasks until performance levels reached asymptote. On subsequent days (at least a week apart), they participated in two experimental sessions (alprazolam or placebo). Each session occurred at the same time of day, and included a similar light meal. Each session consisted of a pre-drug baseline-recording interval, followed by five post-drug recording intervals extending to 5 hours after drug administration. In the pre-drug interval and in each of the post-drug intervals EEG was recorded while subjects performed computer-presented tasks and while they rested quietly. The computerized tasks included easy and difficult versions of a sustained attention working memory task, where difficulty was manipulated by varying working memory load. Subjective scales were also used to assess drowsiness, mood, and perceived drug effects. The entire procedure, including preparation time and rest breaks lasted approximately 7 hours. Transportation home was provided for the subjects at the end of each experimental session.

Results

Subjective: Alprazolam was associated with a number of subjective effects. When comparing alprazolam to placebo, the participants consistently reported on a visual analogue scale a heightened sense that they could "feel the effects of the drug", beginning 0.5 hrs after drug ingestion, peaking 1.5–2 hrs after drug ingestion, and remaining significantly elevated throughout the rest of the session (Drug by Recording Interval interaction, $F(5,45)=21.08$; $p<0.001$). Subjects also indicated that they felt significantly more sleepy, more "spacey/out of it", and more clumsy after ingesting alprazolam than after ingesting placebo.

Behavioral Performance: In conjunction with the clear subjective effects, alprazolam also had a significant negative impact on performance. In both the easy and difficult level of the task, subjects were significantly slower ($F(5,45)=6.47$; $p<0.01$) and less accurate ($F(5,45)=5.88$; $p<0.01$) after ingesting alprazolam than after ingesting placebo. The largest effect on behavioral performance was observed 0.5–1 hrs after drug ingestion, with behavior returning towards baseline levels by 3.5–4 hrs post drug ingestion.

Neurophysiological Alertness: Alprazolam was also associated with a number of CNS effects as evidenced in the EEG. Although subjects reported feelings of drowsiness, especially within the first 3 hrs of alprazolam ingestion, the EEG changes in the resting eyes open and eyes closed conditions did not exhibit classical signs of drowsiness. For example, drowsiness is typically associated with an increase in theta power. Relative to the placebo condition, alprazolam produced a significant decrease in theta power in the eyes open state ($F(5,45)=3.31$; $p<0.05$) whereas it did not affect theta power in the eyes closed state ($F<1$). Typically, drowsiness is associated with relatively greater decline in alpha power when eyes are closed than when eyes are open; indeed the ratio of alpha power in the eyes closed versus eyes open state has been used as a sensitive indicator of drowsiness. Alprazolam significantly reduced alpha power in both eyes open and eyes closed states relative to placebo (FIG. 2; $F(5,45)=9.53$; $p<0.001$), but did not significantly change the ratio of eyes closed alpha power to eyes open alpha power ($p>0.1$). Alprazolam was associated with a highly significant increase in beta power in the resting eyes closed state ($F(5,45)=24.73$; $p<001$). Beta power was largest 0.5–1 hrs post drug ingestion but remained elevated throughout the session. Beta power in the eyes open state showed the same pattern of enhancement after drug ingestion, but to a lesser extent than in the eyes closed state ($F(5,45)=18.01$; $p<0.001$). Thus although subjects reported feelings of subjective drowsiness, the EEG differences between placebo and alprazolam days differed somewhat from the classical, EEG definition of drowsiness.

Neurophysiological Cognitive: Alprazolam also produced a number of changes in the task-related EEG. Frontal midline theta was significantly attenuated by alprazolam ($F(5,45)=5.62$; $p<0.01$), as were both the slow ($F(5,45)=10.57$; $p<0.001$) and fast alpha signals ($F(5,45)=6.07$;

p<0.01). Although the reduction in theta and alpha power was apparent throughout the session, the largest effects occurred at 0.5–1 and 1.5–2 hrs post drug ingestion. In these intervals, the task-difficulty related modulation of the EEG (i.e. the increase in FM theta and the decrease in alpha with increased task difficulty) was significantly attenuated. Beta power was significantly larger on the alprazolam day than on the placebo day (F(5,45)=17.15; p<0.001), with the largest effects occurring 0.5–1 hr post drug ingestion. Finally, alprazolam also affected the P300 ERP. In the difficult task level alprazolam significantly reduced P300 amplitude (main effect of drug: F(1,9)=34.993; p<0.001), with the largest reduction occurring 1.5–2 hrs post drug ingestion. The P300 remained significantly depressed throughout the session. P300 amplitude in the low load task level and in the simple reaction time task did not significantly differ between placebo and alprazolam conditions.

Together, these results show that in healthy young adults, the ingestion of 1 mg of alprazolam produced strong subjective sensations, clear behavioral impairments, and large changes in resting and task-related EEG measures. The time-course of these effects differed. Subjective effects, behavioral impairment and the task-difficulty related attenuation of the alpha signal were large during the first 2–3 hrs after drug ingestion, then recovered toward baseline levels. In contrast, other task-related neurophysiological variables, such as P300 amplitude, and resting EEG variables were significantly affected by alprazolam even 4.5–5 hrs after drug ingestion.

Neurocognitive Function Change Index: We used the NCFC index described in Experiment 2 (that melds a rule-based system with a neural network-like combinatorial scheme) to this data set. The resulting function is structured such that improvement in cognitive function in response to some intervention results in a positive deviation of the index, and impairment in cognitive function in response to some intervention results in a negative deviation of the index. The results from applying this function to the data are presented in FIG. 11. Consistent with the subjective, behavioral, and EEG results presented above, the hybrid multivariate index suggests that alprazolam had a dramatic effect on neurocognitive function. In the first and second periods following drug ingestion the change in index values were highly significant across the group of subjects (t(9)=−4.02, p<0.004 and t(9)=−3.54, p<0.007 for t1 and t2 respectively), with some recovery in the later test periods (p's<0.05 for the rest of the test session).

Conclusion: Together with the univariate findings presented above, these results provide strong support for the notion that our testing and analysis approach provides a viable means for detecting neurocognitive impairment that might occur as a side effect of a psychiatric medication.

The following is a description of an experiment in which healthy subjects receiving the anti-seizure medication phenytoin were tested before and after treatment with our method and system for measuring changes in neurocognitive function.

METHOD AND RESULTS OF EXPERIMENT 6

Assessing Neurocognitive Effects of Neurological Medications (Anti-Epileptic Drugs)

Summary: Over two million people in the U.S. suffer from epilepsy, and many of these individuals experience significant cognitive dysfunction in conjunction with their seizure disorder. The causes of cognitive impairment in epilepsy include such factors as seizure type and frequency, presence of lesions, age of onset, and effects of anti-epileptic drugs (AEDs). The one factor that the clinician has most direct control over is choice of an AED and appropriate dosing regimen. Many well-controlled studies have shown that AEDs can produce significant cognitive deficits particularly when given in high doses, or in combinations with other AEDs. One of the primary effects of AEDs is slowed psychomotor performance, and some AEDs can also have sedating effects. AEDs have also been found to impair performance on tasks that demand sustained attention and concentration, and sometimes interfere with learning and memory. Understanding the impact of AEDs on cognitive function is of particular importance since long-term AED therapy is the major form of epilepsy treatment and it is often initiated in childhood even though the impact (if any) of chronic AED treatment on brain maturation is not yet known.

As described in Experiment 2, we have developed a method and system to objectively assess medication-related changes in cognitive function, which might be used to assess changes in cognitive function associated with AEDs. To evaluate the approach for this application, we collected a dataset of behavioral measures, as well as resting and task-related EEG measures from a small group of subjects acutely treated with a commonly prescribed AED, phenytoin. Phenytoin was associated with subjective effects and neurophysiological alterations in alertness and in attention and working memory, in the absence of significant overt behavioral impairment. We applied a multivariate index function that combines behavioral and neurophysiological parameters to this data set and found that it could serve as a sensitive detector of AED-related changes in cognitive function.

Experiment: The motivation behind this experiment was to evaluate how EEG and behavioral indices might be used to detect mild cognitive side effects of neurological medications, such as anti-epileptic drugs (AEDs). To meet this objective data were collected from N=7 healthy normal subjects before and after consuming either a placebo or an acute dose of phenytoin (Dilantin), 10 mg/kg bodyweight. The experiment had a double blind, placebo-controlled crossover design.

Phenytoin is one of the oldest and historically most commonly prescribed anticonvulsants. According to the manufacturer, possible side effects of treatment with phenytoin include nystagmus, dizziness, sleepiness, and impaired motor coordination. However, little literature exists concerning the effects of a single oral dose of phenytoin on cognitive function in otherwise healthy subjects. Some studies have found no effects, whereas others have shown small but significant response slowing and increases in subjective sedation. Other researchers have reported that normal subjects with high serum levels of phenytoin consistently report subjective side effects, but that their cognitive or performance capabilities were not impaired. We chose to conduct our initial study using phenytoin exactly because of the inconsistencies and subtleties of its reported cognitive effects. That is, the incorporation of task-related EEG measures into assessments of neurocognitive status would be particularly valuable when applied in circumstances where effects on behavior might be small and where the pattern of effects might differ between patients.

Participants were admitted to the study following a medical exam by a neurologist to insure that they were healthy and free from any contraindications for phenytoin. They then participated in three sessions: a training session and two experimental sessions. In the initial session, following informed consent procedures, subjects were familiarized with the recording methods and apparatus, and given a sham (placebo) drug dose. They then practiced the tasks until performance levels reached asymptote. On subsequent days (at least a week apart), they participated in two experimental sessions (phenytoin or placebo). Each session occurred at the same time of day, and included a similar light meal. Each session consisted of a pre-drug baseline recording interval followed by five post-drug recording intervals extending to 5 hours after drug administration. In the pre-drug interval and in each of the post-drug intervals EEG was recorded while subjects performed computer-presented tasks and while they rested quietly. The computerized tasks included a simple reaction time task and easy and difficult versions of the sustained attention WM task, in which difficulty was manipulated by varying WM load. Subjective scales were also administered to assess drowsiness, mood, and perceived drug effects. Blood samples were obtained at 3 and 5 hours after drug ingestion to ascertain drug serum levels. Transportation home was provided at the end of the sessions.

Results

Blood levels and subjective effects: Blood serum levels were higher 5 hrs after 3 hrs. At 5 hrs, mean blood serum level was 9.0 $\mu$gm/ml (range 3.5 to 13.6); i.e. just below the therapeutic range of 10–20 $\mu$m/ml. Even at this relatively low dose, phenytoin appeared to induce subjective effects. When comparing phenytoin to placebo, participants consistently reported on a visual analogue subjective scale a heightened sense that they could "feel the effects of the drug", with the strongest sensations occurring about 4 hours after drug administration (t(6)=3.9, p<0.01). Subjects also indicated that they felt marginally more sleepy after phenytoin than after placebo (t(6)=2.17, p<0.075).

Neurophysiological Alertness: To examine whether there was any neurophysiological evidence for decreased alertness, the EEG data were processed to eliminate artifacts and to compute power spectra and ERPs in each test condition. Examination of grand average (collapsed across subjects) power spectra for the EEG during resting conditions around the peak of the subjective drug effect revealed differences between phenytoin and placebo. During the eyes-closed resting condition, a small increase in power in the 3–6 Hz (theta band) frequency range at parieto-occipital electrodes was observed in the phenytoin condition relative to placebo. This was accompanied by a decrease in power in the 9–11 Hz (alpha band) frequency range (t(6)=2.93, p<0.05). These physiological changes are consistent with the subjective reports of increased drowsiness following phenytoin.

Behavioral Performance: Although the subjective reports and background EEG data provided evidence of increased drowsiness in the subjects, neither accuracy nor reaction time during task performance differed on average across the group between the phenytoin and placebo conditions.

Neurophysiological Cognitive: Despite the absence of behavioral impairment, phenytoin reduced the difficulty-related enhancement of the frontal midline theta signal (t(6)=4.63; p<0.01) that is otherwise observed when comparing the low load and high load versions of working memory tasks. Thus, task-related EEG measures appeared to provide sensitive indices of drug effects even under circumstances where behavioral measures are relatively insensitive and where acute drug serum levels are on the low end of the therapeutic range. Similarly, phenytoin also affected attention related modulation of the amplitude of the N160 ERP response. In particular, in the easy level of the task, subjects tend to covertly maintain attention to the target location presented on the first trial in the block. This results in an enhancement of the N160 response to target stimuli. This effect, which was observed in the placebo condition, was significantly reduced in the phenytoin condition (t(6)=3.175; p<0.05). For later ERPs such as the centroparietal P300 component, the effects of phenytoin were heterogeneous, with a few subjects showing a marked reduction in ERP amplitude in the phenytoin condition, and others showing no change or a small increase in amplitude. Such results indicate that a dose of phenytoin too small to affect overt behavior nonetheless could be detected in changes in neurophysiological activity associated with task performance.

Neurocognitive Function Change Index: The hybrid multivariate function for assessing changes in neurocognitive function described in Experiment 2 was also applied to this dataset, computing degree of neurocognitive change from an average of the placebo test sessions. The resulting index scores were then computed as deviations from the pre-drug test administration index score to illustrate how neurocognitive function varied over the phenytoin test session. The results of this analysis are shown in FIG. 12. Following administration of phenytoin average scores on the NCFC index tended to decline relative to the pre-treatment baseline interval. A nadir occurred a few hours following drug administration. Compared to the expected value of 0, average scores indicated significant impairment at the time of this functional trough (one-tailed t(6)=−2.35, p<0.03). Comparing these data to those presented in FIG. 11 is of interest in that it provides an illustration of use of this method to compare the cognitive pharmacodynamics of different medications. In this case the pharmacodynamic profile presented by alprazolam in FIG. 11 is one where the onset of cognitive impairment from the medication is rapid and relatively severe, whereas that presented by phenytoin in FIG. 12 is slower to develop and relatively mild. Such results are consistent both with prior studies of the cognitive side effects of these medications as well as their known pharmacokinetics.

In addition to providing a useful tool for studying the effects of treatment interventions across groups of subjects (as might be done in clinical trials), this approach is also amenable for use in studying individual differences in response to a particular medical treatment. For example, FIG. 13 illustrates the range of neurocognitive index function scores over each of the test intervals for each of the seven subjects in the study. These data indicate that while a few of the subjects appeared to be free of adverse neurocognitive effects in response to phenytoin, the rest of the sample displayed some acute impairment, especially in the period 2–4 hours following drug ingestion. Such individual difference data might prove useful in studies of pharmacogenetics or in the clinical evaluation of individual patients' responses to treatment regimens.

Conclusion: In sum, these results indicate that the multivariate index of neurocognitive function that was developed in past studies could be successfully generalized for use in detecting the relatively mild medication-induced impairment observed in the current study following a single dose of phenytoin. Initial results from a related experiment that is currently in progress (described below) suggest that the NCFC index is also useful for assessing cognitive changes associated with chronic AED administration.

In Progress Study of Effects of Chronic AED Administration. Although their mechanisms of action are varied and incompletely understood, AEDs as a class tend to limit sustained repetitive firing of neurons by antagonizing mechanisms of excitation or by agonizing mechanisms of inhibition. It is likely that such effects have a measurable influence on task-related EEG or ERP parameters. Such biomarkers are being identified through exploratory analyses of data from subjects taking AEDs for 4 weeks. The study, which is being performed by Drs. F. Gilliam and K. Meador, is a randomized, double blind, crossover comparison of the cognitive and behavioral effects of chronic administration of the AEDs lamotrigine and topiramate in healthy adults. Lamotrigine and topiramate are newer AEDs that have been reported to differ in their cognitive side effects. In particular, topiramate is thought to have a relatively worse cognitive side effect profile than lamotrigine.

The study is designed such that subjects are randomized in a first treatment period to receive either lamotrigine or topiramate for 12 weeks (7 weeks of dose escalation followed by 4 weeks of maintenance therapy and then 1 week of tapering off the drug). The target maintenance doses for both lamotrigine and topiramate are 300 mg/day. After completion of the first treatment period, subjects enter a washout period of 4 weeks followed by treatment with the alternate therapy for 12 weeks in the second treatment period (7 weeks of dose escalation followed by 4 weeks of maintenance therapy and then 1 week of tapering off the drug). Test periods occur at enrollment into the study, at the end of the maintenance phase of the first treatment, at the end of the maintenance phase of the second treatment, and one month after the second AED is stopped. In each test session, subjects have their EEG recorded from 8 scalp electrodes (positioned at AFz, F3, F4, C3, C4, Pz, PO3, PO4) and their EOG recorded from electrodes placed on the supraorbital ridge and outer canthus of each eye, while they perform the WM task and while they rest quietly.

Through March 2002, twelve subjects have completed major portions of the protocol out of a total target sample of twenty. All twelve subjects have received at least one drug intervention, and nine have completed the entire protocol and received both drugs. Although the blind from the study will not be broken until the data collection and preliminary analyses have been completed, initial results suggest that one or both of the treatments are producing readily detectable changes in cognitive function. For the overall NCFC measure of neurocognitive function, ten of the twelve subjects displayed varying degrees of impairment relative to baseline for at least one drug condition (data from one of these subjects appears in FIG. 14). These data thus suggest that the NCFC index is appropriate for use in assessing the neurocognitive consequences of chronic AED use.

The following is a description of an experiment in which healthy subjects receiving marijuana were tested before and after treatment with our method and system for measuring changes in neurocognitive function.

METHOD AND RESULTS OF EXPERIMENT 7

Assessing Neurocognitive Effects of Recreational Drugs (Marijuana)

Summary: Marijuana is by far the most widely used generally illegal psychoactive drug in the USA, as some 70 million Americans have tried it at least once, and between 2–3% of Americans use marijuana daily (Adams & Martin, 1996). Marijuana has purported medicinal value, and medical marijuana has been recently decriminalized in a number of states. However, it is better known for its subjective and cognitive effects, and an important factor in the decision to prescribe marijuana to a suffering patient is how the potential decrements in attention, concentration, and memory will affect the patient's ability to cope with everyday life. Physicians must be able to accurately weigh the therapeutic effects of medicinal marijuana against the potential disturbance to the patient's ability to work, drive, and interact with others. Unfortunately, there is currently no standard means for assessing the cognitive impairment associated with marijuana ingestion.

The method and system described above for objectively assessing medication-related changes in cognitive function might also be useful for assessing changes in cognitive function associated with marijuana use or with the use of other intoxicants and recreational drugs. To evaluate the approach for this application, we collected a dataset of behavioral measures, as well as resting and task-related EEG measures from a small group of subjects acutely treated with smoked marijuana. Marijuana was associated with subjective effects, changes in autonomic measures of arousal, impaired test performance, and neurophysiological alterations in signals of alertness, attention, and memory. We applied the NCFC index that combines behavioral and neurophysiological parameters to this data set and found that it could serve as a sensitive detector of marijuana-related changes in cognitive function.

Experiment. Past studies have indicated that the most reliable cognitive effects of acute marijuana use include disruption of attention and memory abilities. Data during performance of attention and memory tests were thus collected from N=10 casual marijuana smokers (21–35 yrs; 5 women, 5 men) before and after smoking an active marijuana cigarette containing 3.45% $\Delta^9$-THC and placebo marijuana cigarette containing 0.006% $\Delta^9$-THC. Casual smokers were defined as those who reported smoking marijuana between once a month and once a week over the last year. The experiment was performed according to a double blind, fully counterbalanced design, and all participation was fully informed and voluntary.

Participants were admitted to the study following a medical exam by a neurologist to ensure that they were healthy and had no contraindications for marijuana smoking. Subjects were excluded if they or any immediate family member ever had a dependence on marijuana, alcohol or any other drug. Medical and drug use histories were obtained from each subject to determine eligibility in the study. Other negative selection criteria included pregnancy, current cigarette smoking, consumption of more than 10 alcoholic drinks per week, history of neurological or psychiatric disorder, and prior habitual use or any use within the last month of any illicit drug other than marijuana. Subjects were paid for their participation, and were given additional monetary bonuses based on their task performance.

Each subject participated in one training day and two test days. On the training day, subjects learned the experimental tasks, became familiar with the recording procedures, and practiced the smoking procedure with an herbal cigarette containing no marijuana or tobacco. The test days occurred a week apart at the same time of day, and included a similar light meal. On the test days, subjects participated in five recording intervals, each one-hour apart: one pre-smoking baseline interval, and four post-smoking intervals. After completing the baseline Interval 1, subjects smoked one cigarette containing active or placebo marijuana, according to a computerized, paced smoking procedure: Subjects smoked 6 puffs from a single marijuana cigarette, with each puff one minute apart. On each puff, they inhaled for 1.5 seconds, held the smoke in their lungs for 8.5 seconds, then exhaled, and rested for 50 seconds before taking the next puff.

Subjects were required to perform tests of spatial working memory that required maintaining and processing stimuli in mind over a period of 5–10 seconds and verbal intermediate-term memory (ITM) that required recognition of previously studied stimuli over a period of 5–10 minutes between study and test periods. In each of five recording intervals, subjects completed these tasks and a number of other tests and scales in a battery lasting approximately 45 minutes. The task battery consisted of subjective effects scales, the ITM task with the spatial working memory task of two difficulty levels embedded inside, 90 sec each of eyes-open and eyes-closed resting EEG, a time estimation task, and easy and difficult driving simulator scenarios. A rest period of approximately 15 minutes was given every hour, after completion of the task battery. The entire procedure, including preparation time and rest breaks lasted approximately 6–7 hours. Subjects were sent home via taxicab at the end of each test day.

Results

Autonomic and subjective measures: Physiological measures revealed that heart rate increased markedly within minutes after smoking active relative to placebo marijuana, and remained elevated throughout the testing day ($F(4,36)=13.82$, $p<0.001$). Systolic blood pressure was elevated directly after smoking active marijuana ($F(1,9)=11.73$, $p<0.01$), but returned to near baseline levels an hour later. As expected, subjects felt more high and impaired after smoking active marijuana, and reported experiencing changes perceiving time and space ($p$'s$<0.01$). However, there was no difference between active and placebo marijuana on subjective ratings of sleepiness or motivation.

Behavioral Performance: Subjects reported having difficulty paying attention and remembering things after smoking active relative to placebo marijuana, and their performance data bears this out. Marijuana slowed responses in the working memory task ($F(4,36)=8.80$, $p<0.01$), in both the easy 0-back and difficult 2-back versions. In the word recognition phase of the ITM task, a recognition test of items presented 5–10 minutes previously, marijuana appeared to affect a specific aspect of memory ability. In particular, the ability to recognize old words as having been seen before was relatively unaffected after smoking active marijuana ($F(4,36)=1.56$, $p>0.10$), whereas the ability to classify words not seen before as "New" was impaired ($F(4,36)=4.56$, $p<0.05$). Similarly, reaction times to old words were unaffected after smoking marijuana, but reaction times to new words increased (marijuana×interval×old/new interaction: $F(1,9)=16.91$, $p<0.01$). Such performance is consistent with previous reports of marijuana increasing errors of commission or memory "intrusions" in recognition and recall tests. The behavioral effects of marijuana were largest up to 1.5 hours after smoking, and dissipated somewhat but not completely by the end of the day, 3–4 hours post-smoking.

Neurophysiological Cognitive: Marijuana smoking also produced marked CNS effects, reflected in task-related EEG differences after smoking the active versus placebo cigarette. There was a topographically widespread decrease in EEG power in the working memory task after smoking active versus placebo marijuana, particularly in the 4–6 Hz theta range ($F(4,36)=4.94$, $p<0.01$). Event-related potentials (ERPs) in the working memory task were reduced substantially after smoking active relative to placebo marijuana. In the first post-smoking interval, N100 amplitude decreased, particularly in the more difficult 2-back condition ($F(1,9)=11.82$, $p<0.01$), and P300 amplitude decreased, particularly in the easier 0-back condition ($F(1,9)=12.56$, $p<0.01$). Marijuana smoking had no significant effects on working memory task ERP latencies.

The primary EEG finding in the test phase of the recognition memory task was greater power over a wide frequency range in the one second following a correct "New Word" response than a correct "Previously Seen Word" response. After smoking active marijuana, this EEG difference between Previously Seen and New responses was reduced ($F(4,36)=2.66$ $p<0.05$). The most prominent ERP observed in the ITM task is a large, slow central positivity that is larger following the onset of Previously Seen Words than New Words. In the interval directly after smoking marijuana, the amplitude of this component was reduced substantially during the second recognition test ($F(1,9)=6.90$, $p<0.05$). These effects were evident within 30 minutes of marijuana smoking, and generally persisted until the final recording interval, 3.5 hrs after smoking. In sum, marijuana had a large effect on ERPs, substantially reducing the amplitudes of components reflecting attention and memory retrieval processes. Such a reduction in amplitude suggests that neuronal populations were less responsive to stimuli after marijuana smoking.

Together, these results show that in healthy, young, casual marijuana users, smoking a marijuana cigarette produced strong subjective sensations, clear behavioral alterations, and large changes in task-related EEG and ERP measures. These effects were apparent within minutes after smoking, and tended to diminish but not fully disappear 3–4 hours later.

Neurophysiological Alertness: Neurophysiological and subjective signs of drowsiness were not significantly affected by marijuana smoking. This suggests that the large effects on attention and memory observed were specific effects of marijuana on cognition, rather than an indirect behavioral alteration resulting from marijuana making subjects drowsy.

Neurocognitive Function Change Index: Finally, the hybrid multivariate method for calculating the NCFC index was also applied to these data. Following administration of marijuana average scores on the neurocognitive index function tended to decline relative to the pre-treatment baseline interval. A nadir occurred in the period 0.5–1.5 hrs following marijuana smoking. As described in Experiment 2, the composite NCFC index is the sum of three sub indices: a Behavioral Performance sub index, a Neurophysiological Cognitive sub index, and a Neurophysiological Alertness sub index. The observed changes on each of these three sub indices are illustrated in FIG. 15. They illustrate a unique strength of our approach. In particular, the Behavioral Performance and Neurophysiological Cognitive sub indices show functional impairment from smoking marijuana, whereas a lack of any decrease on the Neurophysiological Alertness sub index indicates that the impairment was not simply due to sedation, but rather to some more specific interference with the neural systems underlying attention and memory abilities.

Conclusion: These results indicate that the NCFC index and its sub indices are sensitive to the neurological changes produced by marijuana smoking.

The following is a description of an experiment in which healthy elderly subjects receiving the antihistamine diphenhydramine were tested before and after treatment with our method and system for measuring changes in neurocognitive function.

METHOD AND RESULTS OF EXPERIMENT 8

Assessing Neurocognitive Effects of Medications in Elderly Patient Populations

Background and Summary. A variety of well-documented factors can produce cognitive impairment in elderly individuals. Such impairments compromise quality-of-life, and are associated with high economic costs. While some sources of cognitive decline in the elderly are progressive and currently incurable, in other cases cognitive impairment can be arrested and even reversed with proper diagnosis and treatment. One of the most common, and most treatable, forms of cognitive impairment in the elderly is that produced as a side effect of drugs used to treat conditions common to this population. While medication-induced cognitive impairment is a serious concern in all age groups, the elderly are at increased-risk. In part, this is because any medication-related impairment is superimposed on the cognitive slowing and reduced capacity characteristic of normal aging. However, age-related changes in pharmacokinetics, especially reduced hepatic metabolism and renal clearance, also contribute to the increased risk. These metabolic changes result in higher plasma drug concentrations and longer elimination half-lives in the elderly than in younger patients. This increased risk from metabolic slowing is compounded by the fact that the elderly take more prescribed and over-the-counter medications than do younger individuals—although they constitute about 10% of the population, older adults receive about 25% of all prescriptions. They thus have increased probability of adverse drug-drug interactions. Finally, older individuals are subject to added risk of drug related impairment by the fact that they suffer from increased incidence of comorbid conditions which themselves are associated with pathological cognitive decline. As a result of these factors, drugs have been reported to contribute to (or even to be the primary cause of) the cognitive impairment seen in over 10% of patients evaluated for dementia in primary care settings, and elderly are often prescribed inappropriate medications (typically antidepressant or antianxiety drugs) that can produce serious adverse effects (such as memory problems, confusion, sedation or loss of motor control) that compromise their well-being.

A major problem in determining the extent to which drugs might produce cognitive side effects in the elderly is that there are few standardized and sufficiently sensitive yet efficient means for assessing cognitive changes associated with drug therapies. The method and system described above for objectively assessing changes in cognitive function might also be useful for assessing medication effects in elderly subjects. However, there are well-established EEG and behavioral differences between the population of young adult subjects that the NCFC method was developed on, and the elderly adult population. For example, reports of age-related changes in behavior include increased slowing, and in EEG measures include reduced spectral power in the lower frequencies, increased power in the higher frequencies, decreased interhemispheric coherence, and decreased amplitude and longer-latency ERP components. Such differences could produce poor generalization of the method to elderly subjects. Thus, to evaluate the suitability of the approach for evaluating the neurocognitive effects of medications in the elderly, we collected a dataset of behavioral measures, as well as resting and task-related EEG measures, from a small group of elderly subjects before and after they were treated with the antihistamine diphenhydramine. This medication was also used in the studies of young adult subjects described in Experiments 1 and 2. In the elderly group, diphenhydramine was found to produce little or no overt behavioral impairment relative to younger subjects. However, despite the lack of substantial behavioral impairment, neurophysiological measures indicated that the subjects experienced a significant decrease in alertness and impaired attention functions. We applied the NCFC index to this data set and found that it could also serve as a sensitive detector of medication-related changes in cognitive function in elderly subjects.

Experiment. Behavior, EEG, and ERP measures were recorded from healthy, neurologically normal, elderly subjects while they performed cognitive tasks. These individuals were tested before and after taking a 50 mg dose of the over-the-counter antihistamine diphenhydramine. This intervention was used as a safe, transient, and practical model of impairment in the elderly. The histaminergic system exerts modulatory effects on acetylcholine release. Since disruption of the histaminergic system is thought to contribute to some neurodegenerative disorders, antihistamines might be expected to affect alertness, attention, and memory functions in elderly subjects. Diphenhydramine is a histamine HI receptor antagonist that, in animals, induces memory deficits that are reversible by acetylcholine agonists like vasopressin. In humans, it has been shown to impair cognitive function; most frequently in young adult subjects in attention-demanding tasks. The majority of these studies have used the maximum recommended dose (50 mg) for the relief of allergy symptoms.

In this study, 12 healthy, high functioning individuals between the ages of 62 and 75 years (average age 68.3 years) were recruited from the community. All subjects were medically screened by a licensed physician prior to enrollment to ensure that they were healthy, that they had no signs of dementia, and that they did not have any conditions for which diphenhydramine was contraindicated. Other exclusion criteria included use of any psychoactive medications, any previous negative reaction to allergy medications, history of alcohol abuse, or routine consumption of more than 2 caffeinated beverages per day. Average level of education for the subject group was 17.9 years, with a mean Wechsler Adult Scale of Intelligence (WASI) Full-Four IQ of 125.3. Scores on the Mini Mental State Exam (MMSE) were at least 28/30. All subjects scored within the normal range on the Geriatric Depression Scale (short form). Written informed consent was obtained from all subjects. Subjects were paid for their participation.

Subjects participated in four sessions. In the first session, following medical screening and assessment with the WASI, subjects were introduced to the spatial working memory (WM) and word recognition intermediate term memory (ITM) tasks as described above in experiment 7. In the second session, multi-channel EEG was recorded while subjects practiced the tasks. After the practice session, subjects participated in two test sessions. Test sessions occurred one week apart at the same time of day, and included a similar light meal. On the test days, subjects participated in five recording intervals, a pre-drug ingestion baseline interval, followed by four post-drug ingestion recording intervals. The post-drug recording intervals occurred one hour apart, and began 0.5 hr after drug ingestion. In each interval, subjects had their EEG recorded while they rested quietly with their eyes open and eyes closed, and while they performed the task battery. In each recording interval, subjects also rated their subjective sleepiness using the Karolinska sleepiness scale. Data from the placebo session were compared with data from the diphenhydramine session. In univariate analyses, each variable was submitted to a Drug-by-Recording-Interval, within-subjects repeated measures ANOVA. A significant effect of diphenhydramine would be manifest as a Drug by Interval interaction. When such an interaction was observed, post-hoc t-tests were used to determine which recording intervals differed between the two drug conditions.

Results

Subjective Measures: Subjectively, participants reported feeling significantly sleepier after ingesting diphenhydramine than after ingesting placebo (Drug by Interval F(4,44)=5.44; p<0.01). Differences between placebo and drug conditions were significant 1.5 and 2.5 hrs post drug ingestion, with the greatest subjective sleepiness occurring 2.5 hrs after ingestion.

Neurophysiological Alertness: The resting EEG showed some characteristic signs of drowsiness following diphenhydramine administration. This included an increase in power in the delta and theta bands over posterior regions with peak effects occurring 1.5 and 2.5 hrs after drug ingestion (Delta: F(4,44)=3.737; p=0.011; Theta: F(4,44)=2.986; p<0.05). However, other expected signs of drowsiness which were observed following diphenhydramine treatment in young adults, such as a decrease in alpha power in the eyes closed condition, or an increase in slow eye movements, were not observed here.

Behavioral Performance: In contrast to its significant subjective effects and evidence in the resting EEG of drowsiness, diphenhydramine did not significantly affect task performance. In the WM task, subjects were faster and more accurate in performing the low load task than the high load task (RT: F(1,11)=333.33; p<0.001; accuracy: F(1,11)=23.03; p=0.001). Although subjects were somewhat slower and less accurate in the diphenhydramine condition than in the placebo condition, the Drug-by-Recording-Interval interactions were only marginally significant (RT: F(4,44)=2.81; p=0.098; accuracy: F(4,44)=2.35; p=0.069).

In the ITM task, univariate repeated measures analyses of RT and word recognition accuracy also did not show significant effects of diphenhydramine. As expected, subjects were faster and more accurate in recognizing the test words after the second presentation of the test list than after the first (RT: F(1,11)=157.90; p<0.001; accuracy: F(1,11)=95.67; p<0.001). Diphenhydramine did not impair this list learning. Although there was a trend for diphenhydramine to increase RT, especially to new words, the univariate ANOVA was not significant (F<1).

Neurophysiological Cognitive: Despite the relatively preserved performance in the face of subjective sleepiness, the task-related EEG and ERP measures showed significant effects of diphenhydramine. In the WM task, two ERP measures that are attenuated by drowsiness were significantly affected by diphenhydramine. The N160 maximal over parieto-occipital areas and the P350 maximal over midline centro-parietal areas were significantly smaller following diphenhydramine ingestion than placebo (N160: Drug by Interval interaction F(4,44)=6.58; p<0.001; P350: F(4,44)=5.375; p=0.001). Differences began 1.5 hrs after drug ingestion, peaked 2.5 hrs after ingestion, and returned toward baseline values 3.5 hrs after ingestion. These ERPs were attenuated in both the low and high load tasks.

The task-related EEG also showed changes consistent with increased drowsiness following diphenhydramine ingestion. Relative to placebo, diphenhydramine increased activity in the delta (F(4,44)=4.027; p<0.01), theta (F(4,44)=5.61; p=0.001), and alpha bands (main effect of drug, F(1,11)=7.454; p<0.05). The increase in theta power was not affected by task load. Delta power, however, increased more in the low load task than in the high load task (Drug by Task Load interaction F(1,11)=15.077; p=0.003). Power in the alphaband, was, as expected, significantly smaller in the high load task than in the low load task (F(1,11)=12.154; p=0.005). Although the interaction with task load was not significant, diphenhydramine had a somewhat larger effect on alpha in the high load task than in the low load task.

Diphenhydramine affected the ERPs elicited in the ITM task; it reduced the amplitude and increased the latency of early transient responses related to visual perception and attention, and affected later potentials that reflect memory-related processes. An early positive deflection occurring with an average latency of 122 msec over frontal areas was delayed, by an average of 10 msec, in the diphenhydramine condition relative to the placebo condition (Drug by Interval interaction (F(4,44)=3.840; p=0.009; peak difference occurred 2.5 hrs after drug ingestion). Following the frontal P120 response, there was a positive ERP maximal over posterior areas, with an average peak latency of 200 msec. The amplitude of this P200 was significantly larger to new words than to old words (F(1,11)=13.633; p<0.01), and larger after diphenhydramine ingestion than after placebo ingestion (Drug by Interval interaction F(4,44)=4.435; p=0.01; peak difference occurring 2.5 hrs after drug ingestion).

The memory-evoked shift (i.e. a greater positivity beginning at 300 msec to old words relative to new words) was significantly attenuated by diphenhydramine at 2.5 hrs after drug ingestion (F(1,11)=6.57; p<0.05). In the diphenhydramine condition, but not in the placebo condition, a late positive slow wave, occurring between 500 and 800 msec over frontal areas, was larger to new words than to the previously seen words (F(1,11)=5.4; p<0.05) at 1.5 and 2.5 hrs after drug ingestion. This was followed by a late sustained slow wave over both frontal and posterior areas. This slow wave was more negative to old words than to new words in the diphenhydramine condition but not in the placebo condition (F(1,11)=9.07; p<0.05). Peak differences between drug conditions occurred at 2.5 hrs after drug ingestion.

Neurocognitive Function Change Index: To assess the sensitivity of the NCFC index described above to the effects of diphenhydramine in the elderly, we applied it to data collected in this study. The relevant EEG and performance variables were extracted from the task and resting conditions of the medicated and unmedicated test sessions for each subject. These data were then used to calculate the composite index by computing difference scores between the baseline interval (t0) and each subsequent test interval (t1–t4) for the placebo and diphenhydramine sessions separately. The results are presented in FIG. 16. For both the placebo and diphenhydramine test conditions, average scores on the neurocognitive function index tended to decline relative to the pre-treatment baseline interval. This overall decline most likely reflects a general fatigue or time-on-task effect. However, the decline in the diphenhydramine condition was much more dramatic than that observed in the placebo condition, with average neurocognitive function scores reaching a minimum in the second (t2) post-treatment test interval. At that nadir 11 of the 12 subjects displayed negative values on the index score (binomial p<0.003). Compared to the expected value of 0, average scores in the diphenhydramine condition were significantly impaired in the second (one-tailed t(11)=−4.94, p<0.001), third (t=−3, 15, p<0.005), and fourth (t=−3.82, p<0.005) post-treatment test intervals. In paired comparisons with the placebo condition, the diphenhydramine scores were significantly worse in the second (t(11)=−2.20, p<0.03), and third (t(11)=−2.01, p=0.04) post-treatment test intervals.

Conclusions: These results indicate that the NCFC index developed in studies of healthy young adults could be successfully used to detect medication-induced impairment in the elderly subjects. Indeed, the general pattern and time course of the results resembled that obtained following treatment with diphenhydramine in the younger population described in Experiment 2.

The following is a description of an experiment in which our method and system is used for measuring differences in neurocognitive function between a medicated and an unmedicated state in children being treated with stimulant medications for attention deficit hyperactivity disorder.

METHOD AND RESULTS OF EXPERIMENT 9

Assessing Neurocognitive Effects of Stimulant Medications in Children with Attention-Deficit Hyperactivity Disorder Background and Summary. Attention deficit hyperactivity disorder (ADHD) is common in childhood, with a prevalence of about 3–5%, affecting 3 times as many boys as girls. According to one popular current model, the central problem driving ADHD symptoms is lack of inhibitory control, which in turn impairs the abilities to sustain focused attention, to hold information in working memory, and to self-regulate affect, arousal, and motivation. These difficulties are thought to underlie the maladaptive behaviors characteristic of children with ADHD. Problems with attention and impulse control are of particular concern because these functions are central to mastering developmental milestones and to general intellectual achievement.

A variety of strategies are available for treating childhood ADHD. Standard clinical treatment may include psychotherapy, pharmacotherapy, family therapy, and special education. Psychostimulant medications such as methylphenidate (Ritalin) are widely prescribed by pediatricians and have been more widely studied than any other type of treatment for any type of childhood disorder. For some children these medications work quite well, improving cognitive symptoms and social relations. Other children are "nonresponders" to stimulant treatment in that they appear to have no substantive benefits form such a pharmacological approach. Although ADHD is often successfully treated, research is needed to determine the optimal clinical strategies for best matching a particular patient to particular treatments and/or treatment combinations. Assessment in ADHD is complicated by the fact that although disruptive or maladaptive behaviors are overt and hence easily observable, inattentiveness is intrinsically a covert phenomenon. That is, there is currently no standard convenient measure to allow a clinican to assess neurocognitive status in children (or adults) with ADHD, or any general objective measure of whether stimulant treatment in this population improves neurocognitive function.

The NCFC method and system described above for objectively assessing changes in cognitive function might also be useful for measuring the effectiveness of treatment strategies for improving attention and alertness in children with ADHD. To evaluate this possibility, we collected a dataset of behavioral measures, as well as resting and task-related EEG measures, from a small group of children with ADHD on a day on which they were being treated with their normal dose of stimulant medication (either methylphenidate or Dexedrine), and on a day on which they abstained from taking their stimulant medication. The results indicate that the response to stimulant medication in this population is heterogeneous, with some patients showing a substantial improvement in neurocognitive function in response to treatment, and other showing little or no improvement. This result suggests that the method might have clinical utility in discriminating stimulant responders from nonresponders, helping to rationalize prescription of stimulant medication to only those children who might actually benefit from it.

Experiment. Participants (a total of N=14, evenly divided between boys and girls) were referred to this study by local ADHD specialists. All participants had been diagnosed with the combined subtype of ADHD and were currently undergoing treatment with stimulant medication. Inclusion criteria include age 8–12 years, no mental retardation or neurological impairment, and full-scale IQ in the normal range as measured by the WISC-III (Wechsler, 1991). Participants were paid $10/hour for their participation, and were reimbursed for transportation costs. To increase motivation, the children were also rewarded with toys for good performance.

EEG and behavioral data were collected while the children performed low load and high load versions of the spatial WM task described above. Children with ADHD have previously been reported to be impaired on spatial working memory tasks relative to normal controls, and studies of healthy adults have found that the stimulant methylphenidate improves performance on spatial working memory tasks. Participants were tested on each of three occasions at the same time of day with a week between sessions. The first occasion was an orientation and training session in which subjects learned and practiced the tasks until performance reached asymptote. On the other occasions they were tested either while medicated or while abstaining from their normal dose of medication, with order of treatment counterbalanced across subjects. A scientist not otherwise involved with the study maintained the schedule of medication and no-medication days so that the research assistant performing the testing and preliminary analyses was blind to medication status. Data from the orientation day was not included in formal analyses. On the other days subjects first performed a single 23-trial block of each of the task conditions as a warm-up procedure. They then performed 4 more 23-trial blocks of each test version in randomized order. A brief rest break was provided in the middle of the session. Eyes-open and eyes-closed resting EEG data was also collected from the children at the beginning and at the end of the test session.

In each session, multi-channel EEG was recorded from multiple "10-10 System" scalp locations (bandpass 0.1–100 Hz, 256 Hz sampling rate, linked mastoid reference) using a custom-made electrode cap. EOG was recorded from above and below the left eye, and from outer canthus of each eye. Preliminary analyses of these data followed the same procedures that we have used in all our recent studies of sustained attention as discussed above. Each subject's raw data was first inspected to determine whether any abnormal features were present (e.g., spike and wave complexes that might reflect undiagnosed epileptiform paroxysmal activity). The EEG was then preprocessed to automatically detect any artifactual contaminants. After artifact processing was completed, summary variables were computed for the mean and variance of performance accuracy and reaction time, banded spectral EEG features, and ERP peak amplitude and latency measures.

Results:

Neurophysiological Alertness: As in adult populations EEG alpha band power was larger in the resting eyes-closed condition than during the eyes-open condition ($F(13)=32.3$, $p<0.001$). However, no significant differences in alertness related physiological measures were observed in response to stimulant medication. This is consistent with past studies of stimulant use in adults that typically demonstrate significant increases in alertness in response to small doses of stimulants in sleep deprived subjects but not in well rested subjects.

Behavioral Performance: Our first analytic objective was to determine whether the children could do the tasks effectively and whether their performance was sensitive to the working memory load variation. Across the two test days average correct performance was 96%, (sd=4.8) in the low load and 86% (sd=10.7) in the high load task. Thus, even in the difficult test condition subjects performed the task well above chance levels The performance difference between levels was statistically significant ($F(13)=21.8$, $p<0.001$). Across the two test days average reaction time was 697 ms (sd=191) in the low load and 891 ms (sd=264) in the high load task. This difference was also significant ($F(13)=64.7$, $p<0.001$). That the behavioral results differ as a function of task load replicates our previous findings in adult subjects.

We next determined whether stimulant medication had any systematic effects on the children's task performance. In healthy adults, the effects of stimulants on performance vary with baseline alertness, drug dose, and task difficulty. Variation in abilities, symptoms, and treatments in children with ADHD are likely to further complicate this picture. Indeed, the typical prescribed single dose of stimulant medication ranged in our sample from 5–20 mg, and while the majority of the children had been prescribed methylphenidate, a few were instead prescribed Dexedrine. Furthermore, full-scale WISC scores in our sample ranged from 79–131 (mean IQ=103), and the group was composed of equal numbers of boys and girls with ADHD although the majority of research on medication effects in ADHD has been performed exclusively with boys.

Given the multiple sources of variability in the sample reviewed above, on an a priori basis it might be assumed that medication effects would also be highly variable across the sample. This is in fact what was found. While the data evidenced clear trends towards changes in behavioral and EEG parameters following treatment with stimulants, few effects reached significance. On average, performance accuracy was higher and reaction times were faster in the medicated condition. In a composite performance variable (proportion correct responses/normalized RT) this trend approached significance ($F(13)=3.9$, $p<0.08$). This trend towards improved performance is consistent with reports of improvements in spatial working memory ability in a homogenous group of healthy young adult subjects being treated with methylphenidate, and with reports of working memory improvements following stimulant treatment in children with ADHD.

Neurophysiological Cognitive: When comparing alpha power between the low load and high load conditions across the two test days, the children's alpha band EEG power displayed the adult pattern of lower power in the high load task condition ($F(13)=20.3$, $p<0.001$). Thus, the alpha rhythm in the children with ADHD included in the sample had task correlates that were the same as those observed in adult populations. We also examined stimulus-locked ERPs in the children, with special attention to the late positive component (P300). In young adults performing these tasks, this component typically differs between match and non-match working memory task stimuli. However, in the children in this sample there were no systematic differences in the ERPs related to this stimulus dimension ($F<1$).

No overall effects of medication on the alpha band EEG measures approached significance. In contrast, stimulant medication was associated with a slight reduction in theta band power in both task conditions ($F(13)=5.7$, $p<0.05$). This reduction was broadly distributed over the head rather than being specific to the frontal midline theta signal, and a similar reduction was also observed in the eyes-open resting condition. This reduction this likely reflects a general systemic effect of stimulant medication on the EEG rather than any specific change in attention-related cognitive functions per se. Stimulant medication was also found to enhance the amplitude of the P300 component of the ERP. In the low load task condition this enhancement was pronounced, with an average increase of around 3 $\mu V$ when comparing the medicated condition with the unmedicated condition ($F(13)=5.0$, $p<0.05$). A similar enhancement was observed in the high load task condition, but the increase did not reach significance. Given that this ERP component tends to be diminished when attention is distracted, this treatment-related enhancement suggests that stimulant medication improves attention function in this population.

The relatively modest average effects observed across the group as a whole belie relatively large effects sometimes observed in individual children. Such effects are consistent with the notion that children with ADHD differ with respect to the degree to which they respond positively to stimulant medication. For example, one subject showed large changes in the relative spectral power of the task related alpha rhythm during performance of the sustained attention working memory task following treatment. This subject was a boy in the average IQ range that was being treated with Dexedrine at a dosage of 20 mg. In this subject, behavioral performance in the task was markedly better in the medicated state relative to the unmedicated state. In addition, although in the group the alpha rhythm was not affected by treatment, the alpha rhythm in this subject demonstrated larger difficulty-related differences when comparing high load and low load versions of the task in the medicated state than in the unmedicated state, with a relatively greater attenuation of the alpha rhythm in the difficult 2-back task. We interpret this as reflecting improved volitional control over attention, with the subject apparently more able and/or willing to exert greater mental effort to respond to the more challenging task demand after medication.

Another example of a notable change in attention-related brain function after treatment with stimulant medication was observed when examining the amplitude of the P300 ERP in another subject in the medicated and unmedicated states. This subject was a girl in the low end of the average IQ range that was being treated with methylphenidate at a dosage of 10 mg at the time of the recording. In this subject, performance of the working memory task was also markedly better in the medicated state. In addition, consistent with the effect observed in the group, amplitude of the P300 potential was larger in the medicated condition, suggesting that methylphenidate increased this subject's attentiveness.

Neurocognitive Function Change Index: Such between-subject variability in responsiveness to stimulant medication, and in the particular neurophysiological parameters affected by stimulant treatment, suggests that conventional group-wise analyses of single electrophysiological parameters likely underestimates the real functional impact of treatment-related changes in patients with ADHD. However, the single subject analysis inherent in the NCFC multivariate method is well suited to such circumstances.

To evaluate this possibility we applied the function to the data collected in this experiment. The relevant EEG and performance variables were extracted from the task and resting conditions of the medicated and unmedicated test sessions for each subject, and then used to calculate the sub indices and composite index by computing difference scores between the two test sessions. FIG. 17 depicts the outcome of this analysis. It provides a scatter plot of the resulting scores, with the overall composite index vales plotted on the x-axis and the cognition sub index values plotted on the y-axis. Given the bi-directional nature of the index, improved cognitive function during the medicated test session relative to the unmedicated session would be reflected in positive scores in the overall index. Of the subjects in the study, 10/14 (or 71%) in fact did display a positive outcome on the overall index score, and on average (relative to the expected value of 0) across the group, stimulant medication was found to improve neurocognitive function [t(13)=3.15, p<0.008]. These results thus indicate that most of the participants displayed improved neurocognitive function in the medicated test session relative to the unmedicated session, and they are strikingly consistent with other reports that around 70% of children with ADHD respond positively to stimulant treatment.

Conclusions: These results demonstrate that the NCFC score can be used to assess children with ADHD who are being treated with stimulant medication in an effort to improve their attention and performance. In particular, the method might be especially useful for effectively and efficiently differentiating children with ADHD who respond positively to stimulant treatment from non-responders.

Modifications may be made in the present invention within the scope of the subjoined claims.

The subject's neural activity is measured while performing an attention-demanding task battery to determine one, or more, of the group selected from:

i. characterizing the subject's level of alertness by EEG measurement of the subject's frontal delta power associated with slow horizontal eye movements, posterior theta and delta power, and ratios of posterior theta to alpha and delta to alpha powers;

ii. characterizing the subject's level of alertness from the passive eyes-open and eyes-closed EEG, and/or evoked potential measures such as N100 and P300;

iii. characterizing the subject's mental effort and brain utilization by EEG measurement of the subject's parietal and prefrontal alpha powers;

iv. characterizing the subject's sustained focused attention and sustained divided attention by EEG measurement of the subject's frontal midline theta power;

v. characterizing the subject's preparatory attention and neurocognitive strategy respectively by EEG measurement of the subject's contingent negative variation evoked potential, and left to right and anterior to posterior ratios of the subject's alpha powers;

vi. characterizing the subject's perceptual and cognitive speed by EEG measurement of the subject's evoked potential peak latencies such as N100, P200 and P300;

vii. characterizing the subject's selective and transient focused attention by EEG measurement of the subject's N100, P300 and slow wave evoked potential amplitudes;

viii. characterizing the subject's working memory by EEG measurement of the subject's parietal and prefrontal alpha powers, frontal midline theta power, and P300 and slow wave evoked potential amplitude during a working memory task;

ix. characterizing the subject's intermediate term memory by measurement of differences between previously studied and newly presented information in the subject's N400, P600, slow wave, and other evoked potential amplitudes during an intermediate term memory task;

x. characterizing how the subject's brain and behavior respond to changes in mental workload by presenting more and less difficult versions of the same task during the same test session and measuring differences between the difficulty levels, and the difficulty levels and resting, in neural activity measures i–ix; and xi. characterizing the subject's quickness to adapt by measuring changes in the neural activity measures i–ix as the subject continues to perform the attention demanding tasks during the same test session.

xii. characterizing the subject's performance ability by measuring the speed, accuracy, and variability of responses during working memory tasks, intermediate term memory tasks, language reception and comprehension tasks, and other types of cognitive function tests.

REFERENCES CITED

Gevins, A., Smith, M. E., & McEvoy, L. K. (2002). Tracking the cognitive pharmacodynamics of psychoactive substances with combinations of behavioral and neurophysiological measures. *Neuropsychopharmacology*, 26, 27–39.

McEvoy, L. K., Pellouchoud, E., Smith, M. E., & Gevins, A. (2001). Neurophysiological signals of working memory in normal aging *Cognitive Brain Research*, 11, 363–376.

Gevins, A., & Smith, M. E. (2000). Neurophysiological measures of working memory and individual differences in cognitive ability and cognitive style. *Cerebral Cortex*, 10, 829–839.

McEvoy, L. K., Smith, M. E., & Gevins, A. (2000). Test-retest reliability of task-related EEG. *Clinical Neurophysiology*, 1, 457–463.

Gevins, A., & Smith, M. E. (1999). Detecting transient cognitive impairment with EEG pattern recognition. *Aviation, Space, and Environmental Medicine*, 70, 1018–1024.

Smith, M. E., McEvoy, L., & Gevins, A. (1999). Neurophysiological indices of strategy development and skill acquisition. *Cognitive Brain Research*, 7, 389–404.

McEvoy, L. Smith, M. E. & Gevins, A. (1998) Dynamic cortical networks of verbal and spatial working memory. *Cerebral Cortex*, 8, 563–574.

Gevins, A., Smith, M. E., Leong, H., et al. (1998). Monitoring working memory load during computer based tasks with EEG pattern recognition methods. *Human Factors*, 40 (1),79–91.

Gevins, A., Smith, M. E., McEvoy, L., & Yu, D. (1997). High resolution EEG mapping of cortical activation related to working memory. *Cerebral Cortex*, 7, 374–385.

Gevins, A. S., Smith, M. E., Le, J., Leong, H., Bennett, J., Martin, N., McEvoy, L., Du., R., & Whitfield, S. (1996) High resolution evoked potential imaging of the cortical dynamics of human working memory. *Electroencephalography and Clinical Neurophysiology*, 98 (4), 327–348.

Gevins, A. S., Cutillo, B. A., & Smith, M. E. (1995). Regional modulation of high resolution evoked potentials during verbal and nonverbal matching tasks. Electroenceph. Clin Neurophysiol., 94, 129–147.

What is claimed is:

1. The method of measuring changes in a human subject's fundamental cognitive brain functions, the changes, for example, being due to disease, injury, remedial treatment, the utilization of medicines and normal variation within and between days and over a period of time, including the steps of:

(a) presenting an attention-damanding task to the subject, which engages one or more of the subject's fundamental cognitive functions, and, simultaneously;

(b) at least once, measuring the subject's behavioral responses to the task, and neuroelectric activity at the subject's scalp using a set of electroencephalograph (EEG) electrodes and amplifier and analog/digital converters, to provide a set of baseline digital data representing the subject's baseline state behavioral responses and neuroelectric activity response to the task;

(c) at least once again, measuring the subject's behavioral responses to the task, and neuroelectric activity at the subject's scalp using a set of electroencephalograph (EEG) electrodes and amplifier and analog/digital converters, to provide a set of possibly altered state digital data representing the subject's possibly altered state behavioral responses and neuroelectric activity in response to the task;

(d) in a computer system, comparing the subject's baseline state and possibly altered state digital data using a mathematical function derived from behavioral responses and EEG derived neuroelectric activity responses of a reference group of subjects performing the same task recorded in their baseline and altered state conditions, the comparison using a multivariate statistical method combining measures of task performance with brain function measures in a single comparison, and (e) deriving one or more scores for the subject based on the comparison described in (d) and determining the significance of those scores.

2. The method of measuring changes in a human subject's fundamental cognitive brain functions, the changes, for example, being due to disease, injury, remedial treatment, the testing of medicines and normal variation within and between days and over a period of time, including the steps of:

(a) presenting an attention-demanding task to the subject, which engages the subject's fundamental cognitive functions, and, simultaneously;

(b) at least once, measuring the subject's behavioral responses to the task, and associated brain function using functional magnetic resonance imaging (fMRI), alone or in combination with EEG, to provide a set of baseline digital data representing the subject's behavioral responses and brain activity in response to the task;

(c) at least once again, measuring the subject's behavioral responses to the task, and associated brain function using functional magnetic imaging (fMRI), alone or in combination with EEG, to provide a set of possibly altered state digital data representing the subject's behavioral responses and brain activity in response to the task;

(d) in a computer system, comparing the subject's baseline state and possibly altered state digital data using a mathematical function derived from the behavioral responses and fMRI derived brain activity responses, alone or in combination with EEG derived neuroelectric activity responses, of a reference group of subjects performing the same task recorded in their baseline and altered state conditions, the comparison using a multivariate statistical method to combine the measures of task performance with brain function measures in a single comparison; and (e) deriving one or more scores for the subject based on the comparison described in (d) and determining the significance of those scores.

3. The method of measuring change in a human subject's fundamental cognitive brain functions, the changes, for example, being due to disease, injury, remedial treatment, the testing of medicines and normal variation within and between days and over a period of time, including the steps of:

(a) presenting an attention-demanding task to the subject, which engages the subject's fundamental cognitive functions, and, simultaneously;

(b) at least once, measuring the subject's behavioral responses to the task, and associated brain function using magnetoencephalograms (MEG), alone or in combination with EEG, to provide a set of baseline digital data representing the subject's behavioral responses and brain activity in response to the task;

(c) at least once again, measuring the subject's behavioral responses to the task, and associated brain function using magnetoencephalograms (MEG), alone or in combination with EEG, to provide a set of possibly altered state digital data representing the subject's behavioral responses and brain activity in response to the task;

(d) in a computer system, comparing the subject's baseline state and possibly altered state digital data to derive an overall score using a mathematical function derived from the behavioral responses and MEG derived brain activity responses, alone or in combination with EEG derived neuroelectric activity responses, of a reference group of subjects performing the same task recorded in their baseline and altered state conditions, the comparison using the multivariate statistical method to combine measures of task performance with the brain function measures in a single comparison; and (e) deriving one or more scores for the subject based on the comparison described in (d) and determining the significance of those scores.

4. The method of measuring changes in a human subject's fundamental cognitive brain functions, the changes, for example, being due to disease, injury, remedial treatment, the testing of medicines and normal variation within and between days and over a period of time, including the steps of:

(a) presenting an attention-demanding task to the subject, which engages the subject's fundamental cognitive functions, and, simultaneously;

(b) at least once, measuring the subject's behavioral responses to the task, and neuroelectric activity at the subject's scalp using a set of electroencephalograph (EEG) electrodes and amplifier and analog/digital converters, to provide a set of baseline digital data representing the subject's behavioral responses and neuroelectric activity in response to the task;

(c) at least once again, measuring the subject's behavioral responses to the task, and neuroelectric activity at the subject's scalp using a set of electroencephalograph (EEG) electrodes and amplifier and analog/digital converters, to provide a set of possibly altered state digital data representing the subject's behavioral responses and neuroelectric activity in response to the task;

(d) in a computer system, comparing the subject's baseline state and possibly altered state digital data to behavioral responses and EEG derived neuroelectric activity responses of a reference group of subjects performing the same task recorded in their baseline and altered states, the comparison using a multivariate statistical method combining measures of task performance with brain function measures in a single comparison, and (e) deriving a score for the subject based on the comparison of (d) and determining the significance of the score.

5. The method of measuring changes in a human subject's fundamental cognitive brain functions, the changes, for example, being due to disease, injury, remedial treatment, the testing of medicines and normal variation within and between days and over a period of time, including the steps of:

(a) presenting an attention-demanding task to the subject, which engages one or more of the subject's fundamental cognitive functions, and, simultaneously;

(b) at least once, measuring the subject's behavioral responses to the task, and neuroelectric activity at the subject's scalp using a set of electroencephalograph (EEG) electrodes and amplifier and analog/digital converters, to provide a set of baseline digital data representing the subject's baseline state behavioral responses and neuroelectric activity in response to the task;

(c) at least once again, measuring the subject's behavioral responses to the task, and neuroelectric activity at the subject's scalp using a set of electroencephalograph (EEG) electrodes and amplifier and analog/digital converters, to provide a set of possibly altered state digital data representing the subject's possibly altered state behavioral responses and neuroelectric activity in response to the task;

(d) computing measures from the baseline and possibly altered state sets of digital data and grouping the measures into one or more classes, called for example, Behavioral Performance, Neurophysiological Cognitive and Neurophysiological Alertness; and applying rules, based on expert neuropsychological and neurophysiological knowledge, to each of the measures within each of the classes to determine if the measures differ in an expected manner between each subject's baseline and subsequent, possibly altered, states;

(e) in a computer system, comparing the subject's data analyzed as in (d) to identically analyzed data of a reference group of subjects performing the same task recorded in their baseline and altered state conditions, the comparison using a multivariate statistical method combining measures of task performance with brain function measures in a single comparison; and (f) deriving a score for the subject based on the comparison of (e) and determining the significance of the score.

6. The method of claims 1, 2, 3, 4 or 5 wherein the digital data measures of behavioral responses and neuroelectric activity are grouped into one or more classes, called for example, Behavioral Performance, Neurophysiological Cognitive and Neurophysiological Alertness; and rules, based on expert neuropsychological and neurophysiological knowledge, are applied to each of the measures within each of the classes to determine if the measures differ in an expected manner between each subject's baseline and subsequent, possibly altered, states.

7. The method of claims 1, 2, 3, 4 or 5 wherein the comparison is computed using a neural network, or other statistical classification algorithm, that combines the outputs of the classes into a score, called for example the Neurocognitive Function Change (NCFC) score, that distinguishes baseline and altered states.

8. The method of claims 1, 2, 3, 4 or 5 wherein the attention-demanding task is a brief cognitive test battery.

9. The method of claims 1, 2, 3, 4 or 5 wherein at least some of the behavioral performance measures from the attention-demanding tasks combine measures of task performance, for example the subject's speed and accuracy of response to each task trial.

10. The method of claims 1, 2, 3, 4 or 5 in which the test battery tests the subject's attention and/or memory, and/or language functions.

11. The method of claims 1, 2, 3, 4 or 5 wherein the subject performs a series of repetitions of easy and more difficult versions of at least some of the tasks.

12. The method of claims 1, 2, 3, 4 or 5 wherein in (a) of the claim a passive control condition is presented to the subject for comparison to the attention-demanding tasks.

13. The method of claims 1, 2, 3, 4 or 5 wherein in (a) of the claim the attention-demanding task is presented by a digital computer.

14. The method of claims 1, 2, 3, 4 or 5 and determining the various ways of determining the baseline (prior) state and/or possibly altered (subsequent) state selected from the group of: (i) the subject's first recording, (ii) the subject's most recent recording, (iii) a weighted average of all the subject's prior recordings, (iv) a particular prior recording before initiation of a drug or other therapy, (v) a specified subset of prior recordings from the subject, and (vi) baseline states previously determined from a normative reference group of subjects with demographic or health characteristics similar to those of the subject.

15. The method of claims 1, 2, 3, 4 or 5 and determining one or more of the following to determine whether a Neurocognitive Function Change (NCFC) score represents a sufficiently significant change from the baseline state (to be called an altered state) by: (i) statistical comparison of a subject's NCFC score on a particular test day or days with the normal range of variation of the subject's NCFC score resulting from comparing the subject's prior baseline states to each other using the mathematical function in (d) of claims 1, 2, 3 or 4 or (e) of claim 5; (ii) statistical comparison of a subject's NCFC score on a particular test day or days with a typical normal range of variation of the NCFC scores of a normative reference group of subjects resulting from comparing each member of the group's baseline states to each other using the mathematical function in (d) of claims 1, 2, 3 or 4 or (e) of claim 5.

16. The method of claims 1, 2, 3, 4 or 5 and determining one or more of the following to determine whether a Neurocognitive Function Change (NCFC) score represents a sufficiently sianificant change from the baseline state (to be called an altered state) by: (i) statistical comparison of a subiect's NCFC score on a particular test day or days with the normal range of variation of the subiect's NCFC score resulting from comparing the subiect's prior baseline states to each other using the mathematical function in (d) of claims 1, 2, 3 or 4 or (e) of claim 5; (ii) statistical comparison of a subject's NCFC score on a particular test day or days with a typical normal range of variation of the NCFC scores of a normative reference group of subjects resulting from comparing each member of the group's baseline states to each other using the mathematical function in (d) of claims 1, 2, 3 or 4 or (e) of claim 5 wherein a subsequent state that was determined to be an altered state is further analyzed to determine how the state is altered by statistically comparing the outputs of each class in the subject's NCFC function to the normal range of variation of the outputs of each class, and if an output for a class is significant, examining the outputs of the individual rules and measures within each class; wherein the normal range of variation of the outputs of each class is determined by one or more of the following: (i) analysis of the outputs of the individual rules of the subject's NCFC functions resulting from comparing the subject's prior baseline states to each other using the mathematical function in (d) of claims 1, 2, 3 or 4 or (e) of claim 5; (ii) analysis of the outputs of the individual rules of a normative group of subjects' NCFC functions resulting from comparing each member of the group's prior baseline states to each other using the mathematical function in (d) of claims 1, 2, 3 or 4 or (e) of claim 5.

17. The method of claims 1, 2, 3, 4 or 5 employed to test the effect of medicine on a subject in which least one set of baseline digital data is obtained before administration of the medicine to the subject and at least one set of possibly altered state digital data is obtained after administration of the medicine to the subject.

18. The method of claims 1, 2, 3, 4 or 5 employed to test the effectiveness of a remedial program to improve cognitive functioning in which at least one set of baseline digital data is obtained before administration of the remedial program to the subject and at least one set of possibly altered state digital data is obtained after administration of the remedial program.

19. The method of claims 1, 2, 3, 4 or 5 employed to measure the effect of fatigue on a subject in which at least one set of baseline digital data is obtained when the subject is in an alert, rested state and at least one set of possibly altered state digital data is obtained after the subject has been deprived of a normal amount of sleep or is otherwise fatigued.

20. The method of claims 1, 2, 3, 4 or 5 employed to measure the effect of injury or disease on a subject in which at least one set of baseline digital data is obtained when the subject is in a healthy, uninjured state and at least one set of possibly altered state digital data is obtained after the subject has been injured or contracted a disease.

21. The method of claims 1, 2, 3, 4 or 5 and comparing a possibly injured or diseased baseline state of a subject with baseline data from a normal reference group.

22. The method of claims 1, 2, 3, 4 or 5 employed to measure recovery from injury or disease in which at least one set of baseline digital data is obtained after the subject has been injured or contracted a disease and at least another set of possibly altered digital data is subsequently obtained.

23. The method of claims 1, 2, 3, 4 or 5 alone or in concert with symptomatic or asymptomatic blood borne or other measurable marker shown to be associated with a disease or condition, in order allow early detection of impairment or improvement due to that disease or condition or a treatment, thus being able to speedily predict and evaluate efficacy of a treatment.

24. The method of claims 1, 2, 3, 4 or 5 wherein the task is not culturally biased, as it does not involve reading a language.

25. The method of claims 1, 2, 3, 4 or 5 and additionally presenting the subject with control conditions in which the subject sits passively with eyes opened and then with eyes closed.

26. The method of claims 1, 2, 3, 4 or 5 and measuring the subject's neuroelectric activity in (b) and/or (c) of the claim while performing the task of (a) to determine one, or more, of the group selected from:
i. characterizing the subject's level of alertness;
ii. characterizing the subject's mental efforts and brain utilization;
iii. characterizing the subject's sustained focused attention and working memory;
iv. characterizing the subject's sustained divided attention;
v. characterizing the subject's preparatory attention and neurocognitive strategy;
vi. characterizing the subject's perceptual and cognitive speed;
vii. characterizing the subject's selective attention and transient focused attention;
viii. characterizing the subject's intermediate term memory;
ix. characterizing how the subject's brain and behavior respond to changes in mental workload by presenting more and less difficult versions of a task during the same test session;
x. characterizing the subject's quickness to adapt by presenting repeated trials of the same task during one test session.

27. The method of claims 1, 2, 3, 4 or 5 and measuring the subject's neuroelectric activity in (b) and/or (c) of the claim while performing the task of (a) to determine one, or more, of the group selected from:
i. characterizing the subject's level of alertness by EEG measurement of the subject's frontal delta power associated with slow horizontal eye movements, posterior theta and delta power, and ratios of posterior theta to alpha and delta to alpha powers;
ii. characterizing the subject's level of alertness from the passive eyes-open and eyes-closed EEG, and/or evoked potential measures such as N100 and P300;
iii. characterizing the subject's mental effort and brain utilization by EEG measurement of the subject's parietal and prefrontal alpha powers;
iv. characterizing the subject's sustained focused attention and sustained divided attention by EEG measurement of the subject's frontal midline theta power;
v. characterizing the subject's preparatory attention and neurocognitive strategy respectively by EEG measurement of the subject's Contingent Negative Variation evoked potential, and left to right and anterior to posterior ratios of the subject's alpha powers;
vi. characterizing the subject's perceptual and cognitive speed by EEG measurement of the subject's evoked potential peak latencies such as N100, P200 and P300;
vii. characterizing the subject's selective and transient focused attention by EEG measurement of the subject's N100, P300 and Slow Wave evoked potential amplitudes;
viii. characterizing the subject's working memory by EEG measurement of the subject's parietal and prefrontal alpha powers, frontal midline theta power, and P300 and Slow Wave evoked potential amplitude during a working memory task;
ix. characterizing the subject's intermediate term memory by measurement of differences between previously studied and newly presented information in the subject's N400, P600, Slow Wave, and other evoked potential amplitudes during an intermediate term memory task;

x. characterizing how the subject's brain and behavior respond to changes in mental workload by presenting more and less difficult versions of the same task during the same test session and measuring differences between the difficulty levels, and the difficulty levels and resting, in neural activity measures i–ix; and xi. characterizing the subject's quickness to adapt by measuring changes in the neural activity measures i–ix as the subject to perform the attention demanding tasks during the same test session.

\* \* \* \* \*